US012576123B2

(12) United States Patent
Apte et al.

(10) Patent No.: US 12,576,123 B2
(45) Date of Patent: Mar. 17, 2026

(54) EPITOPE-BASED APPROACH FOR ALLERGY TREATMENTS AND INHIBITORS FOR CROHN'S DISEASE

(71) Applicant: PSOMAGEN INC., Rockville, MD (US)

(72) Inventors: Zachary Apte, San Francisco, CA (US); Jessica Richman, San Francisco, CA (US); Daniel Almonacid, San Francisco, CA (US); Mario Saavedra, San Francisco, CA (US); Ingrid Araya, San Francisco, CA (US)

(73) Assignee: Psomagen, Inc., Rockville, MD (US)

( * ) Notice: Subject to any disclaimer, the term of this patent is extended or adjusted under 35 U.S.C. 154(b) by 1146 days.

(21) Appl. No.: 17/438,515

(22) PCT Filed: Mar. 13, 2020

(86) PCT No.: PCT/US2020/022701
§ 371 (c)(1),
(2) Date: Sep. 13, 2021

(87) PCT Pub. No.: WO2020/186190
PCT Pub. Date: Sep. 17, 2020

(65) Prior Publication Data

US 2022/0233686 A1 Jul. 28, 2022

Related U.S. Application Data

(60) Provisional application No. 62/832,811, filed on Apr. 11, 2019, provisional application No. 62/828,074,
(Continued)

(51) Int. Cl.
*A61K 38/00* (2006.01)
*A61P 37/08* (2006.01)
(Continued)

(52) U.S. Cl.
CPC .............. *A61K 38/00* (2013.01); *A61P 37/08* (2018.01); *C07K 7/08* (2013.01); *A61K 39/35* (2013.01); *G01N 2800/24* (2013.01)

(58) Field of Classification Search
CPC ......... A61K 39/35; A61K 38/00; A61P 37/08; A61P 37/04; C07K 14/415; C07K 7/08; G01N 2800/24
See application file for complete search history.

(56) References Cited

U.S. PATENT DOCUMENTS

2016/0375130 A1 12/2016 O'Hehir et al.
2017/0304432 A1 10/2017 Hearl et al.

FOREIGN PATENT DOCUMENTS

JP 2002-501748 A 1/2002
JP 2017-521064 A 8/2017
(Continued)

OTHER PUBLICATIONS

Thakur, R. and Shankar, J. (2016). In silico Identification of Potential Peptides or Allergen Shot Candidates Against Aspergillus fumigatus. BioResearch Open Access 5(1): 330-341. (Year: 2016).*
(Continued)

*Primary Examiner* — Gary B Nickol
*Assistant Examiner* — Bailey M Morgan
(74) *Attorney, Agent, or Firm* — Morgan, Lewis & Bockius LLP

(57) ABSTRACT

The present disclosure relates to pharmaceutical compounds and compositions and methods for treating an allergy and Crohn's disease. Methods for treating an allergy can include (a) predicting potential epitopes based proteomes of microbiome and that of an allergen, (b) filtering the potential epitopes obtained in step a) to result in a list of epitopes; and (c) reengineering the list of epitopes obtained in step b) to result in the new epitope. Methods for treating Crohn's
(Continued)

disease can include (a), identifying one or more binding regions of an HLA class II protein and/or hemagglutinin to I2 superantigen; (b) determining a first peptide sequence corresponding to the one or more binding regions, and (c) producing a peptide inhibitor having a second peptide sequence that is a mutation of the first peptide sequence, wherein the second peptide sequence has a stronger binding affinity to the I2 superantigen than the first peptide sequence.

12 Claims, 8 Drawing Sheets

Specification includes a Sequence Listing.

Related U.S. Application Data filed on Apr. 2, 2019, provisional application No. 62/824,095, filed on Mar. 26, 2019, provisional application No. 62/817,564, filed on Mar. 13, 2019, provisional application No. 62/817,621, filed on Mar. 13, 2019.

(51) Int. Cl.
*C07K 7/08* (2006.01)
*A61K 39/35* (2006.01)

(56) References Cited

FOREIGN PATENT DOCUMENTS

WO 2013/187906 A1 12/2013
WO 2017/186808 A1 11/2017

OTHER PUBLICATIONS

Prickett et al. (2013). "Ara h 1 CD4+ T cell epitope-based peptides: candidates for a peanut allergy therapeutic." Clin. Exp. Allergy, 43(6):684-697. (Year: 2013).*

Lundegaard et al. (2012). "Predictions versus high-throughput experiments in T-cell epitope discovery: competition or synergy?" Expert Rev. Vaccines, 11(1): 43-54. (Year: 2012).*

Hayes et al. (2015). "In silico tools for exploring potential human allergy to proteins." Drug Discov. Today Dis. Models, 17-18:3-11. (Year: 2015).*

Jiang et al. (2010). "GenBank ADQ53859.1: Ara h 3 allergen [*Arachis hypogaea*]" as obtained online at ncbi.nim.nih.gov [retrieved on Jun. 10, 2025]. Retrieved from the internet: <https://www.ncbi.nlm.nih.gov/protein/ADQ53859.1> (Year: 2010).*

Office Action issued in corresponding European Patent Application No. 20769559.4 dated Nov. 18, 2022.

Office Action issued in corresponding Japanese Patent Application No. 2021-552937 dated Sep. 16, 2022 with English Translation.

Piersam et al: "Proteolytic processing of the peanut allergen Ara h 3" (Mol. Nutr. Food Res. 2005, vol. 49, p. 744-755).

S. R. Prickett et al: "Ara h 1 CD4+ T cell epitope-based peptides: candidates for a peanut allergy therapeutic" (Clinical & Experimental Allergy, 2013 vol. 43, p. 684-697).

Manish Ramesh et al: "Peanut T-cell epitope discovery: Ara h 1" (Journal of Allergy and Clinical Immunology vol. 137, Issue 6, Jun. 2016, pp. 1764-1771.e4).

International Search Report issued in corresponding International Patent Application No. PCT/US2020/022701 dated Sep. 18, 2020.

Jiang et al., Ara h 3 allergen [*Arachis hypogaea*]. Genbank entry (online). National Institute of Biotechnology Information, (Nov. 23, 2010) (retrieved Jul. 6, 2020), <<https://www.ncbi.nlm.nih.gov/protein/ADQ53859.1>>.

Prickett et al., "Safety and Tolerability of a Novel Peptide-Based Immunotherapy for Peanut Allergy," Journal of Allergy and Clinical Immunology, 143 (2): AB431 (Feb. 1, 2019).

* cited by examiner

EPITOPE-BASED APPROACH FOR ALLERGY TREATMENTS AND INHIBITORS FOR CROHN'S DISEASE

CROSS-REFERENCE TO RELATED APPLICATIONS

This application claims the benefit of U.S. Provisional Patent Application No. 62/817,564 filed Mar. 13, 2019 entitled "Epitope-Based Approach For Virulence Factors And/Or Food Allergy Treatments And Detection Methods, Systems, And/Or Therapeutics"; U.S. Provisional Patent Application No. 62/817,621 filed Mar. 13, 2019 entitled "Epitope-Based Approach As A Detection And/Or Treatment Method, System, And/Or Therapeutic Composition For Peanuts Allergy And/Or Related Dietary Food"; U.S. Provisional Patent Application No. 62/824,095 filed Mar. 26, 2019 entitled "Unlocking The Microbiome For New Opportunities In Drug Discovery"; U.S. Provisional Patent Application No. 62/828,074 filed Apr. 2, 2019 entitled "Design Of Inhibitors Of Crohn's Disease-Associated I2 Superantigen And MHC-II"; U.S. Provisional Patent Application No. 62/832,811 filed Apr. 11, 2019 entitled "Unlocking The Microbiome For New Opportunities In Drug Discovery", all of which are incorporated by reference herein in their entirety.

SEQUENCE LISTING SUBMISSION VIA EFS-WEB

A computer readable text file, entitled "SequenceListing.txt," created on May 14, 2020 with a file size of 57,696 bytes contains the sequence listing for this application and is hereby incorporated by reference in its entirety.

BACKGROUND

Food allergy can include an hypersensitive immune response caused by a food exposure, particularly an agent, typically a protein. The origin of food allergy is unknown. Some proposal factors are genetic, excessive hygiene, geographical factors, amongst others.

Products which are used to treat diseases derived from allergens and pathogens, usually take advantage of the classic concept of a vaccine which has been developed to resemble the natural pathogen. Some treatments include some antigenic components typical of a pathogen or allergen; in other cases the components used had been inactivated, weakened and/or mimicked. Subcutaneous immunotherapy, recombinant vaccines, oral immunotherapy (OIT) and probiotics sublingual immunotherapy, are recent approaches reported to treat food allergy.

However, the microbiome can play an important role in preventing food allergy, and/or stimulating an adverse reaction. Epitopes, have been described as a valuable tool, to develop new methods against the pathogens, allergy or infectious agents and particularly epitope-based vaccines are intended to trigger an immune response through different proteins from a pathogen or allergen, and are focused on some specific short amino acid sequences which can be isolated to be rationally modified. The ability to rationally modify the sequence of epitopes aimed by in-silica tools can result in an increase or decrease, in the activity of those epitopes, which otherwise would not trigger an optimal immunity response. In this regard, an epitope can be a fragment derived from an antigen, which can be recognized by antibodies or immune cells, such as B or T cells. Epitopes from protein antigens can be classified into conformational or linear epitopes. Conformational epitopes are composed of discontinuous sections of a protein, meanwhile linear epitopes are formed by a continuous sequence of amino acids from an antigen.

Identification of potential T-cell epitopes in the food allergens can be important for development of peptide-based immunotherapy. Traditional methods to identify T-cell epitopes from allergens use overlapping short peptides spanning a full-length protein. However, this approach can be expensive because many peptides must be tested.

Peanut allergy is the most common food allergy and one of the causes of food-induced anaphylaxis; a sudden and potentially deadly condition that requires immediate attention and treatment, especially among school-aged children in the United States. Symptoms of anaphylaxis include impaired breathing, swelling in the throat, drop in blood pressure, pale skin or blue lips, fainting and dizziness. Anaphylaxis can be fatal unless treated immediately with epinephrine(adrenaline).

In recent years the number of peanut allergy cases reported has risen. In May 2010, a study noted that the rate of peanut allergies in children had more than tripled between 1997 and 2008. Thus, avoiding peanut and peanut-derived products and/or treatment with adrenaline are the only methods to prevent the allergy.

Recent approaches reported to treat peanut allergy include subcutaneous immunotherapy, oral immunotherapy (OIT), and probiotics sublingual immunotherapy. However, those approaches include using crude peanut extract (CPE) which may cause life-threatening anaphylactic reactions or low efficacy.

Differently, T-cell epitopes-based immunotherapy lacks of these disadvantages, providing desensitization avoiding secondary effects, because those epitopes are too short to induce cross-linking to allergen-specific IgE on basophils or mast cells, like CPE can do. This strategy was designed based on experimental results that demonstrated that tolerance against a complete allergen can be induced using small allergen-derived peptides, which are recognized by allergen specific T cells. Thus, it has been described that cocktails of defined epitopes or chimeric protein arrangements including the target epitopes can elicit convenient humoral or cellular immune responses.

Identification of potential T-cell epitopes in the peanut major allergens is essential for development of peptide-based immunotherapy. Traditional methods to identify T-cell epitopes from allergens use overlapping short peptides spanning a full-length protein, such as Ara h1. However, this approach can be expensive because many peptides must be tested.

Crohn's disease (CD) is a type of inflammatory bowel disease, which can be associated with an abnormal immune system response that causes chronic inflammation in the digestive tract. Common symptoms of CD include abdominal pain, severe diarrhea, fatigue, loss of appetite, fever, cramping and weight loss. Complications of the disease can also cause ulcers within the intestines, fissures in the lining of the anus, increased risk of colorectal cancer, and development of chronic health conditions, including cardiovascular disease, respiratory disease, cancer, arthritis, kidney and liver diseases. CD is more frequently diagnosed in young adults. Family history and cigarette smoking could be risk factors in the development of Crohn's disease.

The causes of CD remain unknown, however genetic and environmental factors play significant roles in the pathogenesis. Evidence suggests that commensal bacteria is important in pathogenesis, and therefore bacteria can trigger immune activation in CD. Studies have identified a novel microbial T-cell superantigen I2 from *Pseudomonas fluorescens* that is involved in the pathogenesis of CD. The superantigen interacts with human MHC class 11 HLA-DR producing a non-specific activation of T-cells, which leads to activation of a large number of T-cells and to a massive cytokine release, and leading to a greater frequency of strictures, internal perforations, and/or other complications, which can require a small bowel surgery for treatment. The binding between I2 T-cell superantigen (implicated in the pathogenesis of Crohn's disease) and Human MHC Class 11 leads to a massive cytokine release and a large number of T-cells activation, which produce a greater frequency of strictures, internal perforations and small bowel surgery.

BRIEF SUMMARY OF THE DISCLOSURE

In some embodiments, the present disclosure relates to a peptide for treating an allergy comprising a sequence of $X_1X_2X_3X_4X_5X_6X_7X_8X_9X_{10}X_{11}X_{12}X_{13}X_{14}X_{15}$ (SEQ ID NO: 1); wherein:

$X_1$ is E;
$X_2$ is E or T;
$X_3$ is Q or P;
$X_4$ is G;
$X_5$ is A or W;
$X_6$ is I;
$X_7$ is V;
$X_8$ is T;
$X_9$ is V;
$X_{10}$ is K;
$X_{11}$ is G or Q;
$X_{12}$ is G;
$X_{13}$ is L;
$X_{14}$ is R; and
$X_{15}$ is I, H or W.

In some embodiments, the present disclosure relates to a peptide comprising a sequence of $X_1X_2X_3X_4X_5X_6X_7X_8X_9X_{10}X_{11}X_{12}X_{13}X_{14}X_{15}$ (SEQ ID NO: 2); wherein:

$X_1$ is N, A, C, D, F, G, H, L, M, P, R, S, T, W, or Y;
$X_2$ is Y, C, F, G, H, L, M, N, T, V, or W;
$X_3$ is A, C, E, F, G, H, I, K, L, Q, S, T, or Y;
$X_4$ is Y, C, D, F, H, I, K, L, M, N, Q, R, or S;
$X_5$ is N, A, D, H, I, K, L, M, P, Q, S, T, V, or W;
$X_6$ is Y, A, C, D, E, F, G, L, P, R, T, V, or W;
$X_7$ is S, A, C, F, I, L, N, P, Q, R, T, V, W, or Y;
$X_5$ is V, A, E, H, I, K, L, M, P, Q, R, W, or Y;
$X_9$ is V, A, C, D, E, F, G, H, K, L, N, Q, T, or W;
$X_{10}$ is G, A, E, F, H, I, K, L, N, P, Q, R, S, V, or Y;
$X_{11}$ is G, A, C, F, I, K, L, M, N, Q, R, S, T, V, W, or Y;
$X_{12}$ is V, A, D, E, H, K, M, N, S, or W;
$X_{13}$ is A, C, D, G, H, L, P, R, S, V, Y, or L;
$X_{14}$ is L, A, D, F, G, H, M, N, P, R, S, T, W, or Y; and
$X_{15}$ is P, D, F, H, I, K, M, T, or W.

In an embodiment, the peptide can have a sequence of EEQGAIVTVKGGLRI (SEQ ID NO: 3). In an embodiment, the peptide can have a sequence of ETPGWIVTVKGGLRI (SEQ ID NO: 4).

In an embodiment, the peptide has more than 60%, 65%, 70%, 75%, 80%, 85%, 90%, or 95% sequence identity to one or more of the peptides stated above. One or more of the peptides stated above can be in the form of a pharmaceutical composition.

In some embodiments, the present disclosure relates to a method of treating an allergy comprising administering an effective amount of a pharmaceutical composition comprising any one of the peptides described herein to a subject, e.g., a human subject in need thereof. Such pharmaceutical composition can further comprise a pharmaceutically acceptable excipient, e.g., fillers, diluents, disintegrants, binders and lubricants. In an embodiment, the pharmaceutical composition further comprises a pharmaceutically acceptable additive. In an embodiment, the additive is selected from the group consisting of flavoring agents, coloring agents, taste-masking agents, pH-adjusting agents, buffering agents, preservatives, stabilizing agents, anti-oxidants, wetting agents, humidity-adjusting agents, surface-active agents, suspending agents and absorption enhancing agents.

In some embodiments, the present disclosure relates to a method for identifying an epitope for treating an allergy comprising the steps:

a). predicting potential epitopes based proteomes of microbiome and that of an allergen;
b). filtering the potential epitopes obtained in step a) to result in a list of epitopes;
c). reengineering the list of epitopes obtained in step b) to result in the new epitope.

In an embodiment, a filter criterion is applied in step b). In an embodiment, the filter criterion comprises the potential epitopes having more than 60%, 65%, 70%, 75%, 80%, 85%, 90%, or 95% sequence identity to any one or all of the peptide described herein. In an embodiment, the filter criterion comprises removing sequences that are not directly associated with bacteria. In an embodiment, the filter criterion comprises the molecular docking over human leukocyte antigen (HLA) class II.

In some embodiments, the present disclosure relates to a method for producing a peptide inhibitor for the treatment of Crohn's disease, the method comprising:

a). identifying one or more binding regions of an HLA class II protein and/or hemagglutinin to I2 superantigen;
b). determining a first peptide sequence corresponding to the one or more binding regions; and
c). producing a peptide inhibitor having a second peptide sequence that is a mutation of the first peptide sequence, wherein the second peptide sequence has a stronger binding affinity to the I2 superantigen than the first peptide sequence.

In an embodiment, the mutation is a single amino acid mutation of the first peptide sequence.

In an embodiment, the first peptide sequence comprises QGALANIAVDKA (SEQ ID NO: 5). In an embodiment, the first peptide sequence comprises KQNTLK (SEQ ID NO: 6).

In some embodiments, the present disclosure relates to a pharmaceutically acceptable compound having a chemical structure selected from the group consisting of:

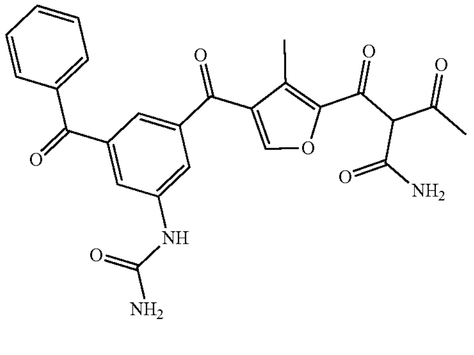

-continued

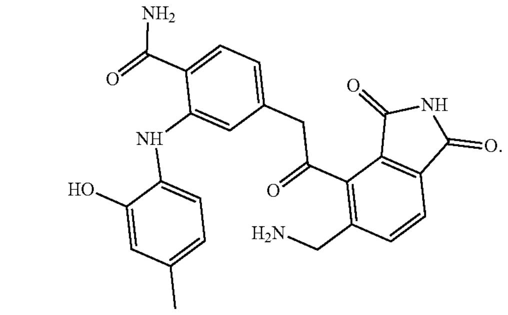

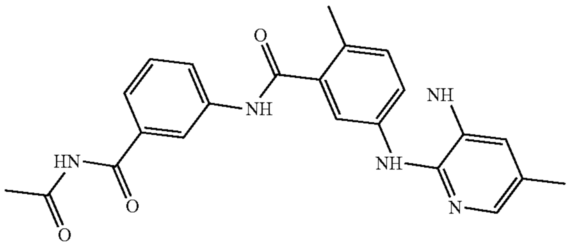

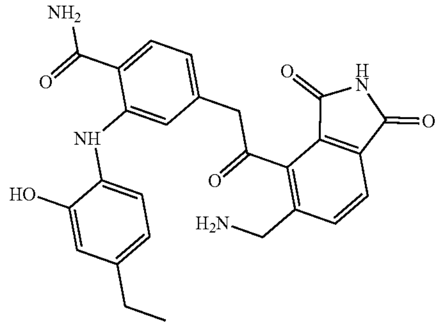

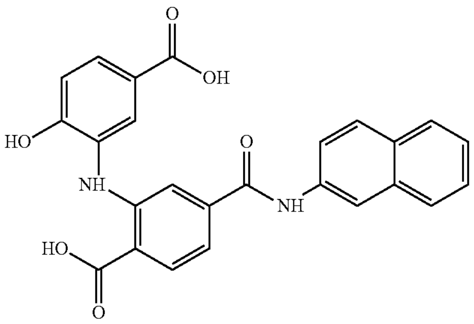

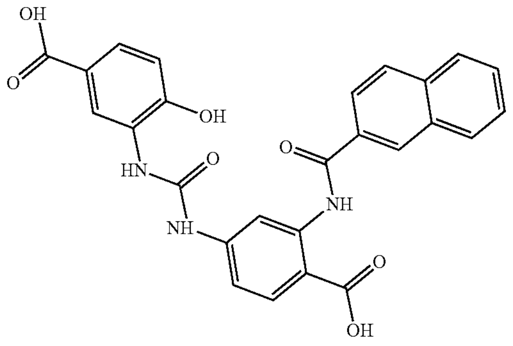

-continued

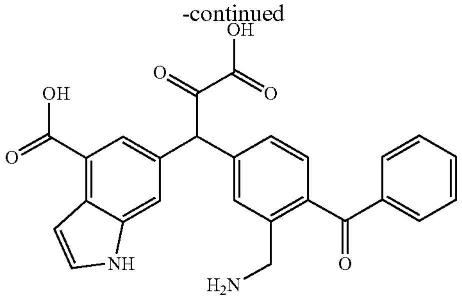

and pharmaceutically acceptable salts thereof.

In some embodiments, the present disclosure relates to a method of treating Crohn's disease comprising administering an effective amount of a pharmaceutical composition comprising any one or more of the compound described herein to a subject in need thereof.

DETAILED DESCRIPTION OF THE DISCLOSURE

Definition

Figure 1:
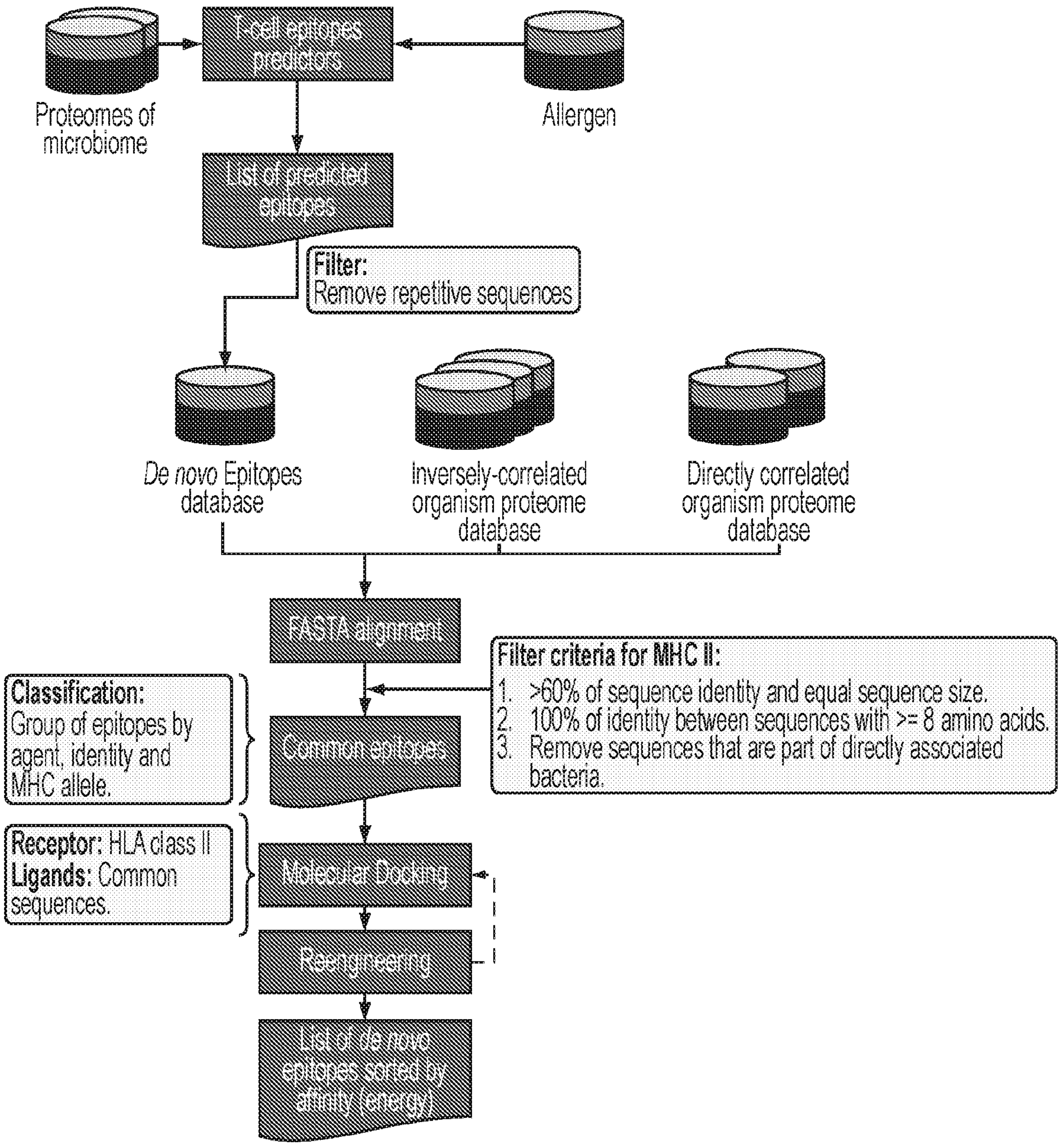
FIG. 1 illustrates a specific example of a general view of the workflow employed to identify "de novo" epitopes from allergen proteins associated to a particular condition.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

Embodiments of methods and/or systems can use, include, and/or be associated with bacteria and/or microorganisms strains, bacterial-derived products, proteins and/or epitopes belonging to bacteria, archaea and/or other suitable taxa, such as matching those found in food allergen proteomes. In an embodiment, bacteria-derived epitopes are used to trigger an immune response (e.g., as common vaccines do, etc.), by mimicking the response enabled by the an immune reaction and/or food allergen exposure, and/or decrease the immune reaction caused by the food allergen, virulence factors and/or similar agents. Such approaches (and/or other approaches described herein) can be used in developing, performing, generating, and/or can be otherwise associated with a detection method and/or for preventive vaccines, immunotherapy methods and/or other treatments. In an embodiment, the bacterial-derived products, up to and including the bacterium itself, are used to trigger an immune response, as common vaccines do, by mimicking the response enabled by an allergen and/or a virulence factors derived infection.

In examples, the epitope-based approach towards a vaccine development can be a preventive approach for diseases that affect the immune system, such as allergies, autoimmune and/or infectious diseases. In specific examples, any suitable vectors can be used including vaccines, suitable delivery methods such as DNA vectors that code the peptide (e.g., epitope), uses of nanoparticles, polymer-based methods, etc.

Virulence factors related with pathogenicity agents, describe an immune response from B or T cells. Under the same idea of food allergy, epitopes from virulence factors can be applied to detection and treatment.

In examples, T-cell epitopes-based immunotherapy can lack common disadvantages, providing desensitization avoiding secondary effects, because those epitopes are too short to induce cross-linking to allergen-specific lgE on basophils or mast cells, like CPE can do. In examples, approaches described herein can be based on experimental results that demonstrated that tolerance against a complete allergen can be induced using small allergen-derived peptides, which are recognized by allergen specific T cells. In specific examples, cocktails of defined epitopes or chimeric protein arrangements including the target epitopes can elicit convenient humoral and/or cellular immune responses.

Identification of potential T-cell epitopes in the food allergens is essential for development of peptide-based immunotherapy.

In examples, in-silica MHC class 11 "de novo" binding prediction of epitopes can represent a significant advantage to guide the screening in in-vivo assays (e.g., thereby reducing expenses; etc.).

In embodiments, we developed the following workflow to predict de novo epitopes against one or more food allergies, such as based in pathogen/allergen agent and/or based in bacterial species and/or suitable microorganism taxa, which could potentially be microbiota species present in mouth, gut, vaginal, skin, genitals, nose, and/or any suitable body sites (e.g., healthy sites; unhealthy sites; etc.) in relation to the microbiome.

A strategy to identify T-cell epitopes can include first (and/or at any suitable time and frequency) predicting HLA binding peptides by in-silica methods (and/or other suitable approaches). In specific examples, short length peptides (8-20 amino acids), are predicted with the support of methods that include neural networks (ANN), support vector machine (SVM), matrix based (MB) algorithms, and/or their combination, and/or any suitable artificial intelligence approach and/or analytical technique, including any one or more supervised learning (e.g., using logistic regression, using back propagation neural networks, using random forests, decision trees, etc.), unsupervised learning (e.g., using an Apriori algorithm, using K-means clustering), semi-supervised learning, a deep learning algorithm, (e.g., neural networks, a restricted Boltzmann machine, a deep belief network method, a convolutional neural network method, a recurrent neural network method, stacked auto-encoder method, etc.), reinforcement learning (e.g., using a Q-learning algorithm, using temporal difference learning), regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organization map, etc.), a regularization method (e.g., ridge regression least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naive Bayes, averaged one-dependence estimators, Bayesian belief network, etc.), a kernel method (e.g., a support vector machine, a radial basis function, a linear discriminant analysis, etc.), a clustering method (e.g., k-means clustering, expectation maximization, etc.), an associated rule learning algorithm (e.g., an Aprioiri algorithm, and Eclat algorithm, etc.), an artificial neural network method (e.g., a Perceptron method, a back-propagation method, a Hopfield network method, a self-organizing map method, a learning vector quantization method, etc.), an ensemble method (e.g., boosting, bootstrapped aggregation, AdaBoost, stacked generalization, gradient boosting machine method, random forest method, etc.). Additionally or alternatively, any suitable portions of embodiments of methods and/or systems can include, apply employ, perform, use, be based on, and/or otherwise be associated with artificial intelligence approaches and/or analytical techniques described herein.

Embodiments can leverage approaches described above and/or herein to predict peptides which can bind to human leukocyte antigen (HLA) class II, that correspond to the human version of the major histocompatibility complex (MHC). HLA complex can present those peptide antigens as epitopes.

In embodiments, then (and/or at any suitable time and frequency) the process workflow (e.g., portions of embodiments of a method, etc.) can include at least one or more of: First (and/or at any suitable time and frequency), embodiments can include identifying the microbiota which is present in the healthy (e.g., healthy samples; healthy subjects; etc.) that can be related with the one or more diseases (e.g., microorganism-related condition(s)). At the same time (and/or at any suitable time and frequency), embodiments can include identifying food allergens, proteins or agents.

Then (and/or at any suitable time and frequency), embodiments can include associating the allergens with some microbiota through the amino acid and/or genomic sequences. At the same time (and/or at any suitable time and frequency), embodiments can include obtaining a preliminary group of de novo epitopes, such as obtained through epitope prediction methods. In specific examples, the preliminary group of de novo epitopes are filtered, where repetitive sequences of epitopes are removed, such as based on analyzing the proteomes of the microbiome. In specific examples, with those filtered epitopes, a new database(s) can be made.

In specific examples, each epitope from the database(s) is correlated with proteome sequences obtained from an inversely-correlated organism proteome database, such as through local pairwise alignment tools (and/or other suitable tools and/or approaches) in order to find "de novo" predicted epitopes in those proteomes. In specific examples, what can be considered as "common epitopes" can be based on the predicted epitopes satisfying the following criteria:

1. Alignments having more than 60% identity and 90% similarity*.
2. Alignments having 90% identity and more than 8 similar amino acids*. Where "match" is the local similarity of an amino acid position in a pairwise alignment.

However, any suitable criteria (e.g., any suitable percent identity, percent matches, number of matches, any suitable percent similarity such as 50% similarity, etc.) can be used.

In variations, the common epitopes can be grouped, by agent, identity and/or MHC allele best affinity. However, a decrease of affinity can also considered, depending of the application of the epitope, considering that decreasing affinity, can involve a low sensitization against the allergen, or a better immune response.

In embodiments, to classify "common epitopes" according their affinity to the receptor, the database(s) can be tested using filtered de novo epitopes against a protein receptor class 11 structure, using molecular docking simulations, but any suitable simulations and/or processes can additionally or alternatively be performed.

In the next stage (and/or at any suitable time and frequency), in a variation to improve the affinity of epitopes for the MHC receptor, it is also possible to subject the best epitopes to a reengineering, which means that every (and/or any suitable number and type of) amino acid can be mutated in-silica, such as by other 22 proteinogenic amino acids (e.g., Alanine, Arginine, Asparagine, Aspartic acid, Cysteine, Glutamic-acid, Glutamine, Glycine, Histidine, Isoleucine, Leucine, Lysine, Methionine, Phenylalanine, Proline, Serine, Threonine, Tryptophan, Tyrosine, Valine, Selenocysteine, and Pyrrolysine). In examples, those new epitopes obtained by reengineering can be tested by docking and/or other suitable techniques, and then classified according their energy of binding to the receptor, such as where in this way, it is possible to obtain new epitopes with a better affinity to the receptor.

In specific examples, a de-nova list of epitopes are then obtained which are final candidates to be used as preventive, treatment and/or therapeutics and/or diagnostics for one or more diseases (e.g., microorganism-related conditions, autoimmune conditions, etc.).

Accordingly in specific examples, a general view of the workflow employed to identify "de novo" epitopes from proteins associated to food allergy, and then search them in proteins from organisms (and/or other suitable approaches described herein; etc.), can be described in FIG. 1.

Figure 2:
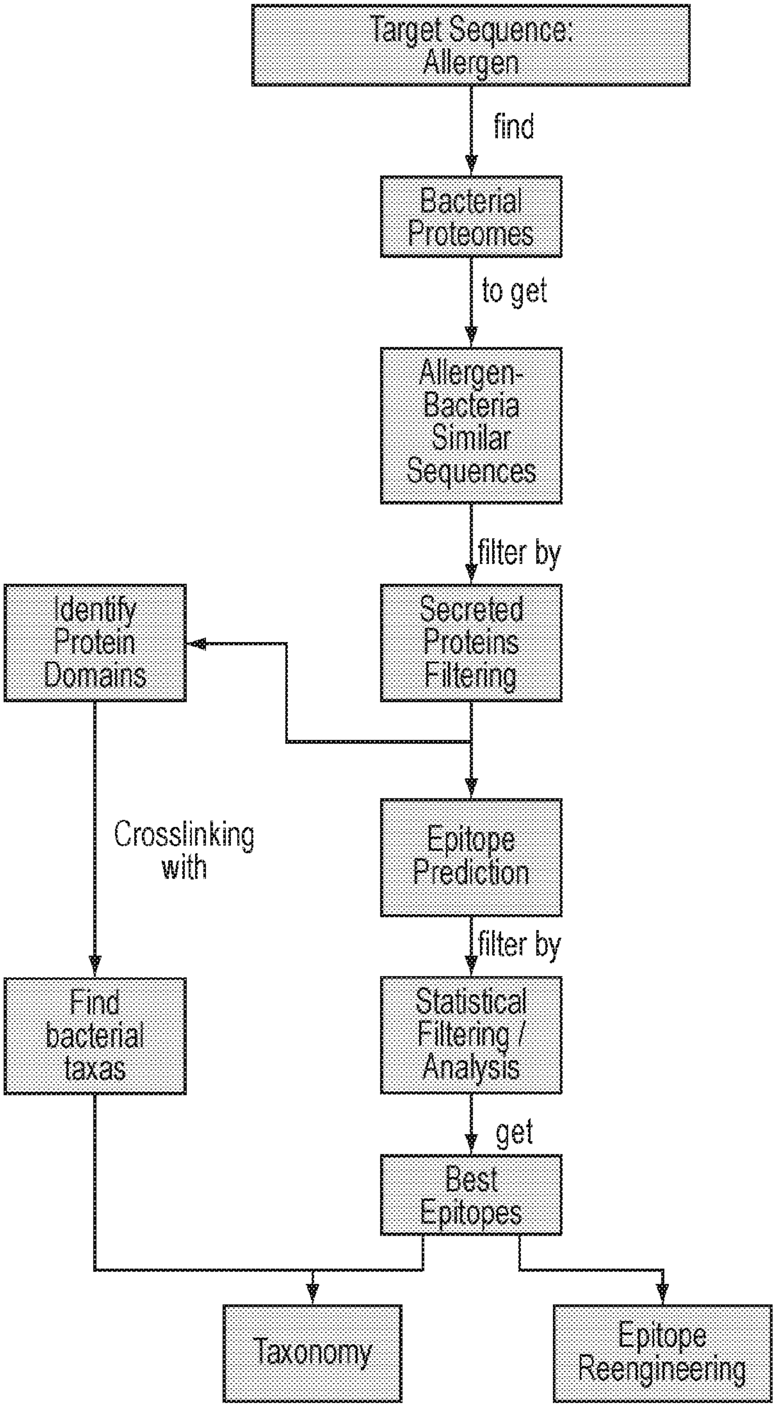
FIG. 2 illustrates a specific example of a complementary workflow, including alternative filtering options, employed to identify "de novo" epitopes from allergen proteins associated to a particular condition.

Additionally or alternatively, other in-silica methods used as filtering methods associated with protein(s), as detection of secreted proteins, virulence factors, domain identification, statistical filtering, taxonomy filtering, and/or other suitable aspects can be used, such as in FIG. 2.

Figure 3:
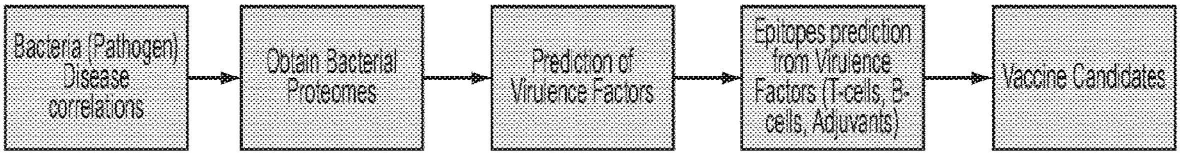
FIG. 3 illustrates a specific example of a complementary workflow, to describe a general process of epitopes prediction methods from virulence factors.

Additionally or alternatively, epitopes prediction can be applied from virulence factors (similarly as allergen) to describe potential vaccine candidates, to diagnostic, treatment or any similar therapeutics application which can be used as the scheme shown in FIG. 3.

Embodiments can include the use of predicted epitopes from any strains of bacteria and/or archaea species and/or reengineered ones, and/or other suitable microorganisms, in different products for the diagnostics, treatment and/or prevention and/or suitable conditions described herein, such as based on approaches described herein.

Embodiments can include therapeutic compositions including one or more epitopes described herein, such as epitopes derived from microorganisms described herein and/or other suitable microorganisms, such as for use in diagnostics, therapeutics, and/or other suitable applications, such as in relation to one or more conditions (e.g. Asthma, Bronchitis, Cancer, Graves disease, Hashimoto's thyroiditis, Hypothyroidism, Lupus, Lyme Disease, Migraine, Multiple Sclerosis, Osteoarthritis, Rheumatoid Arthritis, Sinusitis, Strep throat, Celiac disease, Crohn's disease, Irritable Bowel Syndrome, Ulcerative Colitis, Yeast infection, Acne, Eczema, Psoriasis, Rosacea, Dental decay, Ectodermal dysplasia, Gingivitis, Periodontal disease, Sjogren's syndrome, Cold/cough, Diarrhea, Dizziness, Fever, Headache, Insomnia, Migraine, Muscle aches, Rash or other where virus, bacteria or some external agent is related with) described herein, such as based on approaches described herein. Additionally or alternatively, embodiments (e.g., of the method, of diagnostics, of therapeutic compositions, etc.) can include, be for, be performed for, apply, correspond to, be diagnostic of (e.g., for diagnosing, etc.), be therapeutic of (e.g., therapeutic composition including epitopes therapeutic of, etc.), and/or otherwise be associated with one or more conditions, including any one or more of: diseases, symptoms, causes (e.g., triggers, etc.), disorders, associated risk (e.g., propensity scores, etc.), associated severity, behaviors (e.g., caffeine consumption, habits, diets, etc.), and/or any other suitable aspects associated with conditions. Conditions can include one or more disease-related conditions, which can include any one or more of: gastrointestinal-related conditions (e.g., irritable bowel syndrome, inflammatory bowel disease, ulcerative colitis, celiac disease, Crohn's disease, bloating, hemorrhoidal disease, constipation, reflux, bloody stool, diarrhea, etc.); allergy-related conditions (e.g., allergies and/or intolerance associated with wheat, gluten, dairy, soy, peanut, shellfish, tree nut, egg, etc.); skin-related conditions (e.g., acne, dermatomyositis, eczema, rosacea, dry skin, psoriasis, dandruff, photosensitivity, etc.); locomotor-related conditions (e.g., gout, rheumatoid arthritis, osteoarthritis, reactive arthritis, multiple sclerosis, etc.); autoimmune-related conditions (e.g., Sprue, AIDS, Sjogren's, Lupus, etc.), endocrine-related conditions (e.g., Hashimoto's thyroiditis, metabolic disease, etc.), communication-related conditions, sleep-related conditions, metabolic-related conditions, weight-related conditions, pain-related conditions, genetic-related conditions, chronic disease, and/or any other suitable type of disease-related conditions. Additionally or alternatively, microorganism-related conditions can include one or more human behavior conditions which can include any one or more of: caffeine consumption, alcohol consumption, other food item consumption, dietary supplement consumption, probiotic-related behaviors (e.g., consumption, avoidance, etc.), other dietary behaviors, habitue behaviors (e.g., smoking; exercise conditions such as low, moderate, and/or extreme exercise conditions; etc.), menopause, other biological processes, social behavior, other behaviors, and/or any other suitable human behavior conditions. Conditions can be associated with any suitable phenotypes (e.g., phenotypes measurable for a human, animal, plant, fungi body, etc.).

Embodiments can include a method for diagnostics and/or therapeutic compositions using "de novo" predicted epitopes and/or reengineered ones, such as derived from suitable microorganism for the treatment and/or prevention of suitable conditions described herein, such as based on approaches described herein.

Embodiments can include a method (e.g., a workflow) to identify "de novo" epitopes and/or reengineered ones from proteins belonging to one or more pathogens (e.g., described herein; other suitable microorganisms), and/or searching them in inversely-associated bacteria, such as to propose them as new epitope-based vaccines and/or suitable therapeutic compositions, intended to trigger an immune response, and/or for diagnostics, therapeutics, and/or prevention of any one or more conditions described herein, such as based on approaches described herein.

Embodiments can include a method (e.g., a workflow) to identify "de novo" virulence factors and/or epitopes and/or reengineered ones, belonging to one or more pathogens (e.g., described herein; other suitable microorganisms), propose them as new epitope-based vaccines, adjuvants and/or suitable therapeutic compositions, intended to trigger an immune response, and/or for diagnostics, therapeutics, and/or prevention of any one or more conditions described herein, such as based on approaches described herein.

Embodiments can include a method for identifying epitopes from non-pathogenic microorganisms (e.g., any suitable type of microorganisms, virus, bacteria, archaea, etc.), such as based off of epitopes derived from pathogenic microorganisms or agents that produce an immunological response; such as finding non-pathogenic microorganism epitopes that are similar, reengineered, and/or analogous to pathogenic microorganism epitopes; such as for facilitating improved safety in relation to epitope usage in diagnostics and/or therapeutics; such as based on using approaches described herein.

Embodiments can include one or more therapeutic compositions including one or more epitopes determined based on approaches described herein.

Embodiments can include the use of predicted epitopes from allergens and/or reengineered ones, and/or other suitable microorganisms, in different products for the diagnostics, treatment and/or prevention of allergy and/or suitable conditions described herein, such as based on approaches described herein.

Embodiments can include therapeutic compositions including one or more epitopes described herein, such as epitopes derived from microorganisms described herein and/or other suitable microorganisms, such as for use in diagnostics, therapeutics, and/or other suitable applications, such as in relation to one or more conditions (e.g., cancer, warts, etc.) described herein, such as based on approaches described herein.

Embodiments can include a method for diagnostics and/or therapeutic compositions using "de novo" predicted epitopes and/or reengineered ones, such as derived from microorganisms described herein and/or other suitable microorganism for the treatment and/or prevention of allergy and/or suitable conditions described herein, such as based on approaches described herein.

Embodiments can include a method (e.g., a workflow) to identify "de novo" epitopes and/or reengineered ones from proteins belonging to one or more pathogens (e.g., described herein; other suitable microorganisms), and/or searching them in inversely-associated bacteria, such as to propose them as new epitope-based vaccines and/or suitable therapeutic compositions, intended to trigger an immune response, and/or for diagnostics, therapeutics, and/or prevention of any one or more conditions described herein, such as based on approaches described herein.

Embodiments can include a method for identifying epitopes from non-pathogenic microorganisms (e.g., any suitable type of microorganisms, virus, bacteria, archaea, etc.), such as based off of epitopes derived from pathogenic microorganisms, such as finding non-pathogenic microorganism epitopes that are similar, reengineered, and/or analogous to pathogenic microorganism epitopes, such as for facilitating improved safety in relation to epitope usage in diagnostics and/or therapeutics, such as based on using approaches described herein.

Embodiments can include one or more therapeutic compositions including one or more epitopes determined based on approaches described herein.

Embodiments can include a method (e.g., workflow, etc.) to predict T-cell epitopes "de novo" from known allergens, and/or then identify them in mentioned microorganisms, particularly applied to peanut allergy. Here, we used the evidence obtained in a previous submission (U.S. App. No. 62/434,917), which included at least disclosure of high and low abundance of several microorganisms in individuals with peanuts allergy. However, any suitable criteria of association between individuals and microbiome components for peanut allergy can be used.

Embodiments can function to include, perform, and/or be associated with in-silica MHC class II "de novo" binding prediction of epitopes, which can represent a significant advantage (e.g., reduced expenses, etc.) over in-vivo assays.

*Clostridia*-containing microbiota can confer food allergy-protective capacity to germ-free mice. Embodiments can include determining, using, and/or otherwise being associated with proteins from *Clostridia* and/or other microorganisms present in individuals (e.g., any suitable microorganism taxa, etc.) who do not have peanuts allergy may have epitopes in common with peanuts allergen proteins, which could explain the protective effect of *Clostridia.*

Peanut allergens can share important part of their sequences with other vegetal species, or those results of dietary habits, which can be potentially allergenic. Embodiments can include determining, using, and/or otherwise being associated with vegetable species that describe suitable similarity with peanut allergy, and might be a cause of allergy.

In specific examples, some of the bacterial proteins where epitopes in common with allergens are found, including nitronate monooxygenase and pyruvate phosphate dikinase, which are proteins related with short-chain fatty acids metabolism. In specific examples, those proteins showed matches with Ara h 14 and Ara h 15, proteins from allergens involved in oil and fatty acids metabolism.

In an embodiment, the development of de novo (new) epitope can be followed the following steps.

Obtaining Allergen Proteins (Performable at any Time and Frequency):

In examples, the method can include determining one or more allergen proteins, such as from academic sources (e.g., literature, etc.), databases, and/or other suitable sources. Allergen proteins from *Arachis hypogaea* (peanut) described to date have been classified under 17 types. However, only 15 have been described in literature and validated (Ara h 1-15, Table 1). In this example, Ara h sequences from Uniprot database were clustered (with 90% of identity) to obtain only one representative sequence for each Ara h type; however clustering and/or other suitable approach can be performed using any suitable identity threshold and/or any suitable condition to obtain one or more representative sequences.

TABLE 1

Examples of Peanuts allergen proteins (e.g., evaluated using approaches described herein; etc.)

| Protein | Type* |
|---|---|
| Ara h 1 | Cupin (Vicillin-type, 7S globulin) |
| Ara h 2 | Conglutin (2S albumin) |

TABLE 1-continued

| Examples of Peanuts allergen proteins (e.g., evaluated using approaches described herein; etc.) | |
|---|---|
| Protein | Type* |
| Ara h 3 | Cupin (Legumin-type, 11S globulin, Glycinin) |
| Ara h 4 | renamed to Ara h 3.02, number not available for future submissions |
| Ara h 5 | Profilin |
| Ara h 6 | Conglutin (2S albumin) |
| Ara h 7 | Conglutin (2S albumin) |
| Ara h 8 | Pathogenesis-related protein, PR-10, Bet v 1 family member |
| Ara h 9 | Nonspecific lipid-transfer protein type 1 |
| Ara h 10 | 16 kDa oleosin |
| Ara h 11 | 14 kDa oleosin |
| Ara h 12 | Defensin |
| Ara h 13 | Defensin |
| Ara h 14 | Oleosin |
| Ara h 15 | Oleosin |
| Agglutinin | Not - arah type, but recognized as Allergen (Galactose binding) |

In embodiments, the method can include the following workflow to predict de nova epitopes from peanut allergens, and/or then, identify if those epitopes are present in gut microbiome (and/or present in any suitable microbiome associated with any body site including one or more of gut site, mouth site, nose site, genital site, skin site, etc.) from healthy and/or unhealthy patients (e.g., with or without peanut allergy).

In examples, the method can include identifying one or more T cell epitopes, such as through first (and/or at any suitable time and frequency, etc.) predicting one or more de nova HLA binding peptides by in-silica methods. As an example, we first (and/or at any suitable time and frequency) considered Ara-h allergens described in the Table I and processed under an Epitopes Prediction Pipeline, and obtaining lists of 15 mers predicted peptides (but any suitable peptides of any suitable size can be predicted). In examples, through this pipeline (and/or suitable approaches described herein, etc.), peptides can be predicted that bind human leukocyte antigen (HLA) class II, corresponding to the human counterpart of the major histocompatibility complex (MHC). Considering that HLA class 11 susceptibility varies typically between 9 and 20 amino acids, that range could be potentially included, such instead 15 mers length, but any suitable ranges and sizes can be used. Thus, HLA complex is able to present those peptide antigens as epitopes. The HLA alleles which have been described to provoke a higher incidence of peanut allergy were considered:

HLA-DRB1*O1:01, HLA-DRB1*03:01, HLA-DRB1*04:01, HLA-DRB1*04:05, HLA-DRB1*08:02, HLA-DRB1*09:01, HLA-DRB1*11:01, HLA-DRB1*12:01, HLA-DRB1*13:02, HLA-DRB1*15:01, HLA-DRB3*01:01, HLA-DRB3*02:02, HLA-DRB4*01:01, HLA-DRB5*01:01, HLA-DQA1*05:01/DQB1*02:01, HLA-DQA1*05:01/DQB1*03:01, HLA-DQA1*03:01/DQB1*03:02, HLA-DQA1*04:01/DQB1*04:02, HLA-DQA1*01:01/DQB1*05:01, HLA-DPA1*02:01/DPB1*01:01, HLA-DPA1*01:03/DPB1*02:01, HLA-DPA1*01/DPB1*04:01, HLA-DPA1*03:01/DPB1*04:02, HLA-DPA1*02:01/DPB1*05:01, HLA-DPA1*02:01/DPB1*14:01, HLA-DQA1*02:01/DQB1*06:02, HLA-DQA1*01:02/DQB1*06:02, HLA-DRB1*07:01.

However, any suitable criteria to do a particular group or selection of HLA alleles can be used.

In examples, the list of unique epitopes was obtained after discard duplicated epitopes. Then (and/or at any suitable time and frequency), to find those epitopes in proteomes from associated bacteria, each epitope was aligned against each protein sequence, using local pairwise alignment tools (but any suitable alignment tools and/or suitable tools can be used). In examples, a "common epitope" between epitopes from peanuts allergens and from bacteria proteomes are those that meet the following criteria:

a. Alignments having more than 70% identity and 90% similarity*.

b. Alignments having 90% identity and more than 11 similar amino acids*.

Where "match" is the local similarity of an amino acid position in a pairwise alignment.

However, any suitable criteria (e.g., any suitable percent identity, percent matches, number of matches, any suitable percent similarity such as 60% identity, 8 similar amino acids, etc.) can be used.

In examples, then (and/or at any suitable time and frequency), the method can include determining a first screening of"common epitopes" according their affinity to the receptor, such as by testing our database of filtered de nova epitopes against a protein receptor class ii structure, using molecular docking simulations, but any suitable simulations and/or processes can additionally or alternatively be performed. In specific examples, the epitopes can be reengineered to improve (and/or eventually decrease) the immune response against MHC class II receptors, such as mutating by the 20 proteinogenic amino acids (Alanine, Arginine, Asparagine, Aspartic acid, Cysteine, Glutamic acid, Glutamine, Glycine, Histidine, isoleucine, Leucine, Lysine, Methionine, Phenylalanine, Proline, Serine, Threonine, Tryptophan, Tyrosine, Valine) (and/or suitable amino acids). In examples, the new epitopes obtained by reengineering can be tested by docking and/or other suitable techniques, and/or then classified according to their energy of binding to the receptor (and/or using any suitable criteria). In examples, in this way, it is possible to obtain new epitopes with a better affinity to the receptor.

Figure 4:
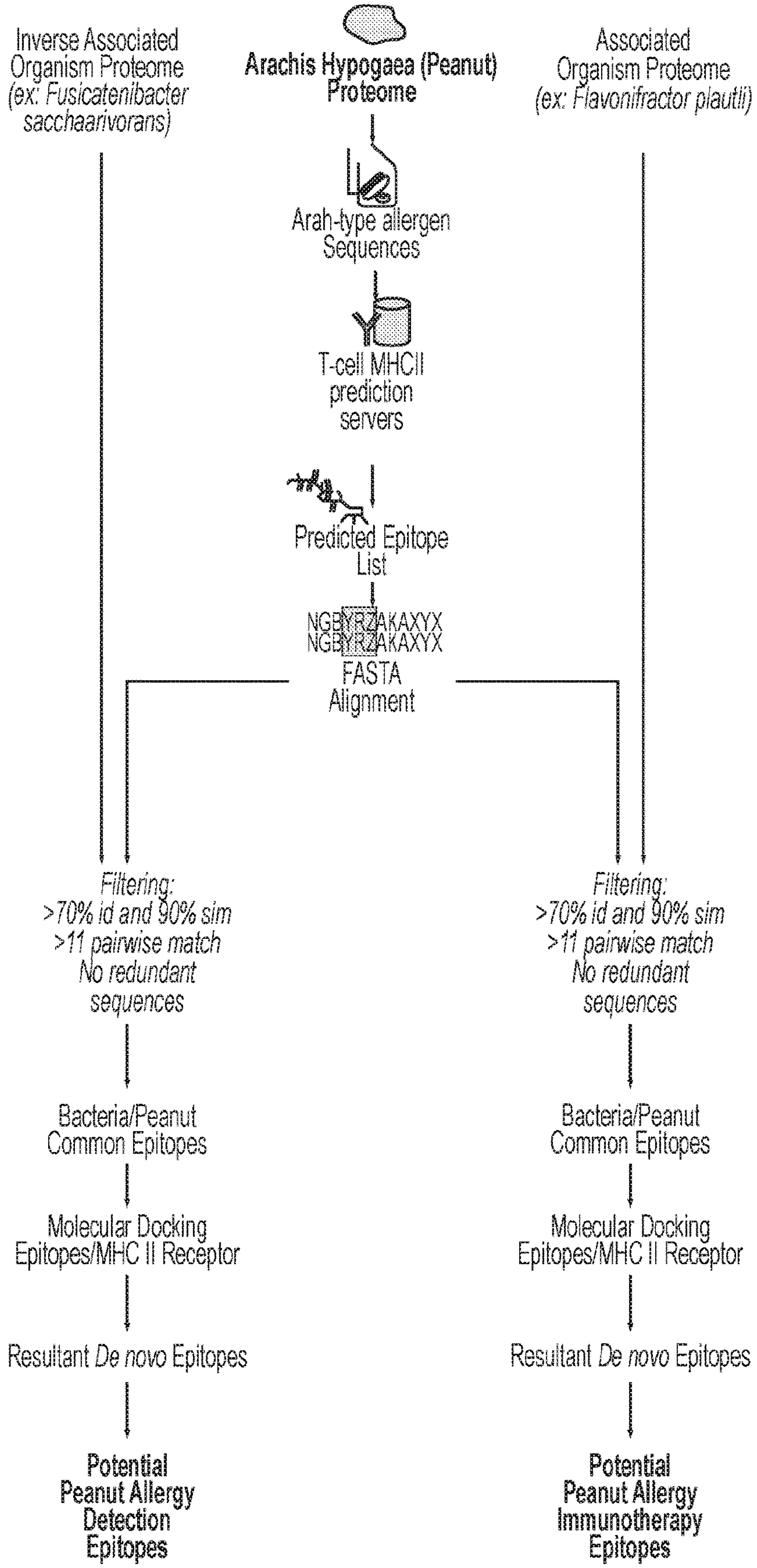
FIG. 4 illustrates a specific example of a general view of a workflow employed to identify "de novo" epitopes from allergen proteins associated with peanut allergy.

In examples, a general view of the workflow employed to identify "de novo" epitopes from pathogen proteins associated to a particular condition, and then search them in proteomes from associated organisms (and/or other suitable approaches), can be shown in FIG. 4.

Embodiments can include, use, and/or be associated with, Bacteria present in high abundance in individuals who do not have peanuts allergy contain proteins that could provide protection against that type of allergy, where, those bacteria, such as *F. saccharivorans*, might help individuals to not trigger allergy. Consequently, epitopes found in proteins from those inversely-correlated bacteria can be considered for an allergy diagnostic and/or treatment method, system, and/or therapeutic composition.

In embodiments, epitopes from directly associated microorganisms (e.g., whose abundance is high in presence of allergy) can be used as a peanuts allergy diagnostics method.

In embodiments, the epitopes identification platform can be used to detect bacterial proteins/bacteria and/or suitable microorganisms that can be related to food allergies.

Embodiments can include the integration of "de nova" epitopes or reengineered ones as a part of a new protein and their potential application for the treatment and/or prevention of peanut or any nut allergy.

Embodiments can include the use of de-nova predicted T-cell epitopes, and/or reengineered ones, belonging to bacteria that are augmented (directly associated) in individuals with peanut allergy: *Flavonifactor plautii, Lachnospira pectinoschiza, Dorea longicatena, Anaerostipes* sp. 5_1_63FAA, *Blautia* sp. SerB, *Die/ma fastidiosa, Barnesiella intestinihominis, Alistipes* sp. EBA6-25Gl2, *Anaerostipes* sp. 3_2_56FAA, *Bacteroides vulgatus, Eisenbergiella tayi, Kluyvera georgiana, Bacteroides clarus, Anaerotruncus Colihominis, Phascolarctobacterium faecium, Alistipes* sp. RMA 9912, *Flavonifractor plautii, Odoribacter splanchicus, Bacteroides fragilis, Bilophila* sp. 4_1_30, *Bacteroides* sp. D22, *Aldercreutzia equolifaceiens, Erysipelatoclostridium ramosum, Eggerthella* sp. HGA1, *Lactonifactor longoviformis, Gordonibacter pamelaeae, Blautia* sp. YHC-4, *Bacteroides massiliensis* in different products as a diagnostics and/or treatment method, system, and/or therapeutic composition of peanuts or any related food which contain one or more protein related with peanut allergen.

Embodiments can include the use of de-nova predicted T-cell epitopes, and/or reengineered ones, belonging to bacteria that are decreased (inversely associated) in individuals with peanut allergy, and thus including one or more of: *Fusicatenibacter saccharivorans, Lactobacillus* sp. BL302, *Lactobacillus crispatus, Faecalibacterium prausnitzii, Roseburia* sp. 11SE39, *Roseburia inulinivorans, Blautia luti, Alistipes* sp. NML05A004, *Collinsella aerofaciens, Haemophilus parainfluenzae, Dorea formicigenerans, Bacteroides thetaiotaomicron* in different products for treatment and/or prevention of peanuts and/or any nut allergy.

Embodiments can include the use of de-nova predicted T-cell epitopes, and/or reengineered ones, as the association of bacteria itself with allergen related with peanut including one or more of: *Ethanoligenens harbinense, Adlercreutzia equolifaciens, Alistipes* sp. EBA6-25Gl2, *Alistipes* sp. NML05A004, *Alistipes* sp. RMA 9912, *Anaerocolumna aminovalerica, Anaerocolumna cellulosilytica, Anaerocolumna jejuensis, Anaerocolumna xylanovorans, Anaerosalibacter massiliensis, Anaerostipes* sp. 3_2_56FAA, *Anaerostipes* sp. 5_1_63FAA, *Anaerotruncus rubiinfantis, Bacteroides clarus, Bacteroides massiliensis, Bacteroides ovatus, Bacteroides plebeius, Bacteroides* sp. D22, *Bacteroides stercoris, Bacteroides thetaiotaomicron, Bacteroides unmformis, Barnesiella intestinihominis, Bifidobacterium adolescentis, Bilophila* sp. 4_1_30, *Blautia caecimuris, Blautia coccoides, Blautia glucerasea, Blautia hansenii, Blautia hominis, Blautia hydrogenotrophica* CAG:147, *Blautia luti, Blautia marasmi, Blautia massiliensis, Blautia obeum, Blautia phocaeensis, Blautia producta, Blautia provencensis, Blautia* sp., *Blautia* sp. SerB, *Blautia* sp. YHC-4, *Butyrivibrio* cf. *fibrisolvens* EAT6, *Butyrivibrio crossotus* CAG:259, *Butyrivibrio fibrisolvens, Butyrivibrio hungatei, Butyrivibrio proteoclasticus, Butyrivibrio* sp., *Caproiciproducens galactitolivorans, Clostridia cluster*/Va, *Clostridia cluster* X/Va, *Clostridia cluster* X/Vb, *Clostridium difficile, Clostridium leptum, Collinsella aerofaciens, Coprococcus comes* CAG:19, *Coprococcus eutactus, Coprococcus eutactus* CAG:665, *Cysticercus cellulosi, Die/ma fastidiosa, Dorea formicigenerans, Dorea longicatena, Eggerthella* sp. HGA1, *Eisenbergiella tayi, Eubacterium aggregans, Eubacterium albensis, Eubacterium callanderi, Eubacterium dolichum* CAG:375, *Eubacterium eligens* CAG:72, *Eubacterium ha/Iii* CAG:12, *Eubacterium pectinii, Eubacterium rectale* CAG:36, *Eubacterium siraeum* CAG:80, *Eubacterium* sp., *Eubacterium ventriosum, Eubacterium xylanophilum, Faecalibacterium* sp., *Faecalicatena contorta, Faecalicatena fissicatena, Faecalicatena orotica, Flavonifractor* sp., *Fusicatenibacter saccharivorans, Gordonibacter pamelaeae, Haemophilus parainfluenzae, Helicobacter pylori, Hungate/la effluvii, Hungate/la hathewayi, Kluyvera georgiana, Lachnoclostridium edouardi, Lachnoclostridium pacaense, Lachnoclostridium phocaeense, Lachnoclostridium* sp., *Lachnoclostridium urinimassiliense, Lachnospira pectinoschiza, Lactobacillus crispatus, Lactobacillus* sp. BL302, *Odoribacter splanchnicus, Oscilibacter massiliensis, Peptostreptococcus anaerobius* CAG:621, *Peptostreptococcus glycinophilus, Peptostreptococcus* sp., *Phascolarctobacterium faecium, Prevotella tannerae, Pseudoflavonifractor phocaeensis, Pseudoflavonifractor* sp., *Roseburia cecicola, Roseburia intestinalis* CAG:13, *Roseburia* sp., *Roseburia* sp. 11SE39, *Ruminococcus gnavus, Ruminococcus obeum* CAG:39, *Ruminococcus* spp., *Sporobacter* sp., *Subdoligranulum variabile, Tissierella carlieri, Urmitella timonensis,* [*Clostridium*] *aerotolerans,* [*Clostridium*] *aldenense,* [*Clostridium*] *algidixylanolyticum,* [*Clostridium*] *aminophilum,* [*Clostridium*] *amygdalinum,* [*Clostridium*] *asparagiforme,* [*Clostridium*] *bolteae,* [*Clostridium*] *celerecrescens,* [*Clostridium*] *citroniae,* [*Clostridium*] *clostridioforme,* [*Clostridium*] *cocleatum,* [*Clostridium*] *fimetarium,* [*Clostridium*] *glycyrrhizinilyticum,* [*Clostridium*] *herbivorans,* [*Clostridium*] *hylemonae,* [*Clostridium*] *indolis,* [*Clostridium*] *innocuum,* [*Clostridium*] *lavalense,* [*Clostridium*] *methoxybenzovorans,* [*Clostridium*], *polysaccharolyticum,* [*Clostridium*] *populeti,* [*Clostridium*] *saccharogumia,* [*Clostridium*] *saccharolyticum,* [*Clostridium*] *scindens,* [*Clostridium*] *sphenoides,* [*Clostridium*] *symbiosum,* [*Clostridium*] *ultunense,* [*Clostridium*] *xylanolyticum,* [*Desulfotomaculum*] *guttoideum,* [*Eubacterium*] *cellulosolvens,* [*Eubacterium*] *eligens,* [*Eubacterium*] *ha/Iii,* [*Ruminococcus*] *gnavus,* [*Ruminococcus*] *gnavus* CAG:126, [*Ruminococcus*] *torques,* [*Ruminococcus*] *torques* CAG:61, *Cetitomaculum ruminis, Subdoligranulum variabile, Lactonifactor longoviformis, Clostridia cluster* X/Va, *Clostridia cluster* IV.

Embodiments can include a workflow to identify "de novo" epitopes or reengineered ones from proteins belonging to a pathogen, and search them in inversely-associated bacteria, to propose them as new epitope-based vaccines intended to trigger an immune response.

Embodiments can include, use, and/or otherwise be associated with additional or alternative species related with peanut, inoculated through a similarity by allergens:

Ara h1, Ara h2, Ara h3, Ara h4: *Anacardium occidentale, Bertholletia excelsa, Corylus avellana, Fagopyrum esculentum, Glycine max, Juglans nigra, Juglans regia, Sesamum indicum.*

Ara h5: *Ananas comosus, Apium graveolens, Arabidopsis thaliana, Arachis hypogaea, Betula verrucosa* (*Betula pendula*), *Capsicum annuum, Chenopodium album, Corylus avellana, Cucumis melo, Cynodon dactylon, Daucus carota, Glycine max, Helianthus annuus, Hevea brasiliensis, Litchi chinensis, Lycopersicon esculentum, Ma/us domestica, Mercurialis annua, Musa acuminata, Olea europea, Parietaria judaica, Phleum pratense, Prunus avium, Prunus persica, Pyrus communis, Triticum aestivum.*

Ara h6, Ara h7: *Ambrosia artemisiisfolia, Anacardium occidentale, Arachis hypogaea, Bertholletia excelsa, Brassica juncea, Brassica napus, Corylus avellana, Fagopyrum esculentum, Glycine max, Hevea brasiliensis, Hordeum vulgare, Juglans nigra, Juglans regia, Lycopersicon esculentum, Ma/us domestica, Oryza sativa, Parietaria judaica, Prunus armeniaca, Prunus avium, Prunus domestica, Prunus persica, Pyrus communis, Ricinus communis, Sesamum indicum, Sinapis alba, Triticum aestivum, Vitis vinifera, Zea mays.*

Ara h8: *Alnus glutinosa, Apium graveolens, Arachis hypogaea, Betula verrucosa (Betula pendula), Carpinus betulus, Castanea sativa, Corylus avellana, Daucus carota, Glycine max, Ma/us domestica, Petroselinum crispum, Phaseolus vulgaris, Prunus armeniaca, Prunus avium, Pyrus communis, Taraxacum officinale.*

TABLE 2

Additional or alternative information of each epitope, and which protein of bacteria was found:

| | EPI-TOPE | SEQUENCE_ID_PROTEOM | PRQTEOME | QUERY_ALIGN | SUBJECT_ALIGN | IDEN-TITY | SIMILI-TUDE | ALIGN | DESCRIPTION_SEQUENCE_ID_PROTEOME | Obtained from | Core (9mer) |
|---|---|---|---|---|---|---|---|---|---|---|---|
| 1 | GTIIGLAIATPVFTF | tr\|KOXJA7\|KOXJA7_9BACT | Barnesiella_intestini-hominis | TIIGLAIATPVFT | TMLGLAMATAPVFT | 0.714 | 0.929 | 9 + 14 | Uncharacterized_protien_OS = Barnesiella_intestinihominis_YIT_11860_GN = HMPREF9448_01764_PE = 4_SV = 1 | Arah14 | IGLAIATPV |
| 2 | LGTIIGLAIATPVFT | tr\|KOXJA7\|KOXJA7_9BACT | Barnesiella_intestini-hominis | TIIGLAIATPVFT | TMLGLAMATAPVFT | 0.714 | 0.929 | 9 + 14 | Uncharacterized_protien_OS = Barnesiella_intestinihominis_YIT_11860_GN = HMPREF9448_01764_PE = 4_SV = 1 | Arah14 | IGLAIATPV |
| 3 | TIIGLAIATPVFTFF | tr\|KOXJA7\|KOXJA7_9BACT | Barnesiella_intestini hominis | TIIGLAIATPVFT | TMLGLAMATAPVFT | 0.714 | 0.929 | 9 + 14 | _Uncharacterized_protien_OS = Barnesiella_intestinihominis_YIT_11860_GN = HMPREF9448_01764_PE = 4_SV = 1 | Arah14 | IGLAIATPV |
| 4 | AGVaLSRLVLRRNAL | tr\|A0A173WNPO\|A0A173WNPO_9ACTN | collinsella_aerofaciens_UP000095468 | AGVALSRLVLRRNA | ASVALARLVARRGA | 0.714 | 0.929 | 14 | _Nitronate_monooxygenese_OS = collinsella_aerofaciens_GN = ERS852381_00160_PE = 4_SV = 1 | Arah3 | LSRLVLRRN |
| 5 | CAGVALSRLVLRRNA | tr\|A0A173WNPO\|A0A173WNPO_9ACTN | collinsella_aerofaciens_UP000095468 | AGVALSRLVLRRNA | ASVALARLVARRGA | 0.714 | 0.929 | 14 | _Nitronate_monooxygenese_OS = collinsella_aerofaciens_GN = ERS852381_00160_PE = 4_SV = 1 | Arah3 | LSRLVLRRN |
| 6 | PAAITLALAAGGFLF | tr\|AOA173X9L7\|AQA173X9L7_9ACTN | collinsella_aerofaciens_UP000095468 | ITLALAaGGF | ISLALLAAGGF | 0.818 | 0.909 | 5 + 15 | _L-aspartate_transporter_OS = Collinsella_aerofaciens_GN = yveA_PE = 4_SV = 1 | Arah15 | ITLALAAGG |
| 7 | GVALSRLVLRRNALR | tr\|AOA173WNP0\|AOA173WNP0_9ACTN | collinsella_aerofaciens_UP000095468 | VALSRlvlrrHA | VALARLVARRGA | 0.75 | 0.917 | 12 | _Nitronate_monooxygenese_OS = collinsella_aerofaciens_GN = ERS852381_00160_PE = 4_SV = 1 | Arah3 | LVLRRNALR |
| 8 | VALSRLVLRSNALRR | tr\|A0A173WNP0\|AOA173WNP0_9ACTN | collinsella_aerofaciens_UP000095468 | VALSRlvlrrNA | VALARLVARRGA | 0.75 | 0.917 | 12 | _Nitronate_monooxygenese_OS = collinsella_aerofaciens_GN = ERS852381_00160_PE = 4_SV = 1 | Arah3 | IVLRRNALR |

TABLE 2-continued

Additional or alternative information of each epitope, and which protein of bacteria was found:

| | EPITOPE | SEQUENCE_ID_PROTEOM | PRQTEOME | QUERY_ALIGN | SUBJECT_ALIGN | IDENTITY | SIMILITUDE | ALIGN | DESCRIPTION_SEQUENCE_ID_PROTEOME | Obtained from | Core (9mer) |
|---|---|---|---|---|---|---|---|---|---|---|---|
| 9 | LLGILVLASVSATHA | tr\|F0HJV5\|F0HJV5_9ACTN | Eggerthella_sp._HGA1 | LLGILVLASVSA | LLGLLVIALVSA | 0.75 | 0.917 | 12 | _Putative_membrane protien_OS = Eggerthella_sp._HAGA1_GN = HMPR EF9404_3564_PE = 4_SV = 1 | Arah1 | ILVLASVSA |
| 10 | GNVASFLTSFSFEMK | tr\|B0N353\|B0N353_9FIRM | Erysipelato-clostridium_ramosum | GNVASFLTSFSF | GEVADFTSFSF | 0.75 | 0.917 | 6 - 15 | _DegT/DnrJ/EryC1/strS_aminotransferase_family_protien_OS = Erysipelato clostridium_ramosum_DSM_1403_GN = CLORAM_00871_PE = 3_ _SV = 1 | Agglutinin_LECG_ | FLTSFSFEM |
| 11 | TGNVASFLTSFSFEM | tr\|B0N353\|B0N353_9FIRM | Erysipelato-clostridium_ramosum | GNVASFLTSFSF | GEVADFTSFSF | 0.75 | 0.917 | 6 - 15 | _DegT/DnrJ/EryC1/strS_aminotransferase_family_protien_OS = Erysipelato clostridium_ramosum_DSM_1403_GN = CLORAM_00871_PE = 3_ _SV = 1 | Agglutinin_LECG_ | FLTSFSFEM |
| 12 | ANYAYNYSVVGGVAL | tr\|G9YM06\|353\|G9YM06_9FIRM | falvonii_factor_plautii | AYNYSVVGGVAL | AYGYAVVLVVAL | 0.75 | 0.917 | 12 | _Uncharacterized_protien_OS = falvoniifactor_plautii_ATCC_29863_GN = HMPREF0372_00521_PE = 4_SV = 1 | Arah8 | YNYSVVGGV |
| 13 | NYAYNYSVVGGVALP | tr\|G9YM06\|353\|G9YM06_9FIRM | falvonii_factor_plautii | AYNYSVVGGVAL | AYGYAYYLGVAL | 0.75 | 0.917 | 12 | _Uncharacterized_protien_OS = falvoniifactor_plautii_ATCC_29863_GN = HMPREF0372_00521_PE = 4_SV = 1 | Arah8 | YNYSVVGGV |
| 14 | EEQGAIVTVRGGLRI | tr\|A0A174PZ33\|A0A174PZ33_9FIRM | Fusicatenibacter_sacchari-vorans | QGAIVTVRGGL | QGILTVRGGM | 0.727 | 0.909 | 2 - 18 | _Pyruvate_phosphate_dikinase_OS = Fusicatenibacter_saccharivorans_GN = ppdX_PE = 4_SV = 1 | Arah3 | IVTVTGGLR |
| 15 | EQGAIVTVRGGLRIL | tr\|A0A174PZ33\|A0A174PZ33_9FIRM | Fusicatenibacter_sacchari-vorans | QGAIVTVRGGL | QGILTVRGGM | 0.727 | 0.909 | 2 - 18 | _Pyruvate_phosphate_dikinase_OS = Fusicatenibacter_saccharivorans_GN = ppdX_PE = 4_SV = 1 | Arah3 | IVTVTGGLR |
| 16 | QGAIVTVRGGLRILS | tr\|A0A174PZ33\|A0A174 | Fusicatenibacter_sacchari-vorans | QGAIVTVRGGL | QGILTVRGGM | 0.727 | 0.909 | | _Pyruvate_phosphate_dikinase_OS = Fusicateni | Arah3 | IVTVTGGLR |

TABLE 2-continued

Additional or alternative information of each epitope, and which protein of bacteria was found:

| EPI-TOPE | SEQUENCE_ ID_ PROTEOM | PRQTEOME | QUERY_ ALIGN | SUBJECT_ ALIGN | IDEN-TITY | SIMILI-TUDE | ALIGN | DESCRIPTION_ SEQUENCE_ID_ PROTEOME | Obtained from | Core (9mer) |
|---|---|---|---|---|---|---|---|---|---|---|
| | PZ33_ 9FIRM | | | | | | | bacter_ saccharivorans_ GN = ppdX_ PE = 4_SV = 1 | | |
| 17 FSGG CGVA AIAA LSW | tr\| A6NR8\| A6NR88_ 9FIRM | pseudo flavoni- fractor_ capillosus | FSGG CGVA A | FSGGC IGVSA | 0.8 | 0.9 | 5 + 14 | _Uncharacterized_ protien_OS = flavonifractor_ capillosus_ ATCC_29799_ GN = BACCAP_00713_ PE = 4_SV = 1 | Arah15 | GVAAI AALS |
| 18 AGGF LFSG GCGV AAI | tr\| A6NR8\| A6NR88_ 9FIRM | pseudo flavoni- fractor_ capillosus | GFL FSGG CGVA A | GLLFS GGGCG VSA | 0.769 | 0.923 | 8 + 14 | _Uncharacterized_ protien_OS = flavonifractor_ capillosus_ ATCC_29799_ GN = BACCAP_00713_ PE = 4_SV = 1 | Arah15 | FSGGC GVAA |
| 19 GFLF SGGC GVAA IAA | tr\| A6NR8\| A6NR88_ 9FIRM | pseudo flavoni- fractor_ capillosus | GFLF SGGC GVAA | GLLFS GGGCG VSA | 0.769 | 0.923 | 8 + 14 | _Uncharacterized_ protien_OS = flavonifractor_ capillosus_ ATCC_29799_ GN = BACCAP_ 00713_ PE = 4_SV = 1 | Arah15 | GCGV AAIAA |
| 20 GGFL FSGG CGVA AIA | tr\| A6NR8\| A6NR88_ 9FIRM | pseudo flavoni- fractor_ capillosus | GFL FSGG CGVA A | GLLFS GGGCG VSA | 0.769 | 0.923 | 8 + 14 | _Uncharacterized_ protien_OS = flavonifractor_ capillosus_ ATCC_29799_ GN = BACCAP_00713_ PE = 4_SV = 1 | Arah15 | DGGC GVAAI |
| 21 LFSG GCGV AAIA ALS | tr\| A6NR8 8\|A6NR6 8_9FIRM | pseudo flavoni- fractor_ capillosus | LFSGG C GVAA | LFSGG CIGYS A | 0.818 | 0.909 | 6 + 14 | _Uncharacterized_ protien_OS = flavonifractor_ capillosus_ ATCC_29799_ GN = BACCAP_00713_ PE = 4_SV = 1 | Arah15 | CGVA AIAAL |
| 22 FLFS GGC GVAA IAAL | tr\| A6NR8 8\|A6NR6 8_9FIRM | pseudo flavoni- fractor_ capillosus | FLFSG GC GVAA | LLFSG GCIGV SA | 0.75 | 0.917 | 7 + 14 | _Uncharacterized_ protien_OS = flavonifractor_ capillosus_ ATCC_29799_ GN = BACCAP_00713_ PE = 4_SV = 1 | Arah15 | FSSGC GVaA |
| 23 LLGIL VLAS VSAT HA | tr\|A6NV M1\|A6NV M1_ 9FIRM | pseudo flavoni- fractor_ capillosus | LLGILV LASVS A | LLGLL VLVIV SA | 0,75 | 0.917 | 12 | _Uncharacterized_ protien_OS = flavonifractor_ capillosus_ ATCC_29799_ GN = BACCAP_00713_ PE = 4_SV = 1 | Arah1 | ILV LAS VSA |
| 24 VFLT FFLLL AASS KK | tr\|A6NP V3\|A6NP V3_ 9FIRM | pseudo flavoni- fractor_ capillosus | VFLTF FLL LAA | VILTF FFLSL AA | 0.75 | 0.917 | 8 + 12 | _Uncharacterized_ protien_OS = flavonifractor_ capillosus_ ATCC_29799_ GN = BACCAP_00713_ PE = 4_SV = 1 | Agglutinin_ LECG_ | FLLLA ASSK |

Embodiments of the method can, however, include any other suitable blocks or steps configured to facilitate reception of biological samples from subjects, processing of biological samples from subjects, analyzing data derived from biological samples, and generating models that can be used to provide customized diagnostics and/or probiotic-based therapeutics according to specific microbiome compositions and/or functional features of subjects.

Embodiments of the method and/or system can include every combination and permutation of the various system components and the various method processes, including any variants (e.g., embodiments, variations, examples, specific examples, figures, etc.), where portions of embodiments of the method and/or processes described herein can be performed asynchronously (e.g., sequentially), concurrently (e.g., in parallel), or in any other suitable order by and/or using one or more instances, elements, components of, and/or other aspects of the system and/or other entities described herein.

Any of the variants described herein (e.g., embodiments, variations, examples, specific examples, figures, etc.) and/or any portion of the variants described herein can be additionally or alternatively combined, aggregated, excluded, used, performed serially, performed in parallel, and/or otherwise applied.

Portions of embodiments of the method and/or system can be embodied and/or implemented at least in part as a machine configured to receive a computer-readable medium storing computer-readable instructions. The instructions can be executed by computer-executable components that can be integrated with the system. The computer-readable medium can be stored on any suitable computer-readable media such as RAMs, ROMs, flash memory, EEPROMs, optical devices (CD or DVD), hard drives, floppy drives, or any suitable device. The computer-executable component can be a general or application specific processor, but any suitable dedicated hardware or hardware/firmware combination device can alternatively or additionally execute the instructions.

As a person skilled in the art will recognize from the previous detailed description and from the figures and claims, modifications and changes can be made to embodiments of the method, system, and/or variants without departing from the scope defined in the claims.

Figure 6:
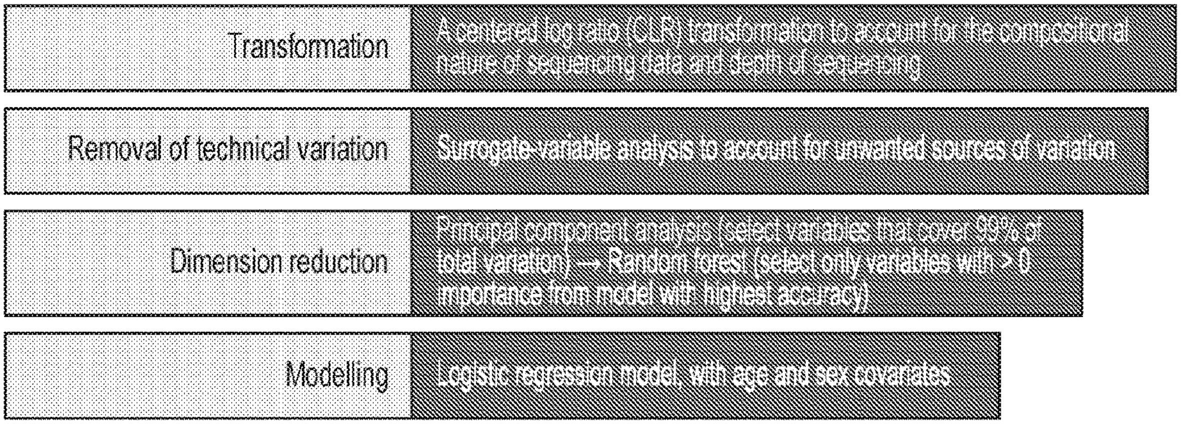
FIG. 6 illustrates the workflow of identifying the association between the taxonomic groups & functions and mental health conditions.

In another aspect, this disclosure relates to a discovery of correlations between neurological disorders and taxonomic groups and functions from the microbiome. In an embodiment, the correlation is between the taxonomic groups & functions and mental health conditions, including anxiety, attention deficit hyperactivity disorder (ADHD), autism spectrum disorder, chronic fatigue syndrome, depression, and stroke. In an embodiment, the discovery comprises four steps: 1. Transformation; 2. Removal of technical variation; 3, Dimension reduction; and 4. Modelling. A workflow of the procedure is illustrated in FIG. 6.

In an embodiment, the correlation is between the taxonomic groups & functions and anxiety. It was found that anxiety is associated with alterations in more than 20 gut microbiome metabolic functions, for example, carbohydrate metabolism. Gut bacteria dysregulation of carbohydrate metabolism pathway may produce a higher energy demand and consequently, less activity levels as a symptom of anxiety. The test results are shown below based on 5947 gut samples of anxiety patients and 1265 gut samples of healthy patients.

| Positively Associated Bacteria↑ | | Negatively Associated Bacteria↓ | |
|---|---|---|---|
| Species | Odds ratio | Species | Odds ratio |
| *Negativicoccus_succinicivorans* | 15.237 | *Anaerotruncus_colihominis* | 0.012 |
| *Flavonifractor_plautii* | 11.686 | *Murdochiella_asaccharolytica* | 0.014 |
| *Propionimicrobium_lymphophilum* | 4.054 | *Varibaculum_cambriense* | 0.018 |
| *Blautia_hydrogenotrophica* | 2.729 | *Lactobacillus_gasseri* | 0.021 |
| *Actinomyces_europaeus* | 2.510 | *Corynebacterium_pyruviciproducens* | 0.034 |
| *Corynebacterium_glaucum* | 2.254 | *Anaerococcus_senegaiensis* | 0.040 |
| *Peptoniphilus_duerdenii* | 2.085 | *Anaerococcus_octavius* | 0.057 |
| *Corynebacterium_imitans* | 2.057 | *Parabacteroides_gordonii* | 0.105 |
| *Lactobacillus_crispatus* | 1.764 | *Eggerthella_lenta* | 0.143 |
| *Finegoldia_magna* | 1.726 | *Corynebacterium_appendicis* | 0.177 |
| *Blautia_faecis* | 1.375 | *Corynebacterium_jeikeium* | 0.243 |
| *Prevoteila_corporis* | 1.311 | *Mathanosphaera_stadtmanae* | 0.299 |
| *Bacteroides_fragilis* | 1.276 | *Facklamia_ignava* | 0.323 |
| *Atopobium_vaginae* | 1.251 | *Eremococcus_coleocola* | 0.394 |
| *Tyzzerelia_nexilis* | 1.153 | *Arthrobacter_cumminsii* | 0.500 |
| *Corynebacterium_aurimucosum* | 1.140 | *Brevibacterium_massiliense* | 0.530 |

Figure 5:
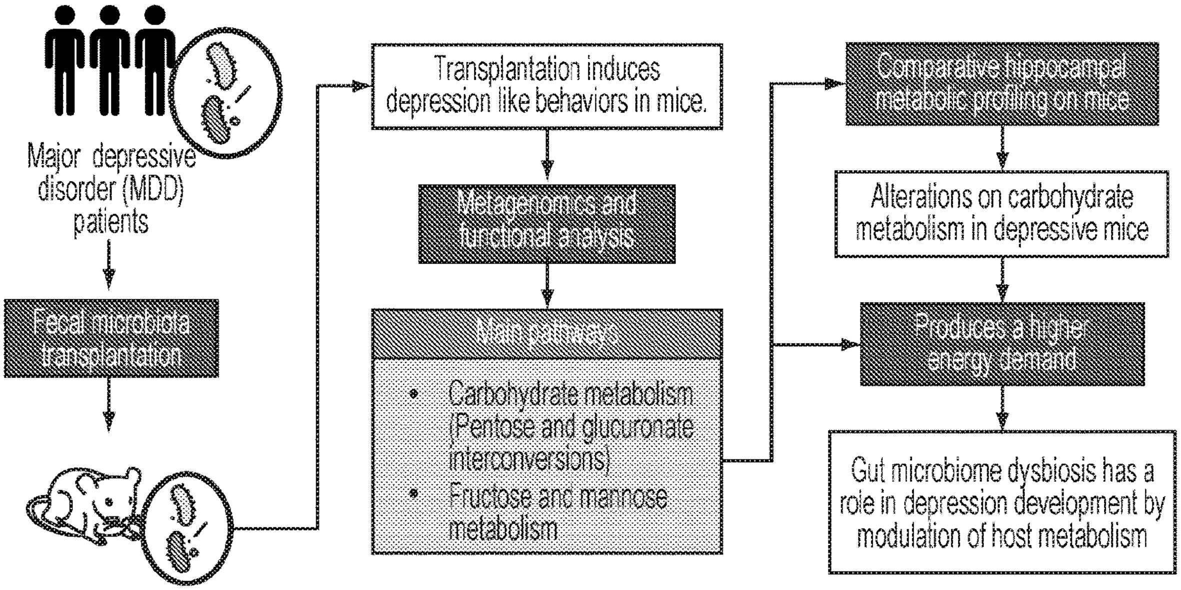
FIG. 5 illustrates the workflow of identifying the association between the host metabolism and major depressive disorder.

In an embodiment, the correlation is between the taxonomic groups & functions and depression. The workflow of identifying the host metabolism and major depressive disorder (MDD) is illustrated in FIG. 5. It was found that depression is associated with alterations in more than 20 gut microbiome metabolic functions, for example, sphingolipid metabolism. High-fat diet induces depression-like behavior in mice associated with changes in the microbiome that count affect sphingolipid metabolism. The test results are shown below based on 5767 gut samples of depression patients and 1265 gut samples of healthy patients.

| Positively Associated Bacteria↑ | | Negatively Associated Bacteria↓ | |
|---|---|---|---|
| Species | Odds ratio | Species | Odds ratio |
| *Flavonifractor_plautii* | 2.9293 | *Hoidemania_filiformis* | 0.0065 |
| *Mitsuokella_jalatudinii* | 2.2383 | *Anaerotruncus_colihominis* | 0.0110 |
| *Dielma_fastidiosa* | 2.1213 | *Slackia_exigua* | 0.0255 |
| *Parabacteroides_goldsteinii* | 2.1029 | *Pephoniphilus_obesi* | 0.0329 |
| *Bacteroides_nordii* | 1.5838 | *Eubacterium_coprostanoligenes* | 0.1682 |
| *Phascolarctobacterium_faecium* | 1.2091 | *Facklamia_hominis* | 0.1828 |
| *Bacteroides_fragilis* | 1.1541 | *Coprococcus_catus* | 0.2689 |
| *Parabacteroides_distasonis* | 1.1502 | *Coprobacilius_cateniformis* | 0.3541 |
| *Roseburia_inulinivorans* | 1.1418 | *Anaetostipes_caccae* | 0.3674 |
| *Prevoteila_bivia* | 1.1414 | *Eggerthelia_lenta* | 0.4838 |
| *Bilophila_wadsworthia* | 1.1396 | *Facklamia_ignava* | 0.5208 |
| *Finegoidia_magna* | 1.0750 | *Senegalimassilla_anaerobia* | 0.5259 |
| *Erysipelatoclostridium_ramosum* | 1.0657 | *Phascolarctobacterium_succinatutens* | 0.7293 |
| *Escherichia_coli* | 1.0254 | *Dorea_iongicatena* | 0.7569 |
| *Bacteroides_dorei* | 1.0127 | *Catenibacterium_mitsuokai* | 0.8569 |
| *Prevoteila_corporis* | 1.0002 | *Tyzzerelia_nexilis* | 0.8837 |

TABLE 3

Specific example of microorganism taxa associations with depression condition and/or suitable neurological-related conditions (e.g., neurological disorders; etc.)

| Species | Estimate | Std_Error | z.value | Pr_z_ | oddsratio |
|---|---|---|---|---|---|
| *Lactococcus_raffinolactis* | 25.92625512 | 100.6593982 | 0.2575641776 | 0.7967432792 | 181814926552 |
| *Ruminococcus_gauveauli* | 24.70085812 | 15.82844129 | 1.560536358 | 0.118633185 | 53388335304 |
| *Lactonifactor_longoviformis* | 12.16837513 | 7.585223995 | 1.604220935 | 0.1086653617 | 192600.8379 |
| *Catabacter_hongkongensis* | 7.243905677 | 44.48459127 | 0.1628407831 | 0.8706437965 | 1399.549499 |
| *Ezakiella_peruensis* | 5.776784609 | 2.8770511462 | 2.007883657 | 0.0446556563 | 322.71985 |
| *Blautia_hydrogenotrophica* | 4.925477517 | 1.883166366 | 2.615529677 | 0.008908917899 | 137.7551063 |
| *Flavonifractor_plautii* | 1.074756929 | 0.3623787962 | 2.965838344 | 0.003018591092 | 2.929280791 |
| *Mitsuokelia_jalaludinii* | 0.8057207134 | 0.3460498335 | 2.328337238 | 0.01989420346 | 2.238309097 |
| *Dielma_fastidiosa* | 0.7520298809 | 3.31676003 | 0.2267362951 | 0.8206288026 | 2.121301639 |
| *Parabacteroides_goldsteinii* | 0.7433142975 | 0.377155426 | 1.970843441 | 0.04874178612 | 2.102893593 |
| *Bacteroides_nordii* | 0.4598274282 | 0.4161121775 | 1.105056408 | 0.2691351477 | 1.583800642 |
| *Phascolarctobacterium_faecium* | 0.1898497981 | 0.08631944639 | 2.199386188 | 0.02785047391 | 1.20906798 |
| *Bacteroides_fragilis* | 0.143319106 | 0.06989655104 | 2.050446035 | 0.04032092479 | 1.154098022 |
| *Parabacteroides_distasonis* | 0.1399064057 | 0.0644175361 | 2.171868316 | 0.0298655969 | 1.150166145 |
| *Roseburia_inulinivorans* | 0.1325807887 | 0.1334045184 | 0.9938253236 | 0.3203079152 | 1.141771255 |
| *Prevotella_bivia* | 0.1322498156 | 0.2044677207 | 0.6468004591 | 0.5177610952 | 1.141393422 |
| *Bilophila_wadsworthia* | 0.1306891544 | 0.1431310902 | 0.9130731434 | 0.3612040741 | 1.139613482 |
| *Finegoidia_magna* | 0.07234557142 | 0.04412224032 | 1.639662241 | 1.1010754141 | 1.075026778 |
| *Erysipelatoclostridium_ramosum* | 0.06365580729 | 0.7502243897 | 0.08484902406 | 0.9323814185 | 1.065725521 |
| *Escherichia_coli* | 0.02509884321 | 0.03218956316 | 0.7797199077 | 0.4355557583 | 1.025416471 |
| *Bacteroides_dorei* | 0.01259406637 | 0.01293352046 | 0.9737539296 | 0.330178733 | 1.012673706 |
| *Prevotella_corporis* | 0.0001784591323 | 0.07616242943 | 0.002343138653 | 0.9981304476 | 1.000178475 |
| *Ruminococcus_lastaris* | −0.002506467631 | 0.1852290938 | −0.01353171675 | 0.9892035816 | 0.9974966709 |
| *Prevotella_copri* | −0.006006660422 | 0.01006321154 | −0.5971135951 | 0.05504315417 | 0.9940091368 |
| *Faecalibacterium_prausnitzii* | −0.01555792055 | 0.01163830363 | −1.336785931 | 0.1812925339 | 0.9845624787 |
| *Bacteroides_caccae* | −0.02260762112 | 0.04209459773 | −0.5370670428 | 0.591221305 | 0.9776460162 |
| *Ruminococcus_bicirculans* | −0.03481920224 | 0.0450024059 | −0.7737186833 | 0.439097169 | 0.9657800113 |
| *Staphylococcus_aureus* | −0.05387622358 | 0.06751085759 | −0.7980379084 | 0.4248484919 | 0.9475493835 |
| *Akkermansia_muciniphilia* | −0.05939841805 | 0.03426110215 | −1.733698402 | 0.08297161019 | 0.9423312526 |
| *Collinselia_aerofaciens* | −0.08065078472 | 0.05458390385 | −1.477556185 | 0.1395266093 | 0.9225157918 |
| *Tyzzerelia_nexilis* | −0.1236303025 | 0.09618060088 | −1.259213138 | 0.2079533574 | 0.8837064845 |
| *Catenibacterium_mitsuokai* | −0.1544717347 | 0.1193189705 | −1.294611696 | 0.1954542156 | 0.8568677114 |
| *Dorea_longicatena* | −0.2785384278 | 0.09928248079 | −2.805514383 | 0.005023633931 | 0.7568891816 |
| *Phascolarctobacterium_ succinatutens* | −0.3156557789 | 0.1542750253 | −2.046058838 | 0.04075058215 | 0.729310451 |
| *Senegalimassilia_anaerobia* | −0.6425621752 | 0.4774957255 | −1.345691994 | 0.1784018693 | 0.5259431378 |
| *Facklamia_ignava* | −0.6522963828 | 0.5768918567 | −1.130708252 | 0.258177907 | 0.5208483352 |
| *Eggerthella_lenta* | −0.7261828301 | 0.6672543125 | −1.08831493 | 0.2764561019 | 0.483752034 |
| *Anaerostipes_caccae* | −1.001266482 | 0.7119086622 | −1.406453574 | 0.1595894814 | 0.3674139233 |
| *Coprobacillus_cateniformis* | −1.038157432 | 1.305326731 | −0.7953237436 | 0.4264252054 | 0.3541065784 |
| *Coprococcus_catus* | −1.313387739 | 0.3922019079 | −3.348754078 | 0.0008117581281 | 0.2689075231 |
| *Facklamia_hominis* | −1.699317894 | 2.844072339 | −0.5974946104 | 0.5501772043 | 0.182808176 |
| *Eubacterium_coprostanoligenes* | −1.782653987 | 3.027447456 | −0.5888306942 | 0.5559748533 | 0.1681911771 |
| *Peptoniphilus_obesi* | −3.412858743 | 2.83962237 | −1.201870634 | 0.2294136537 | 0.03294687897 |
| *Slackia_exigua* | −3.668734786 | 9.101934173 | −0.4030719972 | 0.6868952602 | 0.02550872354 |
| *Anaerotruncus_colihominis* | −4.510705012 | 3.990003657 | −1.130501473 | 0.258264978 | 0.01099070886 |
| *Holdemania_filiformis* | −6.036662008 | 5.425738426 | −0.9282906055 | 0.3532568459 | 0.006495393741 |
| *Mucispirillum_schaedieri* | −6217.437082 | 186413.6539 | −0.03335290604 | 0.9733931643 | 0 |
| *Dysgonomonas_gadei* | −3902.892997 | 8127638.917 | −0.000480200097 | 0.9996168558 | 0 |

TABLE 4

Specific examples of microorganism taxa associations with anxiety conditions and/or suitable neurological-related conditions (e.g., neurological disorders; etc.)

| Species | Estimate | Std_Error | z.value | Pr_z_ | odds ratio |
|---|---|---|---|---|---|
| *Corynebacterium_tuscaniense* | 28.88700848 | 33.33390603 | 0.866595366 | 0.386163754 | 3.51E+12 |
| *Lactobacillus_rhamnosus* | 21.11387021 | 10.79718117 | 1.955498373 | 0.050524275 | 1477873708 |
| *Peptoniphilus_obesi* | 19.99180686 | 16.37166267 | 1.221122574 | 0.222039614 | 481206407.3 |
| *Actinomyces_neuii* | 19.00186185 | 10.04658753 | 1.891374738 | 0.058574338 | 178814918.6 |
| *Dielma_fastidiosa* | 11.73565119 | 6.640134109 | 1.767381652 | 0.077164334 | 124947.7829 |
| *Granulicateila_elegans* | 9.243940721 | 23.72739094 | 0.38958943 | 0.696840169 | 10341.71216 |
| *Ezaliella_peruensis* | 8.973880479 | 8.793483021 | 1.020514904 | 0.307484325 | 7894.175426 |
| *Dermabacter_hominis* | 6.507886973 | 23.12230257 | 0.28145497 | 0.778361461 | 670.4083292 |
| *Atopobium_parvulum* | 6.411615724 | 39.99441753 | 0.0160312767 | 0.872634703 | 608.8766631 |
| *Streptococcus_gordonii* | 5.614561356 | 18.19154593 | 0.308635746 | 0.757598626 | 274.392992 |
| *Porphyromonas_uenonis* | 5.120162121 | 3.466553628 | 1.477018004 | 0.139670811 | 167.3625004 |
| *Pseudoclavibacter_bifida* | 4.577686684 | 8.237756448 | 0.555695803 | 0.578418826 | 97.28907331 |
| *Prevotella_bergensis* | 4.520988154 | 7.946104768 | 0.568956525 | 0.569385644 | 91.92639055 |
| *Corynebacterium_urealyticum* | 4.186035977 | 3.47752236 | 1.203740924 | 0.22868973 | 65.76159316 |
| *Lactobacillus_vaginalis* | 3.258756064 | 1.269263358 | 2.567438857 | 0.010245286 | 26.01715334 |
| *Negativicoccus_succinicivorans* | 2.723738379 | 20.62614794 | 0.132052693 | 0.894942614 | 15.23717826 |
| *Flavonifractor_plautii* | 2.45841356 | 0.951815394 | 2.582868038 | 0.009798279 | 11.68625728 |
| *Propionimicrobium_lymphophilum* | 1.399646117 | 1.869289711 | 0.748758263 | 0.45400292 | 4.053765153 |
| *Blautia_hydrogenotrophica* | 1.003997618 | 3.254495371 | 0.308495636 | 0.757705221 | 2.729170231 |
| *Actinomyces_europaeus* | 0.920300088 | 15.85011759 | 0.058062666 | 0.953698712 | 2.51004351 |
| *Corynebacterium_glaucum* | 0.812810056 | 1.046147918 | 0.776955191 | 0.437185207 | 2.254233617 |
| *Peptoniphilus_duerdenii* | 0.734753727 | 3.532209304 | 0.208015342 | 0.835216988 | 2.084968457 |
| *Corynebacterium_imitans* | 0.721348024 | 1.18103059 | 0.610778443 | 0.541346267 | 2.057204504 |
| *Lactobacillus_crispatus* | 0.567502033 | 0.339907225 | 1.669579199 | 0.095002649 | 1.763855491 |
| *Finegoldia_magna* | 0.545610605 | 0.209036 | 2.610127468 | 0.009050849 | 1.725661759 |
| *Blautia_faecis* | 0.318525524 | 0.168852983 | 1.886407438 | 0.059240071 | 1.375098719 |
| *Prevotella_corporis* | 0.270961456 | 0.377306221 | 0.718147333 | 0.472666448 | 1.31122453 |
| *Bacteroides_fragills* | 0.243933672 | 0.074303722 | 3.282926689 | 0.001027354 | 1.276259676 |
| *Atopobium_vaginae* | 0.224288419 | 0.895985969 | 0.250325816 | 0.802335393 | 1.251431904 |
| *Tyzzerella_nexilis* | 0.142547638 | 0.289696869 | 0.492057918 | 0.6226784 | 1.153208016 |
| *Corynebacterium_aurimucosum* | 0.131034408 | 0.493668766 | 0.265429812 | 0.790678373 | 1.140007006 |
| *Bacteroides_dorei* | 0.04248077 | 0.021216196 | 2.002280182 | 0.045254606 | 1.043395991 |
| *Clostridium_aff* | 0.038898807 | 0.351616041 | 0.110628647 | 0.91191083 | 1.039665271 |
| *Facklamia_languida* | 0.017621502 | 1.215040383 | 0.014502812 | 0.988428836 | 1.017777676 |
| *Staphylococcus_aureus* | −0.011099298 | 0.09793054 | −0.113338476 | 0.909762214 | 0.988962072 |
| *Helcococcus_sueciensis* | −0.050673274 | 2.782691424 | −0.018210166 | 0.985471192 | 0.950589202 |
| *Holdemania_filiformis* | −0.082775902 | 11.98352498 | −0.006907475 | 0.994488676 | 0.920557419 |
| *Bilophiia_wadsworthia* | −0.09606582 | 0.428295059 | −0.224298221 | 0.822525261 | 0.908404223 |
| *Bacteroides_eggerthii* | −0.145278783 | 0.162593845 | −0.893507271 | 0.37158558 | 0.864781173 |
| *Porphyromonas_somerae* | −0.185986213 | 3.299746407 | −0.05636379 | 0.955052003 | 0.830285042 |
| Bacteroides_*caccae* | −0.285970853 | 0.163276025 | −1.75145648 | 0.079867311 | 0.751284514 |
| *Actinotignum_schaalii* | −0.542543077 | 1.079876653 | −0.502412082 | 0.615377682 | 0.581268161 |
| *Brevibacterium_massiliense* | −0.63525475 | 1.154210386 | −0.550380379 | 0.582058503 | 0.529800505 |
| *Arthrobacter_cumminsii* | −0.6932348 | 1.537019905 | −0.451025259 | 0.651971344 | 0.499956192 |
| *Eremococcus_coleocoia* | −0.931586328 | 1.316534356 | −0.707605027 | 0.47919057 | 0.393928315 |
| *Facklamia_ignava* | −1.12950589 | 1.96819152 | −0.573880071 | 1.56604896 | 0.32319291 |
| *Methanosphaera_stadtmanae* | −1.206170934 | 0.917098773 | −1.315202865 | 0.188441733 | 0.299341285 |
| *Corynebacterium_jeikeium* | −1.413836488 | 2.033967949 | −0.695112471 | 0.48698482 | 0.243208425 |
| *Corynebacterium_appendicis* | −1.732756774 | 3.850746158 | −0.449979485 | 0.652725233 | 0.17679635 |
| *Eggerthelia_lenta* | −1.944497166 | 1.839517495 | −1.057069134 | 0.290480037 | 0.14305914 |
| *Parabacteroides_gordonii* | −2.253239682 | 3.946613049 | −0.570929973 | 0.568047112 | 0.105058317 |
| *Anaerococcus_octavius* | −2.856759275 | 5.135458001 | −0.556281304 | 0.578018566 | 0.057454654 |
| *Anaerococcus_senegaiensis* | −3.211024441 | 2.506104603 | −1.281281091 | 0.200094952 | 0.040315291 |
| *Corynebacterium_pyruviciproducens* | −3.378515004 | 5.601837299 | −0.603108377 | 0.546436594 | 0.034098053 |
| *Lactobacillus_gasseri* | −3.879495278 | 3.262354057 | −1.189170523 | 0.234372572 | 0.020661251 |
| *Varibaculum_cambriense* | −4.014206957 | 1.589684729 | −2.525159161 | 0.01156459 | 0.018057269 |
| *Murdochiella_asaccharolytica* | −4.278966763 | 2.26930703 | −1.885583003 | 0.05935117 | 0.013856972 |
| *Anaerotruncus_colihominis* | −4.400890949 | 9.97406788 | −0.441233306 | 0.659044103 | 0.012266406 |
| *Parvimonas_micra* | −4.718913446 | 13.56532043 | −0.347865977 | 0.727940838 | 0.008924871 |
| *Oligeila_urethralis* | −14.32726797 | 2931.657258 | −0.004887088 | 0.996100683 | 5.99E−07 |
| *Veillonelia_montpellierensis* | −15.25074562 | 2384.342406 | −0.006396206 | 0.994896601 | 2.38E−07 |
| *Corynebacterium_frankenforstense* | −15.66630912 | 1573.347352 | −0.009957311 | 0.992055346 | 1.57E−07 |
| *Dolosigranulum_pigrum* | −15.7627745 | 1702.156777 | −0.009260472 | 0.992611318 | 1.43E−07 |
| *Corynebacterium_massiliense* | −15.96939252 | 2505.014981 | −0.006374969 | 0.994913545 | 1.16E−07 |
| *Flavobacterium_ceti* | −16.11439341 | 1233.22524 | −0.01306687 | 0.989574443 | 1.00E−07 |
| *Corynebacterium_negelii* | −16.19965849 | 1956.113512 | −0.008281553 | 0.993392352 | 9.22E−08 |
| *Bacteroides_bamesiae* | −16.32926677 | 4019.994832 | −0.004062012 | 0.996758992 | 8.10E−08 |
| *Actinomyces_georgiae* | −17.21723234 | 2933.245633 | −0.005869687 | 0.995316695 | 3.33E−08 |
| *Corynebacterium_matruchotii* | −17.8241343 | 2276.734553 | −0.007828815 | 0.993753573 | 1.82E−08 |
| *Meiothermus_silvanus* | −17.89826458 | 1664.703556 | −0.010751623 | 0.991421612 | 1.69E−08 |
| *Barnesielia_intestinihominis* | −19.37960413 | 1353.41733 | −0.014319016 | 0.988575469 | 3.83E−09 |
| *Solobacterium_moorei* | −19.66994142 | 25.52075749 | −0.770742852 | 0.440859367 | 2.87E−09 |
| *Dialister_pneumosintes* | −20.92348439 | 14.80371047 | −1.413394597 | 0.157539734 | 8.19E−10 |
| *Capnocytophaga_gingivalis* | −20.96264082 | 3460.310549 | −0.006058023 | 0.995166427 | 7.87E−10 |
| *Ignavigranum_rouffiae* | −25.37807617 | 2096.742142 | −0.012103575 | 0.99034298 | 9.52E−12 |

TABLE 4-continued

| Specific examples of microorganism taxa associations with anxiety conditions and/or suitable neurological-related conditions (e.g., neurological disorders; etc.) | | | | | |
|---|---|---|---|---|---|
| Species | Estimate | Std_Error | z.value | Pr_z_ | odds ratio |
| *Gardnerella_vaginalis* | −27.18677167 | 27.08955513 | −1.003588709 | 0.315576899 | 1.56E−12 |
| *Propionibacterium_avidum* | −151.8557409 | 101.7134754 | −1.492975639 | 0.135443564 | 1.12E−66 |

Administration:

The compounds/peptides of this invention may be administered orally, pulmonary, parenteral (intramuscular, intraperitoneal, intravenous (IV) or subcutaneous injection), inhalation (a fine powder composition), transdermal, intranasal, vaginal, rectal or tongue the administration route, and may be formulated for various routes of administration of the dosage form Embodiments (e.g., of a method, of a system, of a therapeutic composition, etc.) can include one or more (e.g., two, etc.) strategies to inhibit the interaction between Crohn's disease-associated I2 superantigen and MHC class II, such as for use as a therapy (and/or diagnostics) for CD (e.g., for improving one or more conditions and/or health states associated with CD, etc.). In a specific example, embodiments can include peptide inhibitor and/or small molecules inhibiting the interaction between Crohn's disease-associated I2 superantigen and MHC class II.

Embodiments can function to inhibit this the binding between I2 T-cell superantigen and MHC-II. Embodiments can include designing peptides and/or de novo molecules inhibitors (e.g., for inhibiting the binding between I2 T-cell superantigen and MHC-II. Embodiments can include an in-silico approach involving docking and/or structural biology approaches to design new specific inhibitors against Crohn's disease. In specific examples, determined (e.g., designed) specific inhibitors can be tested by in vitro experiments, but any suitable experiments and/or validation approaches can additionally or alternatively be used to evaluate specific inhibitors.

Embodiments (e.g., therapeutic compositions, formulations etc.) including and/or otherwise associated with the inhibitors can be used as treatment and/or as a palliative against Crohn's disease and/or Inflammatory bowel disease (IBD), and/or any other condition characterized by an inflammation of the gastrointestinal tract. Conditions can additionally or alternatively include one or more of an abnormal immune system response, chronic inflammation in the digestive tract, abdominal pain, severe diarrhea, fatigue, loss of appetite, fever, cramping, weight loss, ulcers within the intestines, fissures in the lining of the anus, increased risk of colorectal cancer, colorectal cancer, development of chronic health conditions, cardiovascular disease, respiratory disease, cancer, arthritis, kidney diseases, liver diseases, and/or any suitable associated condition. Conditions can include at least one of: symptoms, causes, diseases, disorders, associated risk, associated severity, and/or any other suitable aspects associated with conditions.

In an embodiment, the method of producing peptide inhibitors of Crohn' disease-associated I2 superantigen comprises: identifying potential immunogenic peptides from I2 superantigen by identifying the area of interaction with HLA-DR class II using bioinformatics prediction (and/or other suitable approaches), and/or reengineering the peptides corresponding to the HLA-DR class II area of interaction with I2 in-silico, such as to obtain new peptides with higher affinity to I2 and in consequence, inhibit the I2 superantigen/HLA-DR class II interaction.

In an embodiment, potential immunogenic peptides belonging to I2 that bind HLA-DRB1*37 and HLA-DRB1*07 alleles were identified using different epitope-prediction softwares. To this, the sequence of I2 superantigen from pfiT gene was obtained from Protein Data Bank database (code: 4M07). Using this method, five peptides of 15 amino acids length comprising the blue region of I2 sequence were identified as potential immunogenic peptides:

```
>4M07:
                                  (SEQ ID NO: 103)
AIPDBIDICHAINISEQUENCEGPLGSMDEHKALGVMRTMVDS

GQLTDPESARGKLLQTAAHLFRNKGFERTTVRDLASAVGIQSG

SIFHHFKSKDEILRAVMEENHYNTAMMRASLEEASTVRERVLA

LIRCELQSIMGGSGEAMAVLVYEWRSLSAEGQAHVLALRDVYE

QIWLQVLGEAKAAGYIRGDVFITRRFLTGALSWTTTWFRAQGS

LTLEELAEEALLMVLKSD
```

TABLE 5

| The summary of five peptides: | | |
|---|---|---|
| Binding area 1 | EETIHYNTAMMRASL (SEQ ID NO: 104) | Peptide 1 |
| | MEETIHYNTAMMRAS (SEQ ID NO: 105) | Peptide 2 |
| | ETIHYNTAMMRASLE (SEQ ID NO: 106) | Peptide 3 |
| | VMEETIHYNTAMMRA (SEQ ID NO: 107) | Peptide 4 |
| Binding area 2 | RGKLLQTAAHLFRNK (SEQ ID NO: 108) | Peptide 5 |

A common region between peptides 1, 2, 3 and 4 is underlined. The common motif among them correspond to the "ETIHYNTAMMRA" (SEQ ID NO: 109) sequence (Binding area 1). The region correspond to Binding area 2 comprising for "RGKLLQTAAHLFRNK" (SEQ ID NO: 108) sequence. Both regions will be used as binding area for docking against HLA-DR.

Figure 7:
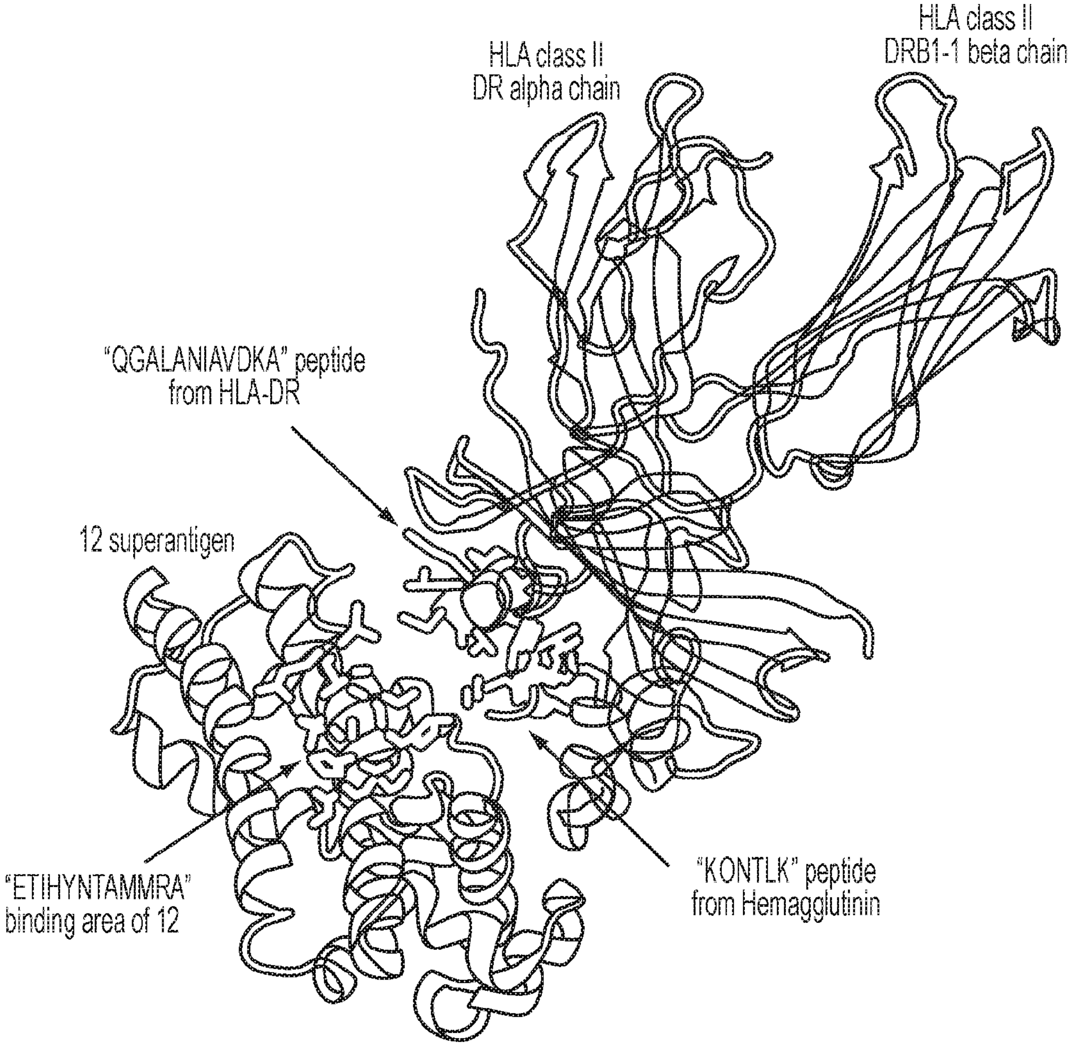
FIG. 7 illustrate SI2-MHC complex three dimensional structure.

In another embodiment, design of peptide inhibitors can include identifying the corresponding HLA binding region to I2. In a specific example, as shown by competition binding experiments, the predicted I2-binding site to HLA-DR can overlap with the corresponding HLA binding site of *mycoplasma* arthritidis mitogen (MAM), a phylogenetically and structurally distinct superantigen. In a specific example, based on the crystal structure of the MAM-MHC complex (PDB code: 1R5I), we identified the HLA binding region (from alpha and beta chains) and the hemagglutinin peptide (FIG. 7). In specific examples, the peptides can comprise one or more sequences: QGALANIAVDKA (SEQ ID NO: 110) (from HLA-DR) and/or KQNTLK (SEQ ID NO: 111) (from Hemagglutinin).

In specific examples, the peptides corresponding to HLA-DR and Hemagglutinin binding regions to I2 will be reengineered in the following stage.

In a specific example, in a first step (and/or performable at any suitable time and frequency in any suitable order), a structural analysis was performed to identify whether the immunogenic peptides of I2 superantigen from *P. fluorescens* are exposed to the solvent and therefore, can interact with the HLA-DR class II receptor. Thus, the solvent-accessible surface area (SASA) was calculated for these 5 peptides (and/or any suitable number of peptides) considering all (and/or any suitable amount of) the protein structure of the superantigen. In a specific example, all the peptides were predicted to be on the surface of the protein.

Then (and/or performable at any suitable time and frequency in any suitable order), a control molecular docking was performed to model the interaction between I2 superantigen and the two peptides (and/or suitable number of peptides) corresponding to HLA and Hemagglutinin binding regions: "QGALANIAVDKA" (SEQ ID NO: 110) and "KQNTLK" (SEQ ID NO: 111). However, any suitable modeling and/or approaches can be performed to evaluate the interactions between any suitable peptides and/or regions. In a specific example, the peptides were considered flexible for docking, in order to evaluate all the possible conformations. In a specific example, the docking binding energy were −5.9 and −5.7 kcal/mol respectively.

In a specific example, considering this, we designed new inhibitors against I2 superantigen to treat or palliate Crohn's disease based on reengineering of the two "QGALANIAVDKA" (SEQ ID NO: 110) and "KQNTLK" (SEQ ID NO: 111) peptides (but any suitable types of peptides can be reengineered, and/or selected for reengineering based on any suitable criteria). In this way, the new peptides can have better affinity to I2 than for those two peptides and can prevent the binding of I2 to HLA-DR. The modifications can include mutating each position of peptides for the 19 amino acids remaining (and/or any suitable number of amino acids). In a specific example, subsequently, docking between modified peptides and I2 superantigen was performed; and finally, a number of contacts analysis between the I2 receptor and the inhibitory modified peptides was performed to determine the main amino acids involved with the interaction. In a specific example, a distance of 5 angstrom was considered for the analysis (but any suitable distance can be used). According to the above specific examples, the results can be shown in Table 6 and Table 7:

TABLE 6

Specific examples of results of single mutations on "QGALANIAVDKA" (SEQ ID NO: 110) inhibitory peptide. The first column corresponds to amino acid mutation and the of the number position in the peptide. The second column corresponds to the sequence reengineered peptide. The third column is the complex docking affinity energy expressed in kcal/mol. The fourth column corresponds to the total number of amino acids of 12 that interact with the inhibitory peptide.

| Mutation | Peptide | Complex affinity energy | Total 12 contacts number |
|---|---|---|---|
| A12F | QGALANIAVDKF (SEQ ID NO: 112) | -7 | 28 |
| G2W | PWALANIAVDKA (SEQ ID NO: 113) | -6.9 | 25 |
| L4W | PWALANIAVDKA (SEQ ID NO: 114) | -6.9 | 29 |
| V9W | QGALANIAVVDKA (SEQ ID NO: 115) | -6.9 | 27 |
| K11T | QGALANIAVDTA (SEQ ID NO: 116) | -6.8 | 27 |
| V9P | QGALANIAPDKA (SEQ ID NO: 117) | -6.7 | 28 |
| I7R | QGALANRAVDKA (SEQ ID NO: 118) | -6.6 | 28 |
| N6L | OGALALIAVDKA (SEQ ID NO: 119) | -6.6 | 31 |
| A85 | QGALANIAGDKA (SEQ ID NO: 120) | -6.6 | 26 |
| V9R | QGALANIARDKA (SEQ ID NO: 121) | -6.5 | 27 |
| WOE | GALANIAVEKA (SEQ ID NO: 122) | -6.5 | 29 |
| 17G | QGALANGAVDKA (SEQ ID NO: 123) | -6.5 | 26 |
| A12H | C/GALANIAVDKH (SEQ ID NO: 124) | -6.5 | 27 |
| ASL | QGALLNIAVDKA (SEQ ID NO: 125) | -6.5 | 26 |
| 01F | FGALANIAVDKA (SEQ ID NO: 126) | -6.5 | 28 |
| K11E | OGALANIAVDEA (SEQ ID NO: 127) | -6.4 | 27 |
| V9G | QGALANIAGDKA (SEQ ID NO: 128) | -6.4 | 27 |
| K11H | OGALANIAVDHA (SEQ ID NO: 129) | -6.4 | 28 |
| A8H | OGALANIHVDKA (SEQ ID NO: 130) | -6.4 | 27 |
| A31 | QGILANIAVDKA (SEQ ID NO: 131) | -6.4 | 27 |
| G2P | QPALANIAVDKA (SEQ ID NO: 132) | -6.4 | 25 |

TABLE 6-continued

Specific examples of results of single mutations on "QGALANIAVDKA" (SEQ ID NO: 110) inhibitory peptide. The first column corresponds to amino acid mutation and the of the number position in the peptide. The second column corresponds to the sequence reengineered peptide. The third column is the complex docking affinity energy expressed in kcal/mol. The fourth column corresponds to the total number of amino acids of 12 that interact with the inhibitory peptide.

| Mutation | Peptide | Complex affinity energy | Total 12 contacts number |
|---|---|---|---|
| L4Y | QGAYANIAVDKA (SEQ ID NO: 133) | -6.4 | 26 |
| G2F | QFALANIAVDKA (SEQ ID NO: 134) | -6.3 | 25 |
| AST | QGALTNIAVDKA (SEQ ID NO: 135) | -6.3 | 26 |
| D1OW | QGALANIAVVVKA (SEQ ID NO: 136) | -6.3 | 26 |
| A3W | QGWLANIAVDKA (SEQ ID NO: 137) | -6.3 | 27 |
| L4T | QGATANIAVDKA (SEQ ID NO: 138) | -6.2 | 27 |
| 17W | QGALANWAVDKA (SEQ ID NO: 139) | -6.2 | 25 |
| G2Y | QYALANIAVDKA (SEQ ID NO: 140) | -6.2 | 25 |
| A8Y | OGALANIYVDKA (SEQ ID NO: 141) | -6.2 | 26 |
| 17D | QGALANDAVDKA (SEQ ID NO: 142) | -6.1 | 29 |
| I7C | QGALANCAVDKA (SEQ ID NO: 143) | -6.1 | 25 |
| V9E | QGALANIAEDKA (SEQ ID NO: 144) | -6.1 | 29 |
| Al2N | QGALANIAVDKQ (SEQ ID NO: 145) | -6 | 30 |
| A8N | OGALANIOVDKA (SEQ ID NO: 146) | -6 | 28 |
| N6K | QGALAKIAVDKA (SEQ ID NO: 147) | -6 | 27 |
| K11V | QGALAKIAVDKA (SEQ ID NO: 148) | -6 | 25 |
| A8V | QGALANIVVDKA (SEQ ID NO: 149) | -6 | 28 |

TABLE 7

Specific examples of results of single mutations on "KQNTLK" (SEQ ID NO: 111) inhibitory peptide. The first column corresponds to amino acid mutation and the position in the peptide. The second column corresponds to peptide sequence. The third column includes the docking complex affinity energy expressed in kcal/mol. The fourth column corresponds to the total number of amino acids of 12 that interact with the inhibitory peptide.

| Mutation | Peptide | Complex affinity energy | Total 12 contacts number |
|---|---|---|---|
| K1W | WQNTLK (SEQ ID NO: 150) | -6.6 | 23 |
| K6W | KQNTLW (SEQ ID NO: 151) | -6.4 | 22 |
| K6Y | KQNTLY (SEQ ID NO: 152) | -6.4 | 25 |
| K6P | KQNTLP (SEQ ID NO: 153) | -6.2 | 23 |
| K3P | KQPTLK (SEQ ID NO: 154) | -6.1 | 25 |
| K1V | VQNTLK (SEQ ID NO: 155) | -6.1 | 22 |
| Q2N | KNNTLK (SEQ ID NO: 156) | -6 | 22 |
| N3I | KQITLK (SEQ ID NO: 157) | -6 | 21 |
| LDS | KQNTDK (SEQ ID NO: 158) | -6 | 22 |
| Q2T | KTNTLK (SEQ ID NO: 159) | -6 | 23 |
| K6R | KQNTLR (SEQ ID NO: 160) | -5.9 | 22 |
| K1S | SQNTLK (SEQ ID NO: 161) | -5.9 | 22 |
| Q2P | KPNTLK (SEQ ID NO: 162) | -5.8 | 22 |
| N3D | KQDTLK (SEQ ID NO: 163) | -5.8 | 23 |
| T4V | KQNVLK (SEQ ID NO: 164) | -5.8 | 22 |
| K1L | LQNTLK (SEQ ID NO: 165) | -5.8 | 21 |

In an embodiment, the peptide inhibitor described herein has the following characteristics: an affinity energy of less than −5.7 kcal/mol for the case of the "KQNTLK" (SEQ ID NO: 111) peptide and less than −5.9 kcal/mol for the "QGALANIAVDKA" (SEQ ID NO: 110) peptide and/or high number of total contacts.

In an embodiment, the present disclosure relates to a therapeutic composition comprising a peptide comprising a sequence having 60%, 65%, 70%, 75%, 80%, 85%, 90%, 95%, or 100% identity to the "KQNTLK" (SEQ ID NO: 111) peptide or the "QGALANIAVDKA" (SEQ ID NO: 110) peptide.

In a specific example, using as a base the six amino acid peptide "WQNTLK" (SEQ ID NO: 166) attached to the receptor by docking, a cavity detection was performed to identify the positions and binding site on the protein surface. In a specific example, with this information, a pharmacophore model was designed using the peptide geometrical structure and physical chemistry properties of the binding site.

In an embodiment, one or more small molecules were constructed iteratively using organic fragments databases (and/or other suitable databases) and/or genetic algorithms (and/or other suitable algorithms). In a specific example, the protein-molecule binding affinity was evaluated by a scoring function. In a specific example, then (and/or at any suitable time and frequency in any suitable order), de novo molecules were docked to the I2 receptor using the molecular docking methodology (but any suitable approaches can be used). In a specific example, later (and/or at any suitable time and frequency in any suitable order), de novo molecules were evaluated by different rules to select the best ligands based on ADME/T properties (absorption, distribution, metabolism, excretion, and toxicity), druggability and/or synthetic accessibility, and/or any suitable criteria can be used for selection.

Additionally or alternatively, a contact analysis between de novo molecules and the I2 protein can be performed with the objective of maintaining the interactions of the molecules with the amino acids reported in literature that are important in the binding with HLA-DR, as described in the previous section with peptides mutated.

In specific examples, such as according to any combination of the above, embodiments can include any suitable method, system, and/or therapeutic composition including and/or associated with (e.g., for determining, designing, generating, etc.) molecules to be protected as inhibitors of I2 superantigen meeting one or more of the following criteria:

- They are druggable molecules (e.g., meet Lipinski's rules; meet any suitable druggability rules),
- They have a higher binding affinity for I2 protein than the original peptides from HLA binding zone (e.g., docking energies less than −6.8 kcal/mol; any suitable docking energies),
- They have a molecular weight less than 500 g/mol (and/or any suitable molecular weight),
- Their score of synthetic accessibility is less than 3 (and/or other suitable score) indicating that they are feasible to be synthesized, and/or
- Compared with the original peptides, they maintain the main contacts (and/or any suitable contacts) with the I2 protein.

Figure 8:
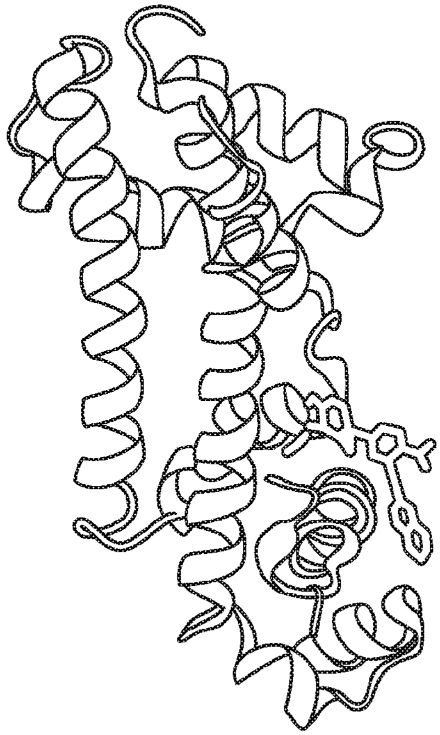
FIG. 8 illustrate the docking of de novo molecule "mol-6" with I2 receptor.

The region of interaction of the molecules with the I2 superantigen is depicted in FIG. 8. Molecules mol-1 to mol-7 are detailed in Table 8.

Embodiments (e.g., therapeutic compositions, etc.) can thus include and/or otherwise be associated with de novo small molecules to be protected as inhibitory compounds of I2 superantigen for Crohn's disease treatment or palliative treatment, including any one or more of the following compounds in pharmaceutically acceptable form or a pharmaceutically acceptable salt thereof:

Table 8: Small Molecules Inhibiting I2 Superantigen.

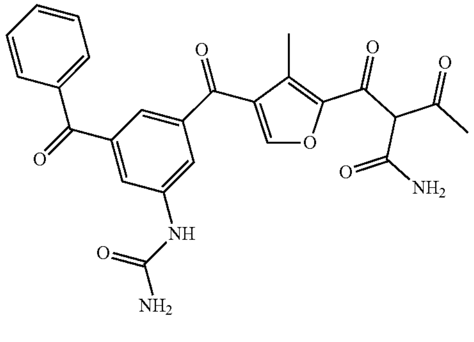 [SMILES: CC(=O)C(C(N)=O)C(=O)c1occ(C(=O)c2cc(NC(N)=O)cc(C(=O)c3ccccc3)c2)c1C]

Name: mol-1
Docking Energy: −8.6
Formule: C24H2ON4O7
Weight: 476
LogP: 0.68

-continued

No. of atoms: 55
Important contacts number: 11/20
Druggable: YES
No. of H Bond Donors: 3
No. of H Bond Acceptors: 6
No. of Rotatable Bonds: 10
No. of N and 0 Atoms: 11
No. of Rings: 3
Synthetic accessibility: 2.987
SMILES code:
c1(cc(cc(c1)C(=O)c1c(c(oc1)C(=O)N(C(=O)CC(=O)NC)NC(=O)N)C(=O)c1ccccc1)

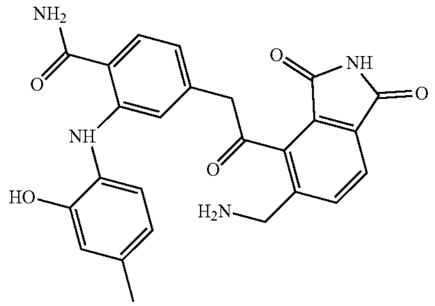 [SMILES: Cc1ccc(Nc2cc(CC(=O)c3c(CN)ccc4c3C(=O)NC4=O)ccc2C(N)=O)c(O)c1]

Name: mol-2
Docking Energy: −8.1
Formule: C24H21N4O6
Weight: 461
LogP: 1.54
No. of atoms: 55
Important contacts number: 10/18
Druggable: YES
No. of H Bond Donors: 5
No. of H Bond Acceptors: 5
No. of Rotatable Bonds: 8
No. of N and 0 Atoms: 10
No. of Rings: 4
Synthetic accessibility: 2.816
SMILES code:
c1(ccc(c(c1)Nc1ccc(C)cc1O)C(=O)N)OC(=O)c1c2c(C(=O)NC2=O)ccc1C[NH3]

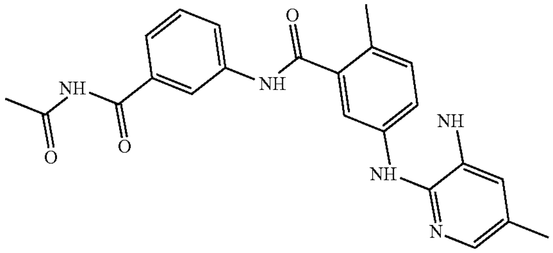 [SMILES: CC(=O)NC(=O)c1cccc(NC(=O)c2cc(Nc3ncc(C)cc3N)ccc2C)c1]

Name: mol 3
Docking Energy: −8.1
Formule: C23H22N4O4
Weight: 418
LogP: 3
No. of atoms: 53
Important contacts number: 8/12
Druggable: YES
No. of H Bond Donors: 4
No. of H Bond Acceptors: 5
No. of Rotatable Bonds: 9
No. of N and O Atoms: 8
No. of Rings: 3

-continued

Synthetic accessibility: 2.329
SMILES code:
c1c(ccc(c1C(=O)Nc1cccc(c1)C(=O)NC(=O)CC)Nc1ncc(C)cc1O)

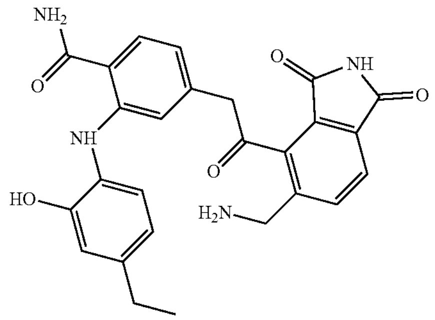 [SMILES: CCc1ccc(Nc2cc(CC(=O)c3c(CN)ccc4c3C(=O)NC4=O)ccc2C(N)=O)c(O)c1]

Name: mol 4
Docking Energy: −8
Formule: C25H23N4O6
Weight: 475
LogP: 1.79
No. of atoms: 58
Important contacts number: 10/18
Druggable: YES
No. of H Bond Donors: 5
No. of H Bond Acceptors: 5
No. of Rotatable Bonds: 9
No. of N and O Atoms: 10
No. of Rings: 4
Synthetic accessibility: 2.851
SMILES code:
c1(ccc(c(c1)Nc1ccc(cc1))CC)C(=O)N)OC(=O)c1c2c(C(=O)NC2=O)cc1C[NH3]

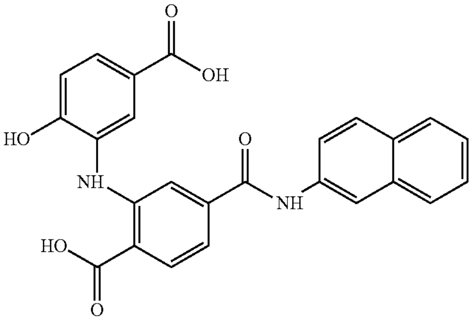 [SMILES: O=C(O)c1ccc(O)c(Nc2cc(C(=O)Nc3ccc4ccccc4c3)ccc2C(=O)O)c1]

Name: mol-5
Docking Energy: −7.9
Formule: C24H17N306
Weight: 443
LogP: 3.86
No. of atoms: 50
Important contacts number: 9/16
Druggable: YES
No. of H Bond Donors: 5
No. of H Bond Acceptors: 7
No. of Rotatable Bonds: 10
No. of N and 0 Atoms: 9
No. of Rings: 4
Synthetic accessibility: 2.303
SMILES code:
c1c(ccc(c1Nc1nc(ccc1O)C(=O)O)C(=O)O)C(=O)Nc1cc2c(cc1)ccc2

-continued

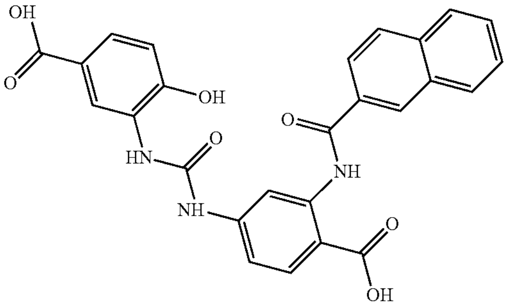 [SMILES: O=C(Nc1ccc(C(=O)O)c(NC(=O)c2ccc3ccccc3c2)c1)Nc1cc(C(=O)O)ccc1O]

Name: mol-6
Docking Energy: −7.9
Formule: C26H18N307
Weight: 484
LogP: 3.1
No. of atoms: 54
Important contacts number: 7/15
Druggable: YES
No. of H Bond Donors: 5
No. of H Bond Acceptors: 7
No. of Rotatable Bonds: 10
No. of N and 0 Atoms: 10
No. of Rings: 4
Synthetic accessibility: 2.179
SMILES code:
c1(ccc(c(c1)NC(=O)c1cc2ccccc2cc1)C(=O)O)NC(=O)Nc1c(cc(c1)C(=O)O)O

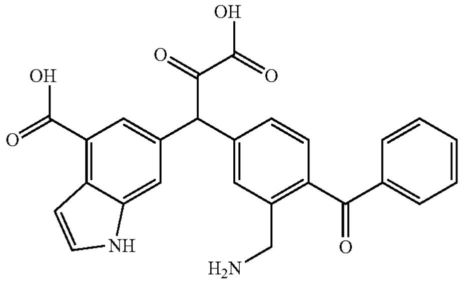 [SMILES: NCc1cc(C(C(=O)C(=O)O)c2cc(C(=O)O)c3cc[nH]c3c2)ccc1C(=O)c1ccccc1]

Name: mol-7
Docking Energy: −6.9
Formule: C25H19N306
Weight: 457
LogP: 2.38
No. of atoms: 53
Important contacts number: 9/17
Druggable: YES
No. of H Bond Donors: 2
No. of H Bond Acceptors: 6
No. of Rotatable Bonds: 8
No. of N and 0 Atoms: 9
No. of Rings: 4
Synthetic accessibility: 2.782
SMILES code:
C(=O)(N(c1cc(c2cc[nH]c2c1)C(=O)O)c1cc(c(cc1)C(=O)c1ccccc1)C[NH3])C(=O)O

TABLE 9

| Details of the contact interactions: | | | | | | | | | | | | | | | | | | | | |
|---|---|---|---|---|---|---|---|---|---|---|---|---|---|---|---|---|---|---|---|---|
| Name | Residues of I2 that interact with the protected small molecules | | | | | | | | | | | | | | | | | | | |
| mol-1 | 107 | 108 | 109 | 11 | 110 | 12 | 13 | 14 | 17 | 18 | 19 | 21 | 22 | 26 | 66 | 69 | 70 | 72 | 73 | 76 |
| | SER | GLY | GLU | THR | ALA | ASP | PRO | GLU | ARG | GLY | LYS | LEU | GLN | HIS | VAL | GLU | THR | HIS | TYR | ALA |
| mol-2 | 107 | 108 | 109 | 11 | 110 | 13 | 21 | 22 | 25 | 26 | 65 | 66 | 69 | 70 | 72 | 73 | 74 | 76 | — | — |
| | SER | GLY | GLU | THR | ALA | PRO | LEU | GLN | ALA | HIS | ALA | VAL | GLU | THR | HIS | TYR | ASN | ALA | | |
| mol-3 | 107 | 11 | 110 | 21 | 22 | 26 | 66 | 69 | 70 | 72 | 73 | 76 | — | — | — | — | — | — | — | — |
| | SER | THR | ALA | LEU | GLN | ALA | VAL | GLU | THR | HIS | TYR | ALA | | | | | | | | |
| mol-4 | 107 | 108 | 109 | 11 | 110 | 13 | 21 | 22 | 25 | 26 | 65 | 66 | 69 | 70 | 72 | 73 | 74 | 76 | — | — |
| | SER | GLY | GLU | THR | ALA | PRO | LEU | GLN | ALA | HIS | ALA | VAL | GLU | THR | HIS | TYR | ASN | ALA | | |
| mol-5 | 107 | 108 | 109 | 11 | 110 | 18 | 21 | 22 | 25 | 65 | 66 | 69 | 70 | 72 | 73 | 76 | — | — | — | — |
| | SER | GLY | GLU | THR | ALA | GLY | LEU | GLN | ALA | ALA | VAL | GLU | THR | HIS | TYR | ALA | | | | |
| mol-6 | 107 | 108 | 109 | 110 | 13 | 19 | 22 | 23 | 25 | 26 | 44 | 45 | 69 | 70 | 73 | — | — | — | — | — |
| | SER | GLY | GLU | ALA | PRO | LYS | GLN | THR | ALA | HIS | ALA | VAL | GLU | THR | TYR | | | | | |
| mol-7 | 105 | 106 | 107 | 108 | 109 | 11 | 110 | 18 | 21 | 22 | 25 | 26 | 66 | 69 | 70 | 73 | 77 | — | — | — |
| | GLY | GLY | SER | GLY | GLU | THR | ALA | GLY | LEU | GLN | ALA | HIS | VAL | GLU | THR | TYR | MET | | | |

EXAMPLES

Example 1: Epitopes for Treating Peanut Allergy

As an example, from *Arachis hypogaea* (peanut) Ara-h allergen protein sequences, we predicted 58002 potential epitopes. These epitopes were filtered by rank, affinity, and removing duplicated sequences (and/or any suitable combination of approaches described herein; etc.), which resulted in an obtained 305 de novo epitopes. Those sub-database of sequences was aligned against Clostridiales bacteria *Fusicatenibacter* spp., a species eventually associated with peanut allergy, obtaining the final epitope "EEQGAIVTVRGGLRI" (SEQ ID NO: 167) (however, any suitable variation of the epitope sequence can be used in associated with approaches described herein; etc.). Epitopes that did not fit with the criteria described in Methodology section were discarded. The candidate epitope "EEQGAIVTVKGGLRI" (SEQ ID NO: 3), was reengineered obtaining better affinity with MHC receptor type II, mutating positions, 2, 3 and 5 by T, P and W, respectively.

Example 2: Epitopes Derived from *Arachis hypogaea* Ara-h Allergen Protein Sequences From *Arachis hypogaea* Ara-h allergen protein sequences, we predicted 58002 potential-epitopes from T cell Prediction Epitopes Pipeline (and/or suitable approaches described herein), where 1614 of them were high-ranked epitopes according scoring provided by each server. Duplicated sequences were discarded, then only 305 "de nova" epitopes resulted to be unique sequences. Then, this sequences were aligned against *Fusicatenibacter saccharivorans* and *Flavonifractor plautii*. Consequently, we obtained six "common epitopes" between allergen sequences from *Arachis hypogaea* and *F. saccharivorans* (EEQGAIVTVRGGLRI (SEQ ID NO: 167), EQGAIVTVRGGLRIL (SEQ ID NO: 168), GLMSLSWMINFIRQV (SEQ ID NO: 169), LVALALFLLAAHASA (SEQ ID NO: 170), QGAIVTVRGGLRILS (SEQ ID NO: 171), TGNVASFLTSFSFEM (SEQ ID NO: 172)), and nine between *A. hypogaea* and *F. plautii* (ANYAYNYSVVGGVAL (SEQ ID NO: 173), FCIFFLILFLAQEYG (SEQ ID NO: 174), GFCIFFLILFLAQEY (SEQ ID NO: 175), GTIIGLAIATPVFTF (SEQ ID NO: 176), GTLLLFAGLALAGTL (SEQ ID NO: 177), LRRPFYSNAPQEIFI (SEQ ID NO: 178), NYAYNYSVVGGVALP (SEQ ID NO: 179), PAAITLALAAGGFLF (SEQ ID NO: 180), RRPFYSNAPQEIFIQ (SEQ ID NO: 181)). Epitopes that did not fit with the criteria described in Methodology section were discarded. However, any suitable criteria can be used.

Proteomes:

TABLE 10

| Organisms, association, and taxonomy. | | | | |
|---|---|---|---|---|
| NCBI TaxaID | Organism | Association | Taxonomic Order | Best Protein Match of Organism |
| 292800 | *Flavonifractor plautii* | Increased in individuals with peanut allergy | *Clostridiales* | Uncharacterized Protein (Uniprot1D:G9YMO 5) |
| 1150298 | *Fusicatenibacter saccharivorans* | Decreased in individuals with peanut allergy. | *Clostridiales* | Pyruvate phosphate dikinase (Uniprot1D:AOA174 PZ33) |

TABLE 11

| Epitope origin and organism match. | | | | | | |
|---|---|---|---|---|---|---|
| Epi+31 tope | Found Aller+31 gen | Organism | %id | %sim | Pairwise match | Docking results (kcal/mol) |
| ANYA YNYS VVGG VAL (SEQ ID NO: | Arah8 | *F. plautii* | 75 | 91.7 | 12 | -7.2 |

TABLE 11-continued

| Epitope origin and organism match. | | | | | | |
|---|---|---|---|---|---|---|
| Epi+31 tope | Found Aller+31 gen | Organism | %id | %sim | Pairwise match | Docking results (kcal/mol) |
| 173) | | | | | | |
| NYAY NYSV VGGV ALP (SEQ ID NO: 179) | Arah8 | *F. plautii* | 75 | 91.7 | 12 | -6.9 |
| EQGA IVTV RGGL RIL (SEQ ID NO: 168) | Arah3 | *F.*saccharivorans | 73 | 90.9 | 12 | -6.4 |
| EEQG AIVT VRGG LRI (SEQ ID NO: 167) | Arah3 | *F.*saccharivorans | 73 | 90.9 | 12 | -7.2 |
| QGAI VTVR GGLR ILS (SEQ ID NO: 171) | Arah3 | *F.*saccharivorans | 73 | 90.9 | 12 | -5.8 |

Finally (and/or at any suitable time and frequency), to classify "common epitopes" according their affinity to the receptor, we ran docking simulations of 5 filtered de-nova epitopes from Ara h-type allergens against HLA-DPB1; a MHC class II receptor structure (PDB code: 3LQZ).

In specific examples to find an improvement of best epitopes, epitopes can be evaluated through a re-engineering process, consisting of sequential mutation in-silica and considering the other 19 amino acids, one at the time, by checking their effect over the docking affinity. As an example one of the inverse associated (EEQGAIVTVKGGLRI (SEQ ID NO: 3), docking energy: −7.2 kcal/mol) and one of associated organism (NYANYSVVGGVALP (SEQ ID NO: 182), docking energy: −6.9 kcal/mol) wild-type epitopes were re-engineered with values of binding energy obtained from docking results, described in Table 12 and Table 13 respectively. Bold letters represent single mutation that improves the most the energy over the WT epitope.

TABLE 12

| Docking results for the reengineering epitope EEQGAIVTVKGGLRI (SEQ ID NO: 3) | | | | | | | | | | | | | | | |
|---|---|---|---|---|---|---|---|---|---|---|---|---|---|---|---|
| | EEOGAIVTVKGGLRI Docking Values of single mutants (kcal/mol) | | | | | | | | | | | | | | |
| AA | 1 E | 2 E | 3 Q | 4 G | 5 A | 6 I | 7 V | 8 T | 9 V | 10 K | 11 G | 12 G | 13 L | 14 R | 15 I |
| A | -5.6 | -5.9 | -6.3 | -6.2 | - | -6.4 | -5.6 | -6.5 | -6.8 | -4.7 | -6.2 | -6.0 | -6.1 | -6.4 | -6.7 |
| C | -6.5 | -5.6 | -6.5 | -6.3 | -6.8 | -6.4 | -4.4 | -6.6 | -6.1 | -6.4 | -6.4 | -6.0 | -4.9 | -6.2 | -6.5 |
| D | -6.6 | -5.9 | -5.9 | -6.2 | -6.1 | -6.4 | 4.3 | -5.6 | -7.1 | -6.3 | -6.4 | -6.5 | -6.4 | -5.9 | -6.7 |
| E | - | - | -6.3 | -6.3 | -4.7 | -6.8 | -6.4 | -4.9 | -6.0 | -6.9 | -6.1 | -5.8 | -6.8 | -5.3 | -6.6 |
| F | -6.9 | -5.8 | -6.5 | -6.3 | -6.0 | -5.4 | -6.5 | -6.5 | -6.2 | -6.3 | -5.8 | -6.7 | -6.5 | -6.4 | -6.6 |
| G | -6.7 | -6.4 | -6.2 | - | -6.2 | -6.4 | -6.6 | -5.7 | -6.0 | -6.0 | - | - | -5.6 | -6.2 | -6.1 |
| H | -64 | -6.0 | -6.1 | -6.8 | -6.3 | -5.9 | -6.4 | -6.6 | -6.5 | -5.9 | -5.9 | -6.5 | -5.8 | -5.1 | -7.9 |

TABLE 12-continued

| Docking results for the reengineering epitope EEQGAIVTVKGGLRI (SEQ ID NO: 3) | | | | | | | | | | | | | | | |
|---|---|---|---|---|---|---|---|---|---|---|---|---|---|---|---|
| | EEOGAIVTVKGGLRI Docking Values of single mutants (kcal/mol) | | | | | | | | | | | | | | |
| | 1 | 2 | 3 | 4 | 5 | 6 | 7 | 8 | 9 | 10 | 11 | 12 | 13 | 14 | 15 |
| AA | E | E | Q | G | A | I | V | T | V | K | G | G | L | R | I |
| I | -5.4 | -6.1 | -5.2 | -5.1 | -6.2 | - | -6.2 | -6.5 | -6.1 | -5.5 | -5.3 | -5.8 | -5.6 | -5.3 | - |
| K | -5.9 | -5.7 | -5.8 | -6.6 | -6.4 | -6.0 | -6.2 | -5.5 | -6.0 | - | -6.6 | -5.6 | -5.9 | -6.0 | -4.9 |
| L | -7.0 | -5.1 | -6.9 | -6.1 | -5.2 | -6.3 | -5.5 | -5.6 | -6.6 | -6.0 | -6.2 | -6.6 | - | -6.4 | -6.3 |
| M | -6.7 | -5.9 | -6.9 | -6.2 | -6.1 | -6.1 | -6.4 | -5.8 | -6.1 | -6.1 | -5.8 | -5.3 | -6.4 | -5.9 | -6.6 |
| N | -6.3 | -6.2 | -5.6 | -5.1 | -5.6 | -6.2 | -5.8 | -6.2 | -6.3 | -6.4 | -6.4 | -6.3 | -6.9 | -6.4 | -6.5 |
| P | -6.7 | -5.9 | -8.5 | -5.2 | -6.5 | -7.1 | -5.9 | -6.3 | -4.5 | -5.9 | -5.3 | -7.0 | -6.7 | -6.1 | -6.0 |
| Q | -6.0 | -5.8 | - | -5.6 | -5.8 | -6.5 | -5.8 | -5.6 | -6.2 | -6.9 | -7.3 | -6.4 | -6.3 | -6.0 | -6.8 |
| R | -6.5 | -6.6 | -5.8 | -5.0 | -5.5 | -6.3 | -6.2 | -5.9 | -4.9 | -5.6 | -5.0 | -6.8 | -4.7 | - | -5.5 |
| S | -5.8 | -6.2 | -5.4 | -5.9 | -6.1 | -6.2 | -6.3 | -6.1 | -6.6 | -5.9 | -6.9 | -6.4 | -5.5 | -5.1 | -6.0 |
| T | -6.4 | -7.2 | -6.8 | -5.8 | -5.6 | -6.4 | -5.3 | - | -5.2 | -6.2 | -6.6 | -6.2 | -6.6 | -7.0 | -6.0 |
| V | -6.3 | -5.2 | -5.9 | -6.6 | -5.7 | -6.2 | - | -6.3 | - | -4.4 | -5.9 | -6.2 | -6.1 | -6.6 | -6.3 |
| W | -6.6 | -6.3 | -6.4 | -6.1 | -7.3 | -6.6 | -5.4 | -6.5 | -5.1 | -6.1 | -5.9 | -6.9 | -6.3 | -6.3 | -8.1 |
| Y | -6.4 | -7.0 | -6.9 | -6.2 | -5.8 | -6.4 | -6.7 | -6.7 | -5.6 | -6.1 | -6.1 | -6.5 | -6.2 | -5.9 | -6.2 |

TABLE 13

| Docking results for the reengineering epitope NYAYNYSVVGGVALP (SEQ ID NOL 179) | | | | | | | | | | | | | | | |
|---|---|---|---|---|---|---|---|---|---|---|---|---|---|---|---|
| | NYAYNYSWGGVALP Docking values of single mutants (kcal/mol) | | | | | | | | | | | | | | |
| | 1 | 2 | 3 | 4 | 5 | 6 | 7 | 8 | 9 | 10 | 11 | 12 | 13 | 14 | 15 |
| AA | N | Y | A | Y | N | Y | S | V | V | G | G | V | A | L | P |
| A | -6.9 | -6.5 | — | -6.8 | -7.4 | -7.3 | -7.5 | -7.0 | -6.9 | -8.0 | -9.1 | -7.3 | — | -7.0 | -6.2 |
| C | -7.6 | -7.4 | -17.3 | -7.6 | -6.8 | -7.2 | -7.3 | -6.6 | -7.3 | -6.4 | -7.1 | -6.3 | -8.1 | -6.8 | -6.6 |
| D | -7.1 | -6.7 | -6.8 | -7.0 | -7.9 | -6.9 | -6.5 | -6.8 | -7.2 | -6.4 | -5.0 | -7.7 | -7.1 | -7.2 | -8.1 |
| E | -6.7 | -5.8 | -7.0 | -5.7 | -6.7 | -7.4 | -6.7 | -7.1 | -6.9 | -6.9 | -6.0 | -8.3 | -6.4 | -6.8 | -6.8 |
| F | -8.0 | -7.4 | -6.9 | -6.9 | -6.8 | -7.5 | -7.4 | -6.4 | -7.3 | -7.0 | -7.5 | -6.4 | -6.7 | -7.0 | -8.0 |
| G | -7.0 | -7.8 | -7.8 | -5.9 | -6.2 | -7.0 | -6.1 | -5.8 | -7.7 | — | — | -6.7 | -7.3 | -8.0 | -6.1 |
| H | -8.2 | -7.0 | -6.9 | -7.0 | -7.9 | -6.8 | -6.0 | -7.6 | -7.6 | -8.3 | -6.4 | -7.1 | -7.6 | -7.4 | -7.9 |
| I | -6.7 | -6.3 | -8.2 | -7.0 | -6.9 | -5.7 | -7.5 | -7.1 | -6.1 | -7.2 | -6.9 | -5.9 | -6.6 | -6.7 | -7.6 |
| K | -6.7 | -6.6 | -8.1 | -7.4 | -7.2 | -6.3 | -5.9 | -7.1 | -7.4 | -7.2 | -9.0 | -7.6 | -5.5 | -6.4 | -7.6 |
| L | -7.3 | -7.4 | -7.3 | -7.2 | -8.7 | -8.3 | -7.2 | -8.4 | -7.1 | -7.6 | -6.9 | -6.6 | -8.2 | — | -6.4 |
| M | -7.2 | -7.0 | -5.9 | -7.4 | -7.6 | -5.8 | -6.2 | -7.6 | -6.8 | -6.4 | -7.3 | -6.9 | -6.4 | -7.3 | -7.1 |
| N | — | -7.8 | -6.4 | -7.6 | — | -4.9 | -7.8 | -6.2 | -7.5 | -7.0 | -7.3 | -7.1 | -6.3 | -7.3 | -6.7 |
| P | -7.4 | -6.6 | -5.5 | -6.3 | -6.9 | -7.1 | -7.5 | -7.9 | -6.6 | -7.1 | -6.6 | -6.3 | -7.7 | -7.0 | — |
| Q | -5.8 | -6.4 | -7.1 | -7.8 | -7.8 | -6.1 | -6.9 | -7.4 | -8.7 | -8.9 | -7.9 | -6.0 | -6.8 | -6.8 | -6.5 |
| R | -7.7 | -6.1 | -6.4 | -6.9 | -6.4 | -7.0 | -79 | -9.3 | -6.8 | -8.1 | -7.3 | -6.7 | -7.6 | -7.4 | -6.7 |
| S | -7.3 | -5.4 | -7.8 | -7.2 | -9.4 | -6.8 | — | -6.6 | -6.7 | -7.2 | -7.2 | -8.0 | -7.1 | -7.8 | -5.5 |
| T | -8.9 | -7.6 | -7.5 | -6.4 | -7.4 | -6.9 | -7.1 | -5.7 | -9.3 | -6.7 | -7.4 | -5.9 | -6.5 | -7.7 | -7.1 |

TABLE 13-continued

| Docking results for the reengineering epitope NYAYNYSVVGGVALP (SEQ ID NOL 179) | | | | | | | | | | | | | | | |
|---|---|---|---|---|---|---|---|---|---|---|---|---|---|---|---|
| | NYAYNYSWGGVALP Docking values of single mutants (kcal/mol) | | | | | | | | | | | | | | |
| | 1 | 2 | 3 | 4 | 5 | 6 | 7 | 8 | 9 | 10 | 11 | 12 | 13 | 14 | 15 |
| AA | N | Y | A | Y | N | Y | S | V | V | G | G | V | A | L | P |
| V | −6.8 | −7.9 | −6.2 | −6.2 | −7.0 | −7.1 | −8.0 | — | — | −7.4 | −8.1 | — | −11.0 | −6.2 | −6.8 |
| W | −6.9 | −6.9 | −6.4 | −6.6 | −6.9 | −6.9 | −7.5 | −7.1 | −7.7 | −6.6 | −7.5 | −7.3 | −6.8 | −8.1 | −6.9 |
| Y | −8.1 | — | −7.1 | — | −6.3 | — | −7.0 | −7.2 | −6.8 | −7.2 | −8.8 | −6.6 | −7.5 | −8.8 | −5.9 |

In specific examples according to the Table and criteria, improved reengineered epitopes obtained with better binding energy compared with wild type can include those with the following patterns:

Epitope:
(SEQ ID NO: 3)
EEQGAIVTVKGGLRI

2: T
3: P
5: W
11: Q
15: H, W

Epitope:
(SEQ ID NO: 179)
NYAYNYSVVGGVALP

1: A, C, D, F, G, H, L, M, P, R, S, T, W, Y
2: C, F, G, H, L, M, N, T, V, W
3: C, E, F, G, H, I, K, L, Q, S, T, Y
4: C, D, F, H, I, K, L, M, N, Q, R, S
5: A, D, H, I, K, L, M, P, Q, S, T, V, W
6: A, C, D, E, F, G, L, P, R, T, V, W
7: A, C, F, I, L, N, P, Q, R, T, V, W, Y
8: A, E, H, I, K, L, M, P, Q, R, W, Y
9: A, C, D, E, F, G, H, K, L, N, Q, T, W
10: A, E, F, H, I, K, L, N, P, Q, R, S, V, Y
11: A, C, F, I, K, L, M, N, Q, R, S, T, V, W, Y
12: A, D, E, H, K, M, N, S, W
13: C, D, G, H, L, P, R, S, V, Y
14: A, D, F, G, H, M, N, P, R, S, T, W, Y
15: D, F, H, I, K, M, T, W

TABLE 14

| Additional or alternative examples of epitopes that might be reengineered: | | |
|---|---|---|
| AKLTILVALALFLLA (SEQ ID NO: 183) | ATPLLVIFSPILVPA (SEQ ID NO: 184) | ASLKFAFVMLVCMAM (SEQ ID NO: 185) |

TABLE 14-continued

| Additional or alternative examples of epitopes that might be reengineered: | | |
|---|---|---|
| ATPVFTFFSPVIVPA (SEQ ID NO: 186) | CIFFLILFLAQEYGV (SEQ ID NO: 187) | MAKLT1LVALALFLL (SEQ ID NO: 188) |
| CIFFLVLFLAQEGVV (SEQ ID NO: 189) | MASLKFAFVMLVCMA (SEQ ID NO: 190) | MIDFEEFRVMMMMGS (SEQ ID NO: 191) |
| DFEEFRVMMMMGSRH (SEQ ID NO: 192) | MMVKLSILVALLGAL (SEQ ID NO: 193) | DGMIDFEEFRVMMMM (SEQ ID NO: 194) |
| DGYISLQEFIELNTK (SEQ ID NO: 195) | MVKLSILVALLGALL (SEQ ID NO: 196) | FEEFRVMMMMGSRHD (SEQ ID NO: 197) |
| NIFSGFTPEFLEQAF (SEQ ID NO: 198) | FFLILFLAQEYGVEG (SEQ ID NO: 199) | NPFKFFVPPFQQSPR (SEQ ID NO: 200) |
| FFLVLFLAQEGVVKT (SEQ ID NO: 201) | PLFILFSPVIVPATI (SEQ ID NO: 202) | FLILFLAQEYGVEGK (SEQ ID NO: 203) |
| PVFIFFSPVIVPAW (SEQ ID NO: 204) | FLVLFLAQEGWKTE (SEQ ID NO: 205) | PVFTFFSPVIVPAVV (SEQ ID NO: 206) |
| FSGFAQEFLQHAFQV (SEQ ID NO: 207) | QAIKFMTASTIGVSF (SEQ ID NO: 208) | FSGFTPEFLAQAFQV (SEQ ID NO: 209) |
| RQAIKFMTASTIGVS (SEQ ID NO: 210) | GFAQEFLQHAFQVDR (SEQ ID NO: 211) | SGFAQEFLQHAFQVD (SEQ ID NO: 212) |
| GFCIFFLILFLAQEY (SEQ ID NO: 213) | SGFTPEFLAQAFQVD (SEQ ID NO: 214) | GSNIFSGFAQEFLQH (SEQ ID NO: 215) |
| TGGTLLLLSGLSLLG (SEQ ID NO: 216) | GTLLLLSGLSLLGTI (SEQ ID NO: 217) | TGTVIGLIIATPLLV (SEQ ID NO: 218) |
| IFFLILFLAQEYGVE (SEQ ID NO: 219) | TPLFILFSPVIVPAI (SEQ ID NO: 220) | IFFLVLFLAQEGVVK (SEQ ID NO: 221) |
| TPLLVIFSPILVPAA (SEQ ID NO: 222) | IFSGFTPEFLEQAFQ (SEQ ID NO: 223) | TPVFIFFSPVIVPAV (SEQ ID NO: 224) |
| IRQAIKFMTASTIGV (SEQ ID NO: 225) | TPVFTFF SPVIVPAV (SEQ ID NO: 226) | KLSILVALLGALLW (SEQ ID NO: 227) |
| TTPLFILFSPVIVPA (SEQ ID NO: 228) | LMSLSWMINFIRQVH (SEQ ID NO: 229) | TVIGLIIATPLLVIF (SEQ ID NO: 230) |
| LNLLILRWLGLSAEY (SEQ ID NO: 231) | VKLSILVALLGALLV (SEQ ID NO: 232) | LSSFSWVMNYIRQTH (SEQ ID NO: 233) |

We claim:

1. A peptide comprising a sequence of $X_1X_2X_3X_4X_5X_6X_7X_8X_9X_{10}X_{11}X_{12}X_{13}X_{14}X_{15}$ (SEQ ID NO: 1); wherein:

$X_1$ is E;

$X_2$ is T;

$X_3$ is Q or P;

$X_4$ is G;

$X_5$ is A or W;

$X_6$ is I;

$X_7$ is V;

$X_8$ is T;

$X_9$ is V;

$X_{10}$ is K;

$X_{11}$ is G or Q;

$X_{12}$ is G;

$X_{13}$ is L;

$X_{14}$ is R; and $X_{15}$ is I, H or W.

2. A pharmaceutical composition comprising the peptide of claim 1.

3. The peptide of claim 1, wherein $X_3$ is Q.

4. The peptide of claim 1, wherein $X_3$ is P.

5. The peptide of claim 1, wherein $X_5$ is A.

6. The peptide of claim 1, wherein $X_5$ is W.

7. The peptide of claim 1, wherein $X_{11}$ is G.

8. The peptide of claim 1, wherein $X_{11}$ is Q.

9. The peptide of claim 1, wherein $X_{15}$ is I.

10. The peptide of claim 1, wherein $X_{15}$ is H.

11. The peptide of claim 1, wherein $X_{15}$ is W.

12. The peptide of claim 1, wherein $X_3$ is P, $X_5$ is W, $X_{11}$ is Q and $X_{15}$ is H.

* * * * *

SEQUENCE LISTING

<160> NUMBER OF SEQ ID NOS: 233

<210> SEQ ID NO 1
<211> LENGTH: 15
<212> TYPE: PRT

-continued

<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)
<223> OTHER INFORMATION: X1 is E
<220> FEATURE:
<221> NAME/KEY: MISC_FEATURE
<222> LOCATION: (2)..(2)
<223> OTHER INFORMATION: X2 is E or T
<220> FEATURE:
<221> NAME/KEY: MISC_FEATURE
<222> LOCATION: (3)..(3)
<223> OTHER INFORMATION: X3 is Q or P
<220> FEATURE:
<221> NAME/KEY: MISC_FEATURE
<222> LOCATION: (4)..(4)
<223> OTHER INFORMATION: X4 is G
<220> FEATURE:
<221> NAME/KEY: MISC_FEATURE
<222> LOCATION: (5)..(5)
<223> OTHER INFORMATION: X5 is A or W
<220> FEATURE:
<221> NAME/KEY: MISC_FEATURE
<222> LOCATION: (6)..(6)
<223> OTHER INFORMATION: X6 is I
<220> FEATURE:
<221> NAME/KEY: MISC_FEATURE
<222> LOCATION: (7)..(7)
<223> OTHER INFORMATION: X7 is V
<220> FEATURE:
<221> NAME/KEY: MISC_FEATURE
<222> LOCATION: (8)..(8)
<223> OTHER INFORMATION: X8 is T
<220> FEATURE:
<221> NAME/KEY: MISC_FEATURE
<222> LOCATION: (9)..(9)
<223> OTHER INFORMATION: X9 is V
<220> FEATURE:
<221> NAME/KEY: MISC_FEATURE
<222> LOCATION: (10)..(10)
<223> OTHER INFORMATION: X10 is K
<220> FEATURE:
<221> NAME/KEY: MISC_FEATURE
<222> LOCATION: (11)..(11)
<223> OTHER INFORMATION: X11 is G or Q
<220> FEATURE:
<221> NAME/KEY: MISC_FEATURE
<222> LOCATION: (12)..(12)
<223> OTHER INFORMATION: X12 is G
<220> FEATURE:
<221> NAME/KEY: MISC_FEATURE
<222> LOCATION: (13)..(13)
<223> OTHER INFORMATION: X13 is L
<220> FEATURE:
<221> NAME/KEY: MISC_FEATURE
<222> LOCATION: (14)..(14)
<223> OTHER INFORMATION: X14 is R
<220> FEATURE:
<221> NAME/KEY: MISC_FEATURE
<222> LOCATION: (15)..(15)
<223> OTHER INFORMATION: X15 is I, H or W

<400> SEQUENCE: 1

```
Xaa Xaa Xaa Xaa Xaa Xaa Xaa Xaa Xaa Xaa Xaa Xaa Xaa Xaa Xaa
1               5                   10                  15
```

<210> SEQ ID NO 2
<211> LENGTH: 15
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (1)..(1)

-continued

<223> OTHER INFORMATION: X1 is N, A, C, D, F, G, H, L, M, P, R, S, T, W, or Y
<220> FEATURE:
<221> NAME/KEY: MISC_FEATURE
<222> LOCATION: (2)..(2)
<223> OTHER INFORMATION: X2 is Y, C, F, G, H, L, M, N, T, V, or W
<220> FEATURE:
<221> NAME/KEY: MISC_FEATURE
<222> LOCATION: (3)..(3)
<223> OTHER INFORMATION: X3 is A, C, E, F, G, H, I, K, L, Q, S, T, or Y
<220> FEATURE:
<221> NAME/KEY: MISC_FEATURE
<222> LOCATION: (4)..(4)
<223> OTHER INFORMATION: X4 is Y, C, D, F, H, I, K, L, M, N, Q, R, or S
<220> FEATURE:
<221> NAME/KEY: MISC_FEATURE
<222> LOCATION: (5)..(5)
<223> OTHER INFORMATION: X5 is N, A, D, H, I, K, L, M, P, Q, S, T, V, or W
<220> FEATURE:
<221> NAME/KEY: MISC_FEATURE
<222> LOCATION: (6)..(6)
<223> OTHER INFORMATION: X6 is Y, A, C, D, E, F, G, L, P, R, T, V, or W
<220> FEATURE:
<221> NAME/KEY: MISC_FEATURE
<222> LOCATION: (7)..(7)
<223> OTHER INFORMATION: X7 is S, A, C, F, I, L, N, P, Q, R, T, V, W, or Y
<220> FEATURE:
<221> NAME/KEY: MISC_FEATURE
<222> LOCATION: (8)..(8)
<223> OTHER INFORMATION: X8 is V, A, E, H, I, K, L, M, P, Q, R, W, or Y
<220> FEATURE:
<221> NAME/KEY: MISC_FEATURE
<222> LOCATION: (9)..(9)
<223> OTHER INFORMATION: X9 is V, A, C, D, E, F, G, H, K, L, N, Q, T, or W
<220> FEATURE:
<221> NAME/KEY: MISC_FEATURE
<222> LOCATION: (10)..(10)
<223> OTHER INFORMATION: X10 is G, A, E, F, H, I, K, L, N, P, Q, R, S, V, or Y
<220> FEATURE:
<221> NAME/KEY: MISC_FEATURE
<222> LOCATION: (11)..(11)
<223> OTHER INFORMATION: X11 is G, A, C, F, I, K, L, M, N, Q, R, S, T, V, W, or Y
<220> FEATURE:
<221> NAME/KEY: MISC_FEATURE
<222> LOCATION: (12)..(12)
<223> OTHER INFORMATION: X12 is V, A, D, E, H, K, M, N, S, or W
<220> FEATURE:
<221> NAME/KEY: MISC_FEATURE
<222> LOCATION: (13)..(13)
<223> OTHER INFORMATION: X13 is A, C, D, G, H, L, P, R, S, V, Y, or L
<220> FEATURE:
<221> NAME/KEY: MISC_FEATURE
<222> LOCATION: (14)..(14)
<223> OTHER INFORMATION: X14 is L, A, D, F, G, H, M, N, P, R, S, T, W, or Y
<220> FEATURE:
<221> NAME/KEY: MISC_FEATURE
<222> LOCATION: (15)..(15)
<223> OTHER INFORMATION: X15 is P, D, F, H, I, K, M, T, or W

<400> SEQUENCE: 2

```
Xaa Xaa Xaa Xaa Xaa Xaa Xaa Xaa Xaa Xaa Xaa Xaa Xaa Xaa Xaa
1               5                   10                  15
```

<210> SEQ ID NO 3
<211> LENGTH: 15
<212> TYPE: PRT
<213> ORGANISM: Artificial Sequence
<220> FEATURE:
<223> OTHER INFORMATION: Synthetic sequence

<400> SEQUENCE: 3

Glu Glu Gln Gly Ala Ile Val Thr Val Lys Gly Gly Leu Arg Ile
1 5 10 15

<210> SEQ ID NO 4
<211> LENGTH: 15
<212> TYPE: PRT
<213> ORGANISM: Artificial Sequence
<220> FEATURE:
<223> OTHER INFORMATION: Synthetic sequence

<400> SEQUENCE: 4

Glu Thr Pro Gly Trp Ile Val Thr Val Lys Gly Gly Leu Arg Ile
1 5 10 15

<210> SEQ ID NO 5
<211> LENGTH: 12
<212> TYPE: PRT
<213> ORGANISM: Artificial Sequence
<220> FEATURE:
<223> OTHER INFORMATION: Synthetic sequence

<400> SEQUENCE: 5

Gln Gly Ala Leu Ala Asn Ile Ala Val Asp Lys Ala
1 5 10

<210> SEQ ID NO 6
<211> LENGTH: 6
<212> TYPE: PRT
<213> ORGANISM: Artificial Sequence
<220> FEATURE:
<223> OTHER INFORMATION: Synthetic sequence

<400> SEQUENCE: 6

Lys Gln Asn Thr Leu Lys
1 5

<210> SEQ ID NO 7
<211> LENGTH: 15
<212> TYPE: PRT
<213> ORGANISM: Artificial Sequence
<220> FEATURE:
<223> OTHER INFORMATION: Synthetic sequence (epitope Arah14)

<400> SEQUENCE: 7

Gly Thr Ile Ile Gly Leu Ala Ile Ala Thr Pro Val Phe Thr Phe
1 5 10 15

<210> SEQ ID NO 8
<211> LENGTH: 14
<212> TYPE: PRT
<213> ORGANISM: Artificial Sequence
<220> FEATURE:
<223> OTHER INFORMATION: Synthetic sequence (epitope Arah14)

<400> SEQUENCE: 8

Thr Met Leu Gly Leu Ala Met Ala Thr Ala Pro Val Phe Thr
1 5 10

<210> SEQ ID NO 9
<211> LENGTH: 9
<212> TYPE: PRT
<213> ORGANISM: Artificial Sequence
<220> FEATURE:
<223> OTHER INFORMATION: Synthetic sequence (epitope Arah14)

<400> SEQUENCE: 9

```
Ile Gly Leu Ala Ile Ala Thr Pro Val
1               5


<210> SEQ ID NO 10
<211> LENGTH: 13
<212> TYPE: PRT
<213> ORGANISM: Artificial Sequence
<220> FEATURE:
<223> OTHER INFORMATION: Synthetic sequence (epitope Arah14)

<400> SEQUENCE: 10

Thr Ile Ile Gly Leu Ala Ile Ala Thr Pro Val Phe Thr
1               5                   10


<210> SEQ ID NO 11
<211> LENGTH: 15
<212> TYPE: PRT
<213> ORGANISM: Artificial Sequence
<220> FEATURE:
<223> OTHER INFORMATION: Synthetic sequence (epitope Arah14)

<400> SEQUENCE: 11

Leu Gly Thr Ile Ile Gly Leu Ala Ile Ala Thr Pro Val Phe Thr
1               5                   10                  15


<210> SEQ ID NO 12
<211> LENGTH: 13
<212> TYPE: PRT
<213> ORGANISM: Artificial Sequence
<220> FEATURE:
<223> OTHER INFORMATION: Synthetic sequence (epitope Arah14)

<400> SEQUENCE: 12

Thr Ile Ile Gly Leu Ala Ile Ala Thr Pro Val Phe Thr
1               5                   10


<210> SEQ ID NO 13
<211> LENGTH: 14
<212> TYPE: PRT
<213> ORGANISM: Artificial Sequence
<220> FEATURE:
<223> OTHER INFORMATION: Synthetic sequence (epitope Arah14)

<400> SEQUENCE: 13

Thr Met Leu Gly Leu Ala Met Ala Thr Ala Pro Val Phe Thr
1               5                   10


<210> SEQ ID NO 14
<211> LENGTH: 9
<212> TYPE: PRT
<213> ORGANISM: Artificial Sequence
<220> FEATURE:
<223> OTHER INFORMATION: Synthetic sequence (epitope Arah14)

<400> SEQUENCE: 14

Ile Gly Leu Ala Ile Ala Thr Pro Val
1               5


<210> SEQ ID NO 15
<211> LENGTH: 15
<212> TYPE: PRT
<213> ORGANISM: Artificial Sequence
<220> FEATURE:
<223> OTHER INFORMATION: Synthetic sequence (epitope Arah14)

<400> SEQUENCE: 15

Thr Ile Ile Gly Leu Ala Ile Ala Thr Pro Val Phe Thr Phe Phe
```

1 5 10 15

<210> SEQ ID NO 16
<211> LENGTH: 13
<212> TYPE: PRT
<213> ORGANISM: Artificial Sequence
<220> FEATURE:
<223> OTHER INFORMATION: Synthetic sequence (epitope Arah14)

<400> SEQUENCE: 16

Thr Ile Ile Gly Leu Ala Ile Ala Thr Pro Val Phe Thr
1 5 10

<210> SEQ ID NO 17
<211> LENGTH: 14
<212> TYPE: PRT
<213> ORGANISM: Artificial Sequence
<220> FEATURE:
<223> OTHER INFORMATION: Synthetic sequence (epitope Arah14)

<400> SEQUENCE: 17

Thr Met Leu Gly Leu Ala Met Ala Thr Ala Pro Val Phe Thr
1 5 10

<210> SEQ ID NO 18
<211> LENGTH: 9
<212> TYPE: PRT
<213> ORGANISM: Artificial Sequence
<220> FEATURE:
<223> OTHER INFORMATION: Synthetic sequence (epitope Arah14)

<400> SEQUENCE: 18

Ile Gly Leu Ala Ile Ala Thr Pro Val
1 5

<210> SEQ ID NO 19
<211> LENGTH: 15
<212> TYPE: PRT
<213> ORGANISM: Artificial Sequence
<220> FEATURE:
<223> OTHER INFORMATION: Synthetic sequence (epitope Arah3)

<400> SEQUENCE: 19

Ala Gly Val Ala Leu Ser Arg Leu Val Leu Arg Arg Asn Ala Leu
1 5 10 15

<210> SEQ ID NO 20
<211> LENGTH: 14
<212> TYPE: PRT
<213> ORGANISM: Artificial Sequence
<220> FEATURE:
<223> OTHER INFORMATION: Synthetic sequence (epitope Arah3)

<400> SEQUENCE: 20

Ala Gly Val Ala Leu Ser Arg Leu Val Leu Arg Arg Asn Ala
1 5 10

<210> SEQ ID NO 21
<211> LENGTH: 14
<212> TYPE: PRT
<213> ORGANISM: Artificial Sequence
<220> FEATURE:
<223> OTHER INFORMATION: Synthetic sequence (epitope Arah3)

<400> SEQUENCE: 21

Ala Ser Val Ala Leu Ala Arg Leu Val Ala Arg Arg Gly Ala
1 5 10

<210> SEQ ID NO 22
<211> LENGTH: 9
<212> TYPE: PRT
<213> ORGANISM: Artificial Sequence
<220> FEATURE:
<223> OTHER INFORMATION: Synthetic sequence (epitope Arah3)

<400> SEQUENCE: 22

Leu Ser Arg Leu Val Leu Arg Arg Asn
1               5

<210> SEQ ID NO 23
<211> LENGTH: 15
<212> TYPE: PRT
<213> ORGANISM: Artificial Sequence
<220> FEATURE:
<223> OTHER INFORMATION: Synthetic sequence (epitope Arah3)

<400> SEQUENCE: 23

Cys Ala Gly Val Ala Leu Ser Arg Leu Val Leu Arg Arg Asn Ala
1               5                   10                  15

<210> SEQ ID NO 24
<211> LENGTH: 14
<212> TYPE: PRT
<213> ORGANISM: Artificial Sequence
<220> FEATURE:
<223> OTHER INFORMATION: Synthetic sequence (epitope Arah3)

<400> SEQUENCE: 24

Ala Gly Val Ala Leu Ser Arg Leu Val Leu Arg Arg Asn Ala
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Synthetic sequence (epitope Arah3)

<400> SEQUENCE: 25

Ala Ser Val Ala Leu Ala Arg Leu Val Ala Arg Arg Gly Ala
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Synthetic sequence (epitope Arah3)

<400> SEQUENCE: 26

Leu Ser Arg Leu Val Leu Arg Arg Asn
1               5

<210> SEQ ID NO 27
<211> LENGTH: 15
<212> TYPE: PRT
<213> ORGANISM: Artificial Sequence
<220> FEATURE:
<223> OTHER INFORMATION: Synthetic sequence (epitope Arah15)

<400> SEQUENCE: 27

Pro Ala Ala Ile Thr Leu Ala Leu Ala Ala Gly Gly Phe Leu Phe
1               5                   10                  15

<210> SEQ ID NO 28
<211> LENGTH: 10
<212> TYPE: PRT
<213> ORGANISM: Artificial Sequence
<220> FEATURE:
<223> OTHER INFORMATION: Synthetic sequence (epitope Arah15)

<400> SEQUENCE: 28

Ile Thr Leu Ala Leu Ala Ala Gly Gly Phe
1 5 10

<210> SEQ ID NO 29
<211> LENGTH: 11
<212> TYPE: PRT
<213> ORGANISM: Artificial Sequence
<220> FEATURE:
<223> OTHER INFORMATION: Synthetic sequence (epitope Arah15)

<400> SEQUENCE: 29

Ile Ser Leu Ala Leu Leu Ala Ala Gly Gly Phe
1 5 10

<210> SEQ ID NO 30
<211> LENGTH: 9
<212> TYPE: PRT
<213> ORGANISM: Artificial Sequence
<220> FEATURE:
<223> OTHER INFORMATION: Synthetic sequence (epitope Arah15)

<400> SEQUENCE: 30

Ile Thr Leu Ala Leu Ala Ala Gly Gly
1 5

<210> SEQ ID NO 31
<211> LENGTH: 15
<212> TYPE: PRT
<213> ORGANISM: Artificial Sequence
<220> FEATURE:
<223> OTHER INFORMATION: Synthetic sequence (epitope Arah3)

<400> SEQUENCE: 31

Gly Val Ala Leu Ser Arg Leu Val Leu Arg Arg Asn Ala Leu Arg
1 5 10 15

<210> SEQ ID NO 32
<211> LENGTH: 12
<212> TYPE: PRT
<213> ORGANISM: Artificial Sequence
<220> FEATURE:
<223> OTHER INFORMATION: Synthetic sequence (epitope Arah3)

<400> SEQUENCE: 32

Val Ala Leu Ser Arg Leu Val Leu Arg Arg Asn Ala
1 5 10

<210> SEQ ID NO 33
<211> LENGTH: 12
<212> TYPE: PRT
<213> ORGANISM: Artificial Sequence
<220> FEATURE:
<223> OTHER INFORMATION: Synthetic sequence (epitope Arah3)

<400> SEQUENCE: 33

Val Ala Leu Ala Arg Leu Val Ala Arg Arg Gly Ala
1 5 10

<210> SEQ ID NO 34
<211> LENGTH: 9
<212> TYPE: PRT
<213> ORGANISM: Artificial Sequence
<220> FEATURE:
<223> OTHER INFORMATION: Synthetic sequence (epitope Arah3)

<400> SEQUENCE: 34

Leu Val Leu Arg Arg Asn Ala Leu Arg
1               5

<210> SEQ ID NO 35
<211> LENGTH: 15
<212> TYPE: PRT
<213> ORGANISM: Artificial Sequence
<220> FEATURE:
<223> OTHER INFORMATION: Synthetic sequence (epitope Arah3)

<400> SEQUENCE: 35

Val Ala Leu Ser Arg Leu Val Leu Arg Arg Asn Ala Leu Arg Arg
1               5                   10                  15

<210> SEQ ID NO 36
<211> LENGTH: 12
<212> TYPE: PRT
<213> ORGANISM: Artificial Sequence
<220> FEATURE:
<223> OTHER INFORMATION: Synthetic sequence (epitope Arah3)

<400> SEQUENCE: 36

Val Ala Leu Ser Arg Leu Val Leu Arg Arg Asn Ala
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic sequence (epitope Arah3)

<400> SEQUENCE: 37

Val Ala Leu Ala Arg Leu Val Ala Arg Arg Gly Ala
1               5                   10

<210> SEQ ID NO 38
<211> LENGTH: 9
<212> TYPE: PRT
<213> ORGANISM: Artificial Sequence
<220> FEATURE:
<223> OTHER INFORMATION: Synthetic sequence (epitope Arah3)

<400> SEQUENCE: 38

Leu Val Leu Arg Arg Asn Ala Leu Arg
1               5

<210> SEQ ID NO 39
<211> LENGTH: 15
<212> TYPE: PRT
<213> ORGANISM: Artificial Sequence
<220> FEATURE:
<223> OTHER INFORMATION: Synthetic sequence (epitope Arah)

<400> SEQUENCE: 39

Leu Leu Gly Ile Leu Val Leu Ala Ser Val Ser Ala Thr His Ala
1               5                   10                  15

<210> SEQ ID NO 40

<211> LENGTH: 12
<212> TYPE: PRT
<213> ORGANISM: Artificial Sequence
<220> FEATURE:
<223> OTHER INFORMATION: Synthetic sequence (epitope Arah)

<400> SEQUENCE: 40

Leu Leu Gly Ile Leu Val Leu Ala Ser Val Ser Ala
1 5 10

<210> SEQ ID NO 41
<211> LENGTH: 12
<212> TYPE: PRT
<213> ORGANISM: Artificial Sequence
<220> FEATURE:
<223> OTHER INFORMATION: Synthetic sequence (epitope Arah)

<400> SEQUENCE: 41

Leu Leu Gly Leu Leu Val Ile Ala Leu Val Ser Ala
1 5 10

<210> SEQ ID NO 42
<211> LENGTH: 9
<212> TYPE: PRT
<213> ORGANISM: Artificial Sequence
<220> FEATURE:
<223> OTHER INFORMATION: Synthetic sequence (epitope Arah)

<400> SEQUENCE: 42

Ile Leu Val Leu Ala Ser Val Ser Ala
1 5

<210> SEQ ID NO 43
<211> LENGTH: 15
<212> TYPE: PRT
<213> ORGANISM: Artificial Sequence
<220> FEATURE:
<223> OTHER INFORMATION: Synthetic sequence (epitope Agglutinin_L ECG)

<400> SEQUENCE: 43

Gly Asn Val Ala Ser Phe Leu Thr Ser Phe Ser Phe Glu Met Lys
1 5 10 15

<210> SEQ ID NO 44
<211> LENGTH: 12
<212> TYPE: PRT
<213> ORGANISM: Artificial Sequence
<220> FEATURE:
<223> OTHER INFORMATION: Synthetic sequence (epitope Agglutinin_L ECG)

<400> SEQUENCE: 44

Gly Asn Val Ala Ser Phe Leu Thr Ser Phe Ser Phe
1 5 10

<210> SEQ ID NO 45
<211> LENGTH: 11
<212> TYPE: PRT
<213> ORGANISM: Artificial Sequence
<220> FEATURE:
<223> OTHER INFORMATION: Synthetic sequence (epitope Agglutinin_L ECG)

<400> SEQUENCE: 45

Gly Glu Val Ala Asp Ile Thr Ser Phe Ser Phe
1 5 10

<210> SEQ ID NO 46
<211> LENGTH: 9

<212> TYPE: PRT
<213> ORGANISM: Artificial Sequence
<220> FEATURE:
<223> OTHER INFORMATION: Synthetic sequence (epitope Agglutinin_L ECG)

<400> SEQUENCE: 46

Phe Leu Thr Ser Phe Ser Phe Glu Met
1               5

<210> SEQ ID NO 47
<211> LENGTH: 15
<212> TYPE: PRT
<213> ORGANISM: Artificial Sequence
<220> FEATURE:
<223> OTHER INFORMATION: Synthetic sequence (epitope Agglutinin_L ECG)

<400> SEQUENCE: 47

Thr Gly Asn Val Ala Ser Phe Leu Thr Ser Phe Ser Phe Glu Met
1               5                   10                  15

<210> SEQ ID NO 48
<211> LENGTH: 12
<212> TYPE: PRT
<213> ORGANISM: Artificial Sequence
<220> FEATURE:
<223> OTHER INFORMATION: Synthetic sequence (epitope Agglutinin_L ECG)

<400> SEQUENCE: 48

Gly Asn Val Ala Ser Phe Leu Thr Ser Phe Ser Phe
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic sequence (epitope Agglutinin_L ECG)

<400> SEQUENCE: 49

Gly Glu Val Ala Asp Phe Thr Ser Phe Ser Phe
1               5                   10

<210> SEQ ID NO 50
<211> LENGTH: 9
<212> TYPE: PRT
<213> ORGANISM: Artificial Sequence
<220> FEATURE:
<223> OTHER INFORMATION: Synthetic sequence (epitope Agglutinin_L ECG)

<400> SEQUENCE: 50

Phe Leu Thr Ser Phe Ser Glu Glu Met
1               5

<210> SEQ ID NO 51
<211> LENGTH: 15
<212> TYPE: PRT
<213> ORGANISM: Artificial Sequence
<220> FEATURE:
<223> OTHER INFORMATION: Synthetic sequence (epitope Arah8)

<400> SEQUENCE: 51

Ala Asn Tyr Ala Tyr Asn Tyr Ser Val Val Gly Gly Val Ala Leu
1               5                   10                  15

<210> SEQ ID NO 52
<211> LENGTH: 12
<212> TYPE: PRT

<213> ORGANISM: Artificial Sequence
<220> FEATURE:
<223> OTHER INFORMATION: Synthetic sequence (epitope Arah8)

<400> SEQUENCE: 52

Ala Tyr Asn Tyr Ser Val Val Gly Gly Val Ala Leu
1 5 10

<210> SEQ ID NO 53
<211> LENGTH: 12
<212> TYPE: PRT
<213> ORGANISM: Artificial Sequence
<220> FEATURE:
<223> OTHER INFORMATION: Synthetic sequence (epitope Arah8)

<400> SEQUENCE: 53

Ala Tyr Gly Tyr Ala Val Val Leu Gly Val Ala Leu
1 5 10

<210> SEQ ID NO 54
<211> LENGTH: 9
<212> TYPE: PRT
<213> ORGANISM: Artificial Sequence
<220> FEATURE:
<223> OTHER INFORMATION: Synthetic sequence (epitope Arah8)

<400> SEQUENCE: 54

Tyr Asn Tyr Ser Val Val Gly Gly Val
1 5

<210> SEQ ID NO 55
<211> LENGTH: 15
<212> TYPE: PRT
<213> ORGANISM: Artificial Sequence
<220> FEATURE:
<223> OTHER INFORMATION: Synthetic sequence (epitope Arah8)

<400> SEQUENCE: 55

Asn Tyr Ala Tyr Asn Tyr Ser Val Val Gly Gly Val Ala Leu Pro
1 5 10 15

<210> SEQ ID NO 56
<211> LENGTH: 12
<212> TYPE: PRT
<213> ORGANISM: Artificial Sequence
<220> FEATURE:
<223> OTHER INFORMATION: Synthetic sequence (epitope Arah8)

<400> SEQUENCE: 56

Ala Tyr Asn Tyr Ser Val Val Gly Gly Val Ala Leu
1 5 10

<210> SEQ ID NO 57
<211> LENGTH: 12
<212> TYPE: PRT
<213> ORGANISM: Artificial Sequence
<220> FEATURE:
<223> OTHER INFORMATION: Synthetic sequence (epitope Arah8)

<400> SEQUENCE: 57

Ala Tyr Gly Tyr Ala Val Val Leu Gly Val Ala Leu
1 5 10

<210> SEQ ID NO 58
<211> LENGTH: 9
<212> TYPE: PRT
<213> ORGANISM: Artificial Sequence
<220> FEATURE:
<223> OTHER INFORMATION: Synthetic sequence (epitope Arah8)

<400> SEQUENCE: 58

Tyr Asn Tyr Ser Val Val Gly Gly Val
1 5

<210> SEQ ID NO 59
<211> LENGTH: 15
<212> TYPE: PRT
<213> ORGANISM: Artificial Sequence
<220> FEATURE:
<223> OTHER INFORMATION: Synthetic sequence (epitope Arah3)

<400> SEQUENCE: 59

Glu Glu Gln Gly Ala Ile Val Thr Val Arg Gly Gly Leu Arg Ile
1 5 10 15

<210> SEQ ID NO 60
<211> LENGTH: 11
<212> TYPE: PRT
<213> ORGANISM: Artificial Sequence
<220> FEATURE:
<223> OTHER INFORMATION: Synthetic sequence (epitope Arah3)

<400> SEQUENCE: 60

Gln Gly Ala Ile Val Thr Val Arg Gly Gly Leu
1 5 10

<210> SEQ ID NO 61
<211> LENGTH: 10
<212> TYPE: PRT
<213> ORGANISM: Artificial Sequence
<220> FEATURE:
<223> OTHER INFORMATION: Synthetic sequence (epitope Arah3)

<400> SEQUENCE: 61

Gln Gly Ile Leu Thr Val Arg Gly Gly Met
1 5 10

<210> SEQ ID NO 62
<211> LENGTH: 9
<212> TYPE: PRT
<213> ORGANISM: Artificial Sequence
<220> FEATURE:
<223> OTHER INFORMATION: Synthetic sequence (epitope Arah3)

<400> SEQUENCE: 62

Ile Leu Thr Val Arg Gly Gly Leu Arg
1 5

<210> SEQ ID NO 63
<211> LENGTH: 14
<212> TYPE: PRT
<213> ORGANISM: Artificial Sequence
<220> FEATURE:
<223> OTHER INFORMATION: Synthetic sequence (epitope Arah3)

<400> SEQUENCE: 63

Glu Gln Gly Ala Val Thr Val Arg Gly Gly Leu Arg Ile Leu
1 5 10

<210> SEQ ID NO 64
<211> LENGTH: 11
<212> TYPE: PRT
<213> ORGANISM: Artificial Sequence
<220> FEATURE:

<223> OTHER INFORMATION: Synthetic sequence (epitope Arah3)

<400> SEQUENCE: 64

Gln Gly Ala Ile Val Thr Val Arg Gly Gly Leu
1 5 10

<210> SEQ ID NO 65
<211> LENGTH: 10
<212> TYPE: PRT
<213> ORGANISM: Artificial Sequence
<220> FEATURE:
<223> OTHER INFORMATION: Synthetic sequence (epitope Arah3)

<400> SEQUENCE: 65

Gln Gly Ile Leu Thr Val Arg Gly Gly Met
1 5 10

<210> SEQ ID NO 66
<211> LENGTH: 9
<212> TYPE: PRT
<213> ORGANISM: Artificial Sequence
<220> FEATURE:
<223> OTHER INFORMATION: Synthetic sequence (epitope Arah3)

<400> SEQUENCE: 66

Ile Val Ile Asn Arg Gly Gly Leu Arg
1 5

<210> SEQ ID NO 67
<211> LENGTH: 14
<212> TYPE: PRT
<213> ORGANISM: Artificial Sequence
<220> FEATURE:
<223> OTHER INFORMATION: Synthetic sequence (epitope Arah3)

<400> SEQUENCE: 67

Gln Gly Ala Ile Val Thr Val Arg Gly Gly Leu Arg Leu Ser
1 5 10

<210> SEQ ID NO 68
<211> LENGTH: 11
<212> TYPE: PRT
<213> ORGANISM: Artificial Sequence
<220> FEATURE:
<223> OTHER INFORMATION: Synthetic sequence (epitope Arah3)

<400> SEQUENCE: 68

Gln Gly Ala Ile Val Thr Val Arg Gly Gly Leu
1 5 10

<210> SEQ ID NO 69
<211> LENGTH: 10
<212> TYPE: PRT
<213> ORGANISM: Artificial Sequence
<220> FEATURE:
<223> OTHER INFORMATION: Synthetic sequence (epitope Arah3)

<400> SEQUENCE: 69

Gln Gly Ile Leu Thr Val Arg Gly Gly Met
1 5 10

<210> SEQ ID NO 70
<211> LENGTH: 9
<212> TYPE: PRT
<213> ORGANISM: Artificial Sequence
<220> FEATURE:
<223> OTHER INFORMATION: Synthetic sequence (epitope Arah3)

<400> SEQUENCE: 70

Ile Leu Thr Val Arg Gly Gly Leu Arg
1 5

<210> SEQ ID NO 71
<211> LENGTH: 15
<212> TYPE: PRT
<213> ORGANISM: Artificial Sequence
<220> FEATURE:
<223> OTHER INFORMATION: Synthetic sequence (epitope Arah15)

<400> SEQUENCE: 71

Phe Ser Gly Gly Cys Gly Val Ala Ala Ile Ala Ala Leu Ser Trp
1 5 10 15

<210> SEQ ID NO 72
<211> LENGTH: 9
<212> TYPE: PRT
<213> ORGANISM: Artificial Sequence
<220> FEATURE:
<223> OTHER INFORMATION: Synthetic sequence (epitope Arah15)

<400> SEQUENCE: 72

Phe Ser Gly Gly Cys Gly Val Ala Ala
1 5

<210> SEQ ID NO 73
<211> LENGTH: 10
<212> TYPE: PRT
<213> ORGANISM: Artificial Sequence
<220> FEATURE:
<223> OTHER INFORMATION: Synthetic sequence (epitope Arah15)

<400> SEQUENCE: 73

Phe Ser Gly Gly Cys Ile Gly Val Ser Ala
1 5 10

<210> SEQ ID NO 74
<211> LENGTH: 9
<212> TYPE: PRT
<213> ORGANISM: Artificial Sequence
<220> FEATURE:
<223> OTHER INFORMATION: Synthetic sequence (epitope Arah15)

<400> SEQUENCE: 74

Gly Val Ala Ala Ile Ala Ala Leu Ser
1 5

<210> SEQ ID NO 75
<211> LENGTH: 15
<212> TYPE: PRT
<213> ORGANISM: Artificial Sequence
<220> FEATURE:
<223> OTHER INFORMATION: Synthetic sequence (epitope Arah15)

<400> SEQUENCE: 75

Ala Gly Gly Phe Leu Phe Ser Gly Gly Cys Gly Val Ala Ala Ile
1 5 10 15

<210> SEQ ID NO 76
<211> LENGTH: 12
<212> TYPE: PRT
<213> ORGANISM: Artificial Sequence
<220> FEATURE:
<223> OTHER INFORMATION: Synthetic sequence (epitope Arah15)

<400> SEQUENCE: 76

Gly Phe Leu Phe Ser Gly Gly Cys Gly Val Ala Ala
1 5 10

<210> SEQ ID NO 77
<211> LENGTH: 13
<212> TYPE: PRT
<213> ORGANISM: Artificial Sequence
<220> FEATURE:
<223> OTHER INFORMATION: Synthetic sequence (epitope Arah15)

<400> SEQUENCE: 77

Gly Leu Leu Phe Ser Gly Gly Cys Ile Gly Val Ser Ala
1 5 10

<210> SEQ ID NO 78
<211> LENGTH: 9
<212> TYPE: PRT
<213> ORGANISM: Artificial Sequence
<220> FEATURE:
<223> OTHER INFORMATION: Synthetic sequence (epitope Arah15)

<400> SEQUENCE: 78

Phe Ser Gly Gly Cys Gly Val Ala Ala
1 5

<210> SEQ ID NO 79
<211> LENGTH: 15
<212> TYPE: PRT
<213> ORGANISM: Artificial Sequence
<220> FEATURE:
<223> OTHER INFORMATION: Synthetic sequence (epitope Arah15)

<400> SEQUENCE: 79

Gly Phe Leu Phe Ser Gly Gly Cys Gly Val Ala Ala Ile Ala Ala
1 5 10 15

<210> SEQ ID NO 80
<211> LENGTH: 12
<212> TYPE: PRT
<213> ORGANISM: Artificial Sequence
<220> FEATURE:
<223> OTHER INFORMATION: Synthetic sequence (epitope Arah15)

<400> SEQUENCE: 80

Gly Phe Leu Phe Ser Gly Gly Cys Gly Val Ala Ala
1 5 10

<210> SEQ ID NO 81
<211> LENGTH: 13
<212> TYPE: PRT
<213> ORGANISM: Artificial Sequence
<220> FEATURE:
<223> OTHER INFORMATION: Synthetic sequence (epitope Arah15)

<400> SEQUENCE: 81

Gly Leu Leu Phe Ser Gly Gly Cys Ile Gly Val Ser Ala
1 5 10

<210> SEQ ID NO 82
<211> LENGTH: 9
<212> TYPE: PRT
<213> ORGANISM: Artificial Sequence
<220> FEATURE:
<223> OTHER INFORMATION: Synthetic sequence (epitope Arah15)

<400> SEQUENCE: 82

Gly Cys Gly Val Ala Ala Ile Ala Ala
1 5

<210> SEQ ID NO 83
<211> LENGTH: 15
<212> TYPE: PRT
<213> ORGANISM: Artificial Sequence
<220> FEATURE:
<223> OTHER INFORMATION: Synthetic sequence (epitope Arah15)

<400> SEQUENCE: 83

Gly Gly Phe Leu Phe Ser Gly Gly Cys Gly Val Ala Ala Ile Ala
1 5 10 15

<210> SEQ ID NO 84
<211> LENGTH: 12
<212> TYPE: PRT
<213> ORGANISM: Artificial Sequence
<220> FEATURE:
<223> OTHER INFORMATION: Synthetic sequence (epitope Arah15)

<400> SEQUENCE: 84

Gly Phe Leu Phe Ser Gly Gly Cys Gly Val Ala Ala
1 5 10

<210> SEQ ID NO 85
<211> LENGTH: 13
<212> TYPE: PRT
<213> ORGANISM: Artificial Sequence
<220> FEATURE:
<223> OTHER INFORMATION: Synthetic sequence (epitope Arah15)

<400> SEQUENCE: 85

Gly Leu Leu Phe Ser Gly Gly Cys Ile Gly Val Ser Ala
1 5 10

<210> SEQ ID NO 86
<211> LENGTH: 9
<212> TYPE: PRT
<213> ORGANISM: Artificial Sequence
<220> FEATURE:
<223> OTHER INFORMATION: Synthetic sequence (epitope Arah15)

<400> SEQUENCE: 86

Ser Gly Gly Cys Gly Val Ala Ala Ile
1 5

<210> SEQ ID NO 87
<211> LENGTH: 15
<212> TYPE: PRT
<213> ORGANISM: Artificial Sequence
<220> FEATURE:
<223> OTHER INFORMATION: Synthetic sequence (epitope Arah15)

<400> SEQUENCE: 87

Leu Phe Ser Gly Gly Cys Gly Val Ala Ala Ile Ala Ala Leu Ser
1 5 10 15

<210> SEQ ID NO 88
<211> LENGTH: 10
<212> TYPE: PRT
<213> ORGANISM: Artificial Sequence
<220> FEATURE:
<223> OTHER INFORMATION: Synthetic sequence (epitope Arah15)

<400> SEQUENCE: 88

```
Leu Phe Ser Gly Gly Cys Gly Val Ala Ala
1               5                   10


<210> SEQ ID NO 89
<211> LENGTH: 11
<212> TYPE: PRT
<213> ORGANISM: Artificial Sequence
<220> FEATURE:
<223> OTHER INFORMATION: Synthetic sequence (epitope Arah15)

<400> SEQUENCE: 89

Leu Phe Ser Gly Gly Cys Ile Gly Val Ser Ala
1               5                   10


<210> SEQ ID NO 90
<211> LENGTH: 9
<212> TYPE: PRT
<213> ORGANISM: Artificial Sequence
<220> FEATURE:
<223> OTHER INFORMATION: Synthetic sequence (epitope Arah15)

<400> SEQUENCE: 90

Cys Gly Val Ala Ala Ile Ala Ala Leu
1               5


<210> SEQ ID NO 91
<211> LENGTH: 15
<212> TYPE: PRT
<213> ORGANISM: Artificial Sequence
<220> FEATURE:
<223> OTHER INFORMATION: Synthetic sequence (epitope Arah15)

<400> SEQUENCE: 91

Phe Leu Phe Ser Gly Gly Cys Gly Val Ala Ala Ile Ala Ala Leu
1               5                   10                  15


<210> SEQ ID NO 92
<211> LENGTH: 11
<212> TYPE: PRT
<213> ORGANISM: Artificial Sequence
<220> FEATURE:
<223> OTHER INFORMATION: Synthetic sequence (epitope Arah15)

<400> SEQUENCE: 92

Phe Leu Phe Ser Gly Gly Cys Gly Val Ala Ala
1               5                   10


<210> SEQ ID NO 93
<211> LENGTH: 12
<212> TYPE: PRT
<213> ORGANISM: Artificial Sequence
<220> FEATURE:
<223> OTHER INFORMATION: Synthetic sequence (epitope Arah15)

<400> SEQUENCE: 93

Leu Leu Phe Ser Gly Gly Cys Ile Gly Val Ser Ala
1               5                   10


<210> SEQ ID NO 94
<211> LENGTH: 9
<212> TYPE: PRT
<213> ORGANISM: Artificial Sequence
<220> FEATURE:
<223> OTHER INFORMATION: Synthetic sequence (epitope Arah15)

<400> SEQUENCE: 94

Phe Ser Gly Gly Cys Gly Val Ala Ala
```

1 5

<210> SEQ ID NO 95
<211> LENGTH: 15
<212> TYPE: PRT
<213> ORGANISM: Artificial Sequence
<220> FEATURE:
<223> OTHER INFORMATION: Synthetic sequence (epitope Arah1)

<400> SEQUENCE: 95

Leu Leu Gly Ile Leu Val Leu Ala Ser Val Ser Ala Thr His Ala
1 5 10 15

<210> SEQ ID NO 96
<211> LENGTH: 12
<212> TYPE: PRT
<213> ORGANISM: Artificial Sequence
<220> FEATURE:
<223> OTHER INFORMATION: Synthetic sequence (epitope Arah1)

<400> SEQUENCE: 96

Leu Leu Gly Ile Leu Val Leu Ala Ser Val Ser Ala
1 5 10

<210> SEQ ID NO 97
<211> LENGTH: 12
<212> TYPE: PRT
<213> ORGANISM: Artificial Sequence
<220> FEATURE:
<223> OTHER INFORMATION: Synthetic sequence (epitope Arah1)

<400> SEQUENCE: 97

Leu Leu Gly Leu Leu Val Leu Val Ile Val Ser Ala
1 5 10

<210> SEQ ID NO 98
<211> LENGTH: 9
<212> TYPE: PRT
<213> ORGANISM: Artificial Sequence
<220> FEATURE:
<223> OTHER INFORMATION: Synthetic sequence (epitope Arah1)

<400> SEQUENCE: 98

Ile Leu Val Leu Ala Ser Val Ser Ala
1 5

<210> SEQ ID NO 99
<211> LENGTH: 15
<212> TYPE: PRT
<213> ORGANISM: Artificial Sequence
<220> FEATURE:
<223> OTHER INFORMATION: Synthetic sequence (epitope Agglutinin_LECG)

<400> SEQUENCE: 99

Val Phe Leu Thr Phe Phe Leu Leu Leu Ala Ala Ser Ser Lys Lys
1 5 10 15

<210> SEQ ID NO 100
<211> LENGTH: 11
<212> TYPE: PRT
<213> ORGANISM: Artificial Sequence
<220> FEATURE:
<223> OTHER INFORMATION: Synthetic sequence (epitope Agglutinin_LECG)

<400> SEQUENCE: 100

Val Phe Leu Thr Phe Phe Leu Leu Leu Ala Ala
1 5 10

<210> SEQ ID NO 101
<211> LENGTH: 12
<212> TYPE: PRT
<213> ORGANISM: Artificial Sequence
<220> FEATURE:
<223> OTHER INFORMATION: Synthetic sequence (epitope Agglutinin_LECG)

<400> SEQUENCE: 101

Val Ile Leu Thr Phe Phe Phe Leu Ser Ile Ala Ala
1 5 10

<210> SEQ ID NO 102
<211> LENGTH: 9
<212> TYPE: PRT
<213> ORGANISM: Artificial Sequence
<220> FEATURE:
<223> OTHER INFORMATION: Synthetic sequence (epitope Agglutinin_LECG)

<400> SEQUENCE: 102

Phe Leu Leu Leu Ala Ala Ser Ser Lys
1 5

<210> SEQ ID NO 103
<211> LENGTH: 233
<212> TYPE: PRT
<213> ORGANISM: Artificial Sequence
<220> FEATURE:
<223> OTHER INFORMATION: Synthetic sequence
<220> FEATURE:
<221> NAME/KEY: MISC_FEATURE
<222> LOCATION: (18)..(18)
<223> OTHER INFORMATION: X = Selenocysteine

<400> SEQUENCE: 103

Ala Ile Pro Asp Asx Ile Asp Ile Cys His Ala Ile Asn Ile Ser Glu
1 5 10 15

Gln Xaa Glu Asn Cys Glu Gly Pro Leu Gly Ser Met Asp Glu His Lys
20 25 30

Ala Leu Gly Val Met Arg Thr Met Val Asp Ser Gly Gln Leu Thr Asp
35 40 45

Pro Glu Ser Ala Arg Gly Lys Leu Leu Gln Thr Ala Ala His Leu Phe
50 55 60

Arg Asn Lys Gly Phe Glu Arg Thr Thr Val Arg Asp Leu Ala Ser Ala
65 70 75 80

Val Gly Ile Gln Ser Gly Ser Ile Phe His His Phe Lys Ser Lys Asp
85 90 95

Glu Ile Leu Arg Ala Val Met Glu Glu Asn His Tyr Asn Thr Ala Met
100 105 110

Met Arg Ala Ser Leu Glu Glu Ala Ser Thr Val Arg Glu Arg Val Leu
115 120 125

Ala Leu Ile Arg Cys Glu Leu Gln Ser Ile Met Gly Gly Ser Gly Glu
130 135 140

Ala Met Ala Val Leu Val Tyr Glu Trp Arg Ser Leu Ser Ala Glu Gly
145 150 155 160

Gln Ala His Val Leu Ala Leu Arg Asp Val Tyr Glu Gln Ile Trp Leu
165 170 175

Gln Val Leu Gly Glu Ala Lys Ala Ala Gly Tyr Ile Arg Gly Asp Val
180 185 190

Phe Ile Thr Arg Arg Phe Leu Thr Gly Ala Leu Ser Trp Thr Thr Thr
195 200 205

Trp Phe Arg Ala Gln Gly Ser Leu Thr Leu Glu Glu Leu Ala Glu Glu
210 215 220

Ala Leu Leu Met Val Leu Lys Ser Asp
225 230

<210> SEQ ID NO 104
<211> LENGTH: 15
<212> TYPE: PRT
<213> ORGANISM: Artificial Sequence
<220> FEATURE:
<223> OTHER INFORMATION: Synthetic sequence

<400> SEQUENCE: 104

Glu Glu Thr Ile His Tyr Asn Thr Ala Met Met Arg Ala Ser Leu
1 5 10 15

<210> SEQ ID NO 105
<211> LENGTH: 15
<212> TYPE: PRT
<213> ORGANISM: Artificial Sequence
<220> FEATURE:
<223> OTHER INFORMATION: Synthetic sequence

<400> SEQUENCE: 105

Met Glu Glu Thr Ile His Tyr Asn Thr Ala Met Met Arg Ala Ser
1 5 10 15

<210> SEQ ID NO 106
<211> LENGTH: 15
<212> TYPE: PRT
<213> ORGANISM: Artificial Sequence
<220> FEATURE:
<223> OTHER INFORMATION: Synthetic sequence

<400> SEQUENCE: 106

Glu Thr Ile His Tyr Asn Thr Ala Met Met Arg Ala Ser Leu Glu
1 5 10 15

<210> SEQ ID NO 107
<211> LENGTH: 15
<212> TYPE: PRT
<213> ORGANISM: Artificial Sequence
<220> FEATURE:
<223> OTHER INFORMATION: Synthetic sequence

<400> SEQUENCE: 107

Val Met Glu Glu Thr Ile His Tyr Asn Thr Ala Met Met Arg Ala
1 5 10 15

<210> SEQ ID NO 108
<211> LENGTH: 15
<212> TYPE: PRT
<213> ORGANISM: Artificial Sequence
<220> FEATURE:
<223> OTHER INFORMATION: Synthetic sequence

<400> SEQUENCE: 108

Arg Gly Lys Leu Leu Gln Thr Ala Ala His Leu Phe Arg Asn Lys
1 5 10 15

<210> SEQ ID NO 109
<211> LENGTH: 12
<212> TYPE: PRT
<213> ORGANISM: Artificial Sequence
<220> FEATURE:
<223> OTHER INFORMATION: Synthetic sequence

<400> SEQUENCE: 109

Glu Thr Ile His Tyr Asn Thr Ala Met Met Arg Ala
1 5 10

<210> SEQ ID NO 110
<211> LENGTH: 12
<212> TYPE: PRT
<213> ORGANISM: Artificial Sequence
<220> FEATURE:
<223> OTHER INFORMATION: Synthetic sequence

<400> SEQUENCE: 110

Gln Gly Ala Leu Ala Asn Ile Ala Val Asp Lys Ala
1 5 10

<210> SEQ ID NO 111
<211> LENGTH: 6
<212> TYPE: PRT
<213> ORGANISM: Artificial Sequence
<220> FEATURE:
<223> OTHER INFORMATION: Synthetic sequence

<400> SEQUENCE: 111

Lys Gln Asn Thr Leu Lys
1 5

<210> SEQ ID NO 112
<211> LENGTH: 12
<212> TYPE: PRT
<213> ORGANISM: Artificial Sequence
<220> FEATURE:
<223> OTHER INFORMATION: Synthetic sequence

<400> SEQUENCE: 112

Gln Gly Ala Leu Ala Asn Ile Ala Val Asp Lys Phe
1 5 10

<210> SEQ ID NO 113
<211> LENGTH: 12
<212> TYPE: PRT
<213> ORGANISM: Artificial Sequence
<220> FEATURE:
<223> OTHER INFORMATION: Synthetic sequence

<400> SEQUENCE: 113

Pro Trp Ala Leu Ala Asn Ile Ala Val Asp Lys Ala
1 5 10

<210> SEQ ID NO 114
<211> LENGTH: 12
<212> TYPE: PRT
<213> ORGANISM: Artificial Sequence
<220> FEATURE:
<223> OTHER INFORMATION: Synthetic sequence

<400> SEQUENCE: 114

Gln Gly Ala Trp Ala Asn Ile Ala Val Asp Lys Ala
1 5 10

<210> SEQ ID NO 115
<211> LENGTH: 12
<212> TYPE: PRT
<213> ORGANISM: Artificial Sequence
<220> FEATURE:
<223> OTHER INFORMATION: Synthetic sequence

<400> SEQUENCE: 115

Gln Gly Ala Leu Ala Asn Ile Ala Trp Asp Lys Ala
1 5 10

<210> SEQ ID NO 116
<211> LENGTH: 12
<212> TYPE: PRT
<213> ORGANISM: Artificial Sequence
<220> FEATURE:
<223> OTHER INFORMATION: Synthetic sequence

<400> SEQUENCE: 116

Gln Gly Ala Leu Ala Asn Ile Ala Val Asp Thr Ala
1 5 10

<210> SEQ ID NO 117
<211> LENGTH: 12
<212> TYPE: PRT
<213> ORGANISM: Artificial Sequence
<220> FEATURE:
<223> OTHER INFORMATION: Synthetic sequence

<400> SEQUENCE: 117

Gln Gly Ala Leu Ala Asn Ile Ala Pro Asp Lys Ala
1 5 10

<210> SEQ ID NO 118
<211> LENGTH: 12
<212> TYPE: PRT
<213> ORGANISM: Artificial Sequence
<220> FEATURE:
<223> OTHER INFORMATION: Synthetic sequence

<400> SEQUENCE: 118

Gln Gly Ala Leu Ala Asn Arg Ala Val Asp Lys Ala
1 5 10

<210> SEQ ID NO 119
<211> LENGTH: 12
<212> TYPE: PRT
<213> ORGANISM: Artificial Sequence
<220> FEATURE:
<223> OTHER INFORMATION: Synthetic sequence

<400> SEQUENCE: 119

Gln Gly Ala Leu Ala Leu Ile Ala Val Asp Lys Ala
1 5 10

<210> SEQ ID NO 120
<211> LENGTH: 12
<212> TYPE: PRT
<213> ORGANISM: Artificial Sequence
<220> FEATURE:
<223> OTHER INFORMATION: Synthetic sequence

<400> SEQUENCE: 120

Gln Gly Ala Leu Ala Asn Ile Ser Val Asp Lys Ala
1 5 10

<210> SEQ ID NO 121
<211> LENGTH: 12
<212> TYPE: PRT
<213> ORGANISM: Artificial Sequence
<220> FEATURE:
<223> OTHER INFORMATION: Synthetic sequence

<400> SEQUENCE: 121

Gln Gly Ala Leu Ala Asn Ile Ala Arg Asp Lys Ala
1 5 10

<210> SEQ ID NO 122
<211> LENGTH: 11
<212> TYPE: PRT
<213> ORGANISM: Artificial Sequence
<220> FEATURE:
<223> OTHER INFORMATION: Synthetic sequence

<400> SEQUENCE: 122

Gly Ala Leu Ala Asn Ile Ala Val Glu Lys Ala
1 5 10

<210> SEQ ID NO 123
<211> LENGTH: 12
<212> TYPE: PRT
<213> ORGANISM: Artificial Sequence
<220> FEATURE:
<223> OTHER INFORMATION: Synthetic sequence

<400> SEQUENCE: 123

Gln Gly Ala Leu Ala Asn Gly Ala Val Asp Lys Ala
1 5 10

<210> SEQ ID NO 124
<211> LENGTH: 12
<212> TYPE: PRT
<213> ORGANISM: Artificial Sequence
<220> FEATURE:
<223> OTHER INFORMATION: Synthetic sequence

<400> SEQUENCE: 124

Gln Gly Ala Leu Ala Asn Ile Ala Val Asp Lys His
1 5 10

<210> SEQ ID NO 125
<211> LENGTH: 12
<212> TYPE: PRT
<213> ORGANISM: Artificial Sequence
<220> FEATURE:
<223> OTHER INFORMATION: Synthetic sequence

<400> SEQUENCE: 125

Gln Gly Ala Leu Leu Asn Ile Ala Val Asp Lys Ala
1 5 10

<210> SEQ ID NO 126
<211> LENGTH: 12
<212> TYPE: PRT
<213> ORGANISM: Artificial Sequence
<220> FEATURE:
<223> OTHER INFORMATION: Synthetic sequence

<400> SEQUENCE: 126

Phe Gly Ala Leu Ala Asn Ile Ala Val Asp Lys Ala
1 5 10

<210> SEQ ID NO 127
<211> LENGTH: 12
<212> TYPE: PRT
<213> ORGANISM: Artificial Sequence
<220> FEATURE:
<223> OTHER INFORMATION: Synthetic sequence

<400> SEQUENCE: 127

Gln Gly Ala Leu Ala Asn Ile Ala Val Asp Glu Ala
1 5 10

<210> SEQ ID NO 128
<211> LENGTH: 12
<212> TYPE: PRT
<213> ORGANISM: Artificial Sequence
<220> FEATURE:
<223> OTHER INFORMATION: Synthetic sequence

<400> SEQUENCE: 128

Gln Gly Ala Leu Ala Asn Ile Ala Gly Asp Lys Ala
1 5 10

<210> SEQ ID NO 129
<211> LENGTH: 12
<212> TYPE: PRT
<213> ORGANISM: Artificial Sequence
<220> FEATURE:
<223> OTHER INFORMATION: Synthetic sequence

<400> SEQUENCE: 129

Gln Gly Ala Leu Ala Asn Ile Ala Val Asp His Ala
1 5 10

<210> SEQ ID NO 130
<211> LENGTH: 12
<212> TYPE: PRT
<213> ORGANISM: Artificial Sequence
<220> FEATURE:
<223> OTHER INFORMATION: Synthetic sequence

<400> SEQUENCE: 130

Gln Gly Ala Leu Ala Asn Ile His Val Asp Lys Ala
1 5 10

<210> SEQ ID NO 131
<211> LENGTH: 12
<212> TYPE: PRT
<213> ORGANISM: Artificial Sequence
<220> FEATURE:
<223> OTHER INFORMATION: Synthetic sequence

<400> SEQUENCE: 131

Gln Gly Ile Leu Ala Asn Ile Ala Val Asp Lys Ala
1 5 10

<210> SEQ ID NO 132
<211> LENGTH: 12
<212> TYPE: PRT
<213> ORGANISM: Artificial Sequence
<220> FEATURE:
<223> OTHER INFORMATION: Synthetic sequence

<400> SEQUENCE: 132

Gln Pro Ala Leu Ala Asn Ile Ala Val Asp Lys Ala
1 5 10

<210> SEQ ID NO 133
<211> LENGTH: 12
<212> TYPE: PRT
<213> ORGANISM: Artificial Sequence
<220> FEATURE:
<223> OTHER INFORMATION: Synthetic sequence

<400> SEQUENCE: 133

Gln Gly Ala Tyr Ala Asn Ile Ala Val Asp Lys Ala 1 5 10

<210> SEQ ID NO 134
<211> LENGTH: 12
<212> TYPE: PRT
<213> ORGANISM: Artificial Sequence
<220> FEATURE:
<223> OTHER INFORMATION: Synthetic sequence

<400> SEQUENCE: 134

Gln Phe Ala Leu Ala Asn Ile Ala Val Asp Lys Ala
1 5 10

<210> SEQ ID NO 135
<211> LENGTH: 12
<212> TYPE: PRT
<213> ORGANISM: Artificial Sequence
<220> FEATURE:
<223> OTHER INFORMATION: Synthetic sequence

<400> SEQUENCE: 135

Gln Gly Ala Leu Thr Asn Ile Ala Val Asp Lys Ala
1 5 10

<210> SEQ ID NO 136
<211> LENGTH: 12
<212> TYPE: PRT
<213> ORGANISM: Artificial Sequence
<220> FEATURE:
<223> OTHER INFORMATION: Synthetic sequence

<400> SEQUENCE: 136

Gln Gly Ala Leu Ala Asn Ile Ala Val Trp Lys Ala
1 5 10

<210> SEQ ID NO 137
<211> LENGTH: 12
<212> TYPE: PRT
<213> ORGANISM: Artificial Sequence
<220> FEATURE:
<223> OTHER INFORMATION: Synthetic sequence

<400> SEQUENCE: 137

Gln Gly Trp Leu Ala Asn Ile Ala Val Asp Lys Ala
1 5 10

<210> SEQ ID NO 138
<211> LENGTH: 12
<212> TYPE: PRT
<213> ORGANISM: Artificial Sequence
<220> FEATURE:
<223> OTHER INFORMATION: Synthetic sequence

<400> SEQUENCE: 138

Gln Gly Ala Thr Ala Asn Ile Ala Val Asp Lys Ala
1 5 10

<210> SEQ ID NO 139
<211> LENGTH: 12
<212> TYPE: PRT
<213> ORGANISM: Artificial Sequence
<220> FEATURE:
<223> OTHER INFORMATION: Synthetic sequence

<400> SEQUENCE: 139

Gln Gly Ala Leu Ala Asn Trp Ala Val Asp Lys Ala
1 5 10

<210> SEQ ID NO 140
<211> LENGTH: 12
<212> TYPE: PRT
<213> ORGANISM: Artificial Sequence
<220> FEATURE:
<223> OTHER INFORMATION: Synthetic sequence

<400> SEQUENCE: 140

Gln Tyr Ala Leu Ala Asn Ile Ala Val Asp Lys Ala
1 5 10

<210> SEQ ID NO 141
<211> LENGTH: 12
<212> TYPE: PRT
<213> ORGANISM: Artificial Sequence
<220> FEATURE:
<223> OTHER INFORMATION: Synthetic sequence

<400> SEQUENCE: 141

Gln Gly Ala Leu Ala Asn Ile Tyr Val Asp Lys Ala
1 5 10

<210> SEQ ID NO 142
<211> LENGTH: 12
<212> TYPE: PRT
<213> ORGANISM: Artificial Sequence
<220> FEATURE:
<223> OTHER INFORMATION: Synthetic sequence

<400> SEQUENCE: 142

Gln Gly Ala Leu Ala Asn Asp Ala Val Asp Lys Ala
1 5 10

<210> SEQ ID NO 143
<211> LENGTH: 12
<212> TYPE: PRT
<213> ORGANISM: Artificial Sequence
<220> FEATURE:
<223> OTHER INFORMATION: Synthetic sequence

<400> SEQUENCE: 143

Gln Gly Ala Leu Ala Asn Cys Ala Val Asp Lys Ala
1 5 10

<210> SEQ ID NO 144
<211> LENGTH: 12
<212> TYPE: PRT
<213> ORGANISM: Artificial Sequence
<220> FEATURE:
<223> OTHER INFORMATION: Synthetic sequence

<400> SEQUENCE: 144

Gln Gly Ala Leu Ala Asn Ile Ala Glu Asp Lys Ala
1 5 10

<210> SEQ ID NO 145
<211> LENGTH: 12
<212> TYPE: PRT
<213> ORGANISM: Artificial Sequence
<220> FEATURE:
<223> OTHER INFORMATION: Synthetic sequence

<400> SEQUENCE: 145

Gln Gly Ala Leu Ala Asn Ile Ala Val Asp Lys Gln
1 5 10

<210> SEQ ID NO 146
<211> LENGTH: 12
<212> TYPE: PRT
<213> ORGANISM: Artificial Sequence
<220> FEATURE:
<223> OTHER INFORMATION: Synthetic sequence

<400> SEQUENCE: 146

Gln Gly Ala Leu Ala Asn Ile Gln Val Asp Lys Ala
1 5 10

<210> SEQ ID NO 147
<211> LENGTH: 12
<212> TYPE: PRT
<213> ORGANISM: Artificial Sequence
<220> FEATURE:
<223> OTHER INFORMATION: Synthetic sequence

<400> SEQUENCE: 147

Gln Gly Ala Leu Ala Lys Ile Ala Val Asp Lys Ala
1 5 10

<210> SEQ ID NO 148
<211> LENGTH: 12
<212> TYPE: PRT
<213> ORGANISM: Artificial Sequence
<220> FEATURE:
<223> OTHER INFORMATION: Synthetic sequence

<400> SEQUENCE: 148

Gln Gly Ala Leu Ala Asn Ile Ala Val Asp Val Ala
1 5 10

<210> SEQ ID NO 149
<211> LENGTH: 12
<212> TYPE: PRT
<213> ORGANISM: Artificial Sequence
<220> FEATURE:
<223> OTHER INFORMATION: Synthetic sequence

<400> SEQUENCE: 149

Gln Gly Ala Leu Ala Asn Ile Val Val Asp Lys Ala
1 5 10

<210> SEQ ID NO 150
<211> LENGTH: 6
<212> TYPE: PRT
<213> ORGANISM: Artificial Sequence
<220> FEATURE:
<223> OTHER INFORMATION: Synthetic sequence

<400> SEQUENCE: 150

Trp Gln Asn Thr Leu Lys
1 5

<210> SEQ ID NO 151
<211> LENGTH: 6
<212> TYPE: PRT
<213> ORGANISM: Artificial Sequence
<220> FEATURE:
<223> OTHER INFORMATION: Synthetic sequence

<400> SEQUENCE: 151

Lys Gln Asn Thr Leu Trp
1 5

<210> SEQ ID NO 152
<211> LENGTH: 6
<212> TYPE: PRT
<213> ORGANISM: Artificial Sequence
<220> FEATURE:
<223> OTHER INFORMATION: Synthetic sequence

<400> SEQUENCE: 152

Lys Gln Asn Thr Leu Tyr
1               5

<210> SEQ ID NO 153
<211> LENGTH: 6
<212> TYPE: PRT
<213> ORGANISM: Artificial Sequence
<220> FEATURE:
<223> OTHER INFORMATION: Synthetic sequence

<400> SEQUENCE: 153

Lys Gln Asn Thr Leu Pro
1               5

<210> SEQ ID NO 154
<211> LENGTH: 6
<212> TYPE: PRT
<213> ORGANISM: Artificial Sequence
<220> FEATURE:
<223> OTHER INFORMATION: Synthetic sequence

<400> SEQUENCE: 154

Lys Gln Pro Thr Leu Lys
1               5

<210> SEQ ID NO 155
<211> LENGTH: 6
<212> TYPE: PRT
<213> ORGANISM: Artificial Sequence
<220> FEATURE:
<223> OTHER INFORMATION: Synthetic sequence

<400> SEQUENCE: 155

Val Gln Asn Thr Leu Lys
1               5

<210> SEQ ID NO 156
<211> LENGTH: 6
<212> TYPE: PRT
<213> ORGANISM: Artificial Sequence
<220> FEATURE:
<223> OTHER INFORMATION: Synthetic sequence

<400> SEQUENCE: 156

Lys Asn Asn Thr Leu Lys
1               5

<210> SEQ ID NO 157
<211> LENGTH: 6
<212> TYPE: PRT
<213> ORGANISM: Artificial Sequence
<220> FEATURE:
<223> OTHER INFORMATION: Synthetic sequence

<400> SEQUENCE: 157

Lys Gln Ile Thr Leu Lys
1               5

<210> SEQ ID NO 158

<211> LENGTH: 6
<212> TYPE: PRT
<213> ORGANISM: Artificial Sequence
<220> FEATURE:
<223> OTHER INFORMATION: Synthetic sequence

<400> SEQUENCE: 158

Lys Gln Asn Thr Asp Lys
1               5

<210> SEQ ID NO 159
<211> LENGTH: 6
<212> TYPE: PRT
<213> ORGANISM: Artificial Sequence
<220> FEATURE:
<223> OTHER INFORMATION: Synthetic sequence

<400> SEQUENCE: 159

Lys Thr Asn Thr Leu Lys
1               5

<210> SEQ ID NO 160
<211> LENGTH: 6
<212> TYPE: PRT
<213> ORGANISM: Artificial Sequence
<220> FEATURE:
<223> OTHER INFORMATION: Synthetic sequence

<400> SEQUENCE: 160

Lys Gln Asn Thr Leu Arg
1               5

<210> SEQ ID NO 161
<211> LENGTH: 6
<212> TYPE: PRT
<213> ORGANISM: Artificial Sequence
<220> FEATURE:
<223> OTHER INFORMATION: Synthetic sequence

<400> SEQUENCE: 161

Ser Gln Asn Thr Leu Lys
1               5

<210> SEQ ID NO 162
<211> LENGTH: 6
<212> TYPE: PRT
<213> ORGANISM: Artificial Sequence
<220> FEATURE:
<223> OTHER INFORMATION: Synthetic sequence

<400> SEQUENCE: 162

Lys Pro Asn Thr Leu Lys
1               5

<210> SEQ ID NO 163
<211> LENGTH: 6
<212> TYPE: PRT
<213> ORGANISM: Artificial Sequence
<220> FEATURE:
<223> OTHER INFORMATION: Synthetic sequence

<400> SEQUENCE: 163

Lys Gln Asp Thr Leu Lys
1               5

<210> SEQ ID NO 164
<211> LENGTH: 6

<212> TYPE: PRT
<213> ORGANISM: Artificial Sequence
<220> FEATURE:
<223> OTHER INFORMATION: Synthetic sequence

<400> SEQUENCE: 164

Lys Gln Asn Val Leu Lys
1               5

<210> SEQ ID NO 165
<211> LENGTH: 6
<212> TYPE: PRT
<213> ORGANISM: Artificial Sequence
<220> FEATURE:
<223> OTHER INFORMATION: Synthetic sequence

<400> SEQUENCE: 165

Leu Gln Asn Thr Leu Lys
1               5

<210> SEQ ID NO 166
<211> LENGTH: 6
<212> TYPE: PRT
<213> ORGANISM: Artificial Sequence
<220> FEATURE:
<223> OTHER INFORMATION: Synthetic sequence

<400> SEQUENCE: 166

Trp Gln Asn Thr Leu Lys
1               5

<210> SEQ ID NO 167
<211> LENGTH: 15
<212> TYPE: PRT
<213> ORGANISM: Arachis hypogaea

<400> SEQUENCE: 167

Glu Glu Gln Gly Ala Ile Val Thr Val Arg Gly Gly Leu Arg Ile
1               5                   10                  15

<210> SEQ ID NO 168
<211> LENGTH: 15
<212> TYPE: PRT
<213> ORGANISM: Arachis hypogaea

<400> SEQUENCE: 168

Glu Gln Gly Ala Ile Val Thr Val Arg Gly Gly Leu Arg Ile Leu
1               5                   10                  15

<210> SEQ ID NO 169
<211> LENGTH: 15
<212> TYPE: PRT
<213> ORGANISM: Arachis hypogaea

<400> SEQUENCE: 169

Gly Leu Met Ser Leu Ser Trp Met Ile Asn Phe Ile Arg Gln Val
1               5                   10                  15

<210> SEQ ID NO 170
<211> LENGTH: 15
<212> TYPE: PRT
<213> ORGANISM: Arachis hypogaea

<400> SEQUENCE: 170

Leu Val Ala Leu Ala Leu Phe Leu Leu Ala Ala His Ala Ser Ala
1               5                   10                  15

<210> SEQ ID NO 171
<211> LENGTH: 15
<212> TYPE: PRT
<213> ORGANISM: Arachis hypogaea

<400> SEQUENCE: 171

Gln Gly Ala Ile Val Thr Val Arg Gly Gly Leu Arg Ile Leu Ser
1 5 10 15

<210> SEQ ID NO 172
<211> LENGTH: 15
<212> TYPE: PRT
<213> ORGANISM: Arachis hypogaea

<400> SEQUENCE: 172

Thr Gly Asn Val Ala Ser Phe Leu Thr Ser Phe Ser Phe Glu Met
1 5 10 15

<210> SEQ ID NO 173
<211> LENGTH: 15
<212> TYPE: PRT
<213> ORGANISM: Arachis hypogaea

<400> SEQUENCE: 173

Ala Asn Tyr Ala Tyr Asn Tyr Ser Val Val Gly Gly Val Ala Leu
1 5 10 15

<210> SEQ ID NO 174
<211> LENGTH: 15
<212> TYPE: PRT
<213> ORGANISM: Arachis hypogaea

<400> SEQUENCE: 174

Phe Cys Ile Phe Phe Leu Ile Leu Phe Leu Ala Gln Glu Tyr Gly
1 5 10 15

<210> SEQ ID NO 175
<211> LENGTH: 15
<212> TYPE: PRT
<213> ORGANISM: Arachis hypogaea

<400> SEQUENCE: 175

Gly Phe Cys Ile Phe Phe Leu Ile Leu Phe Leu Ala Gln Glu Tyr
1 5 10 15

<210> SEQ ID NO 176
<211> LENGTH: 15
<212> TYPE: PRT
<213> ORGANISM: Arachis hypogaea

<400> SEQUENCE: 176

Gly Thr Ile Ile Gly Leu Ala Ile Ala Thr Pro Val Phe Thr Phe
1 5 10 15

<210> SEQ ID NO 177
<211> LENGTH: 15
<212> TYPE: PRT
<213> ORGANISM: Arachis hypogaea

<400> SEQUENCE: 177

Gly Thr Leu Leu Leu Phe Ala Gly Leu Ala Leu Ala Gly Thr Leu
1 5 10 15

```
<210> SEQ ID NO 178
<211> LENGTH: 15
<212> TYPE: PRT
<213> ORGANISM: Arachis hypogaea

<400> SEQUENCE: 178

Leu Arg Arg Pro Phe Tyr Ser Asn Ala Pro Gln Glu Ile Phe Ile
1               5                   10                  15


<210> SEQ ID NO 179
<211> LENGTH: 15
<212> TYPE: PRT
<213> ORGANISM: Arachis hypogaea

<400> SEQUENCE: 179

Asn Tyr Ala Tyr Asn Tyr Ser Val Val Gly Gly Val Ala Leu Pro
1               5                   10                  15


<210> SEQ ID NO 180
<211> LENGTH: 15
<212> TYPE: PRT
<213> ORGANISM: Arachis hypogaea

<400> SEQUENCE: 180

Pro Ala Ala Ile Thr Leu Ala Leu Ala Ala Gly Gly Phe Leu Phe
1               5                   10                  15


<210> SEQ ID NO 181
<211> LENGTH: 15
<212> TYPE: PRT
<213> ORGANISM: Arachis hypogaea

<400> SEQUENCE: 181

Arg Arg Pro Phe Tyr Ser Asn Ala Pro Gln Glu Ile Phe Ile Gln
1               5                   10                  15


<210> SEQ ID NO 182
<211> LENGTH: 14
<212> TYPE: PRT
<213> ORGANISM: Artificial Sequence
<220> FEATURE:
<223> OTHER INFORMATION: Synthetic sequence

<400> SEQUENCE: 182

Asn Tyr Ala Asn Tyr Ser Val Val Gly Gly Val Ala Leu Pro
1               5                   10


<210> SEQ ID NO 183
<211> LENGTH: 15
<212> TYPE: PRT
<213> ORGANISM: Artificial Sequence
<220> FEATURE:
<223> OTHER INFORMATION: Synthetic sequence

<400> SEQUENCE: 183

Ala Lys Leu Thr Ile Leu Val Ala Leu Ala Leu Phe Leu Leu Ala
1               5                   10                  15


<210> SEQ ID NO 184
<211> LENGTH: 15
<212> TYPE: PRT
<213> ORGANISM: Artificial Sequence
<220> FEATURE:
<223> OTHER INFORMATION: Synthetic sequence

<400> SEQUENCE: 184
```

```
Ala Thr Pro Leu Leu Val Ile Phe Ser Pro Ile Leu Val Pro Ala
1               5                   10                  15


<210> SEQ ID NO 185
<211> LENGTH: 15
<212> TYPE: PRT
<213> ORGANISM: Artificial Sequence
<220> FEATURE:
<223> OTHER INFORMATION: Synthetic sequence

<400> SEQUENCE: 185

Ala Ser Leu Lys Phe Ala Phe Val Met Leu Val Cys Met Ala Met
1               5                   10                  15


<210> SEQ ID NO 186
<211> LENGTH: 15
<212> TYPE: PRT
<213> ORGANISM: Artificial Sequence
<220> FEATURE:
<223> OTHER INFORMATION: Synthetic sequence

<400> SEQUENCE: 186

Ala Thr Pro Val Phe Thr Phe Phe Ser Pro Val Ile Val Pro Ala
1               5                   10                  15


<210> SEQ ID NO 187
<211> LENGTH: 15
<212> TYPE: PRT
<213> ORGANISM: Artificial Sequence
<220> FEATURE:
<223> OTHER INFORMATION: Synthetic sequence

<400> SEQUENCE: 187

Cys Ile Phe Phe Leu Ile Leu Phe Leu Ala Gln Glu Tyr Gly Val
1               5                   10                  15


<210> SEQ ID NO 188
<211> LENGTH: 15
<212> TYPE: PRT
<213> ORGANISM: Artificial Sequence
<220> FEATURE:
<223> OTHER INFORMATION: Synthetic sequence

<400> SEQUENCE: 188

Met Ala Lys Leu Thr Leu Leu Val Ala Leu Ala Leu Phe Leu Leu
1               5                   10                  15


<210> SEQ ID NO 189
<211> LENGTH: 15
<212> TYPE: PRT
<213> ORGANISM: Artificial Sequence
<220> FEATURE:
<223> OTHER INFORMATION: Synthetic sequence

<400> SEQUENCE: 189

Cys Ile Phe Phe Leu Val Leu Phe Leu Ala Gln Glu Gly Val Val
1               5                   10                  15


<210> SEQ ID NO 190
<211> LENGTH: 15
<212> TYPE: PRT
<213> ORGANISM: Artificial Sequence
<220> FEATURE:
<223> OTHER INFORMATION: Synthetic sequence

<400> SEQUENCE: 190

Met Ala Ser Leu Lys Phe Ala Phe Val Met Leu Val Cys Met Ala
```

1 5 10 15

<210> SEQ ID NO 191
<211> LENGTH: 15
<212> TYPE: PRT
<213> ORGANISM: Artificial Sequence
<220> FEATURE:
<223> OTHER INFORMATION: Synthetic sequence

<400> SEQUENCE: 191

Met Ile Asp Phe Glu Glu Phe Arg Val Met Met Met Met Gly Ser
1 5 10 15

<210> SEQ ID NO 192
<211> LENGTH: 15
<212> TYPE: PRT
<213> ORGANISM: Artificial Sequence
<220> FEATURE:
<223> OTHER INFORMATION: Synthetic sequence

<400> SEQUENCE: 192

Asp Phe Glu Glu Phe Arg Val Met Met Met Met Gly Ser Arg His
1 5 10 15

<210> SEQ ID NO 193
<211> LENGTH: 15
<212> TYPE: PRT
<213> ORGANISM: Artificial Sequence
<220> FEATURE:
<223> OTHER INFORMATION: Synthetic sequence

<400> SEQUENCE: 193

Met Met Val Lys Leu Ser Ile Leu Val Ala Leu Leu Gly Ala Leu
1 5 10 15

<210> SEQ ID NO 194
<211> LENGTH: 15
<212> TYPE: PRT
<213> ORGANISM: Artificial Sequence
<220> FEATURE:
<223> OTHER INFORMATION: Synthetic sequence

<400> SEQUENCE: 194

Asp Gly Met Ile Asp Phe Glu Glu Phe Arg Val Met Met Met Met
1 5 10 15

<210> SEQ ID NO 195
<211> LENGTH: 15
<212> TYPE: PRT
<213> ORGANISM: Artificial Sequence
<220> FEATURE:
<223> OTHER INFORMATION: Synthetic sequence

<400> SEQUENCE: 195

Asp Gly Tyr Ile Ser Leu Gln Glu Phe Ile Glu Leu Asn Thr Lys
1 5 10 15

<210> SEQ ID NO 196
<211> LENGTH: 15
<212> TYPE: PRT
<213> ORGANISM: Artificial Sequence
<220> FEATURE:
<223> OTHER INFORMATION: Synthetic sequence

<400> SEQUENCE: 196

Met Val Lys Leu Ser Ile Leu Val Ala Leu Leu Gly Ala Leu Leu
1 5 10 15

<210> SEQ ID NO 197
<211> LENGTH: 15
<212> TYPE: PRT
<213> ORGANISM: Artificial Sequence
<220> FEATURE:
<223> OTHER INFORMATION: Synthetic sequence

<400> SEQUENCE: 197

Phe Glu Glu Phe Arg Val Met Met Met Met Gly Ser Arg His Asp
1 5 10 15

<210> SEQ ID NO 198
<211> LENGTH: 15
<212> TYPE: PRT
<213> ORGANISM: Artificial Sequence
<220> FEATURE:
<223> OTHER INFORMATION: Synthetic sequence

<400> SEQUENCE: 198

Asn Ile Phe Ser Gly Phe Thr Pro Glu Phe Leu Glu Gln Ala Phe
1 5 10 15

<210> SEQ ID NO 199
<211> LENGTH: 15
<212> TYPE: PRT
<213> ORGANISM: Artificial Sequence
<220> FEATURE:
<223> OTHER INFORMATION: Synthetic sequence

<400> SEQUENCE: 199

Phe Phe Leu Ile Leu Phe Leu Ala Gln Glu Tyr Gly Val Glu Gly
1 5 10 15

<210> SEQ ID NO 200
<211> LENGTH: 15
<212> TYPE: PRT
<213> ORGANISM: Artificial Sequence
<220> FEATURE:
<223> OTHER INFORMATION: Synthetic sequence

<400> SEQUENCE: 200

Asn Pro Phe Lys Phe Phe Val Pro Pro Phe Gln Gln Ser Pro Arg
1 5 10 15

<210> SEQ ID NO 201
<211> LENGTH: 15
<212> TYPE: PRT
<213> ORGANISM: Artificial Sequence
<220> FEATURE:
<223> OTHER INFORMATION: Synthetic sequence

<400> SEQUENCE: 201

Phe Phe Leu Val Leu Phe Leu Ala Gln Glu Gly Val Val Lys Thr
1 5 10 15

<210> SEQ ID NO 202
<211> LENGTH: 15
<212> TYPE: PRT
<213> ORGANISM: Artificial Sequence
<220> FEATURE:
<223> OTHER INFORMATION: Synthetic sequence

<400> SEQUENCE: 202

Pro Leu Phe Ile Leu Phe Ser Pro Val Ile Val Pro Ala Thr Ile
1 5 10 15

<210> SEQ ID NO 203
<211> LENGTH: 15
<212> TYPE: PRT
<213> ORGANISM: Artificial Sequence
<220> FEATURE:
<223> OTHER INFORMATION: Synthetic sequence

<400> SEQUENCE: 203

Phe Leu Ile Leu Phe Leu Ala Gln Glu Tyr Gly Val Glu Gly Lys
1 5 10 15

<210> SEQ ID NO 204
<211> LENGTH: 14
<212> TYPE: PRT
<213> ORGANISM: Artificial Sequence
<220> FEATURE:
<223> OTHER INFORMATION: Synthetic sequence

<400> SEQUENCE: 204

Pro Val Phe Ile Phe Phe Ser Pro Val Ile Val Pro Ala Trp
1 5 10

<210> SEQ ID NO 205
<211> LENGTH: 14
<212> TYPE: PRT
<213> ORGANISM: Artificial Sequence
<220> FEATURE:
<223> OTHER INFORMATION: Synthetic sequence

<400> SEQUENCE: 205

Phe Leu Val Leu Phe Leu Ala Gln Glu Gly Trp Lys Thr Glu
1 5 10

<210> SEQ ID NO 206
<211> LENGTH: 15
<212> TYPE: PRT
<213> ORGANISM: Artificial Sequence
<220> FEATURE:
<223> OTHER INFORMATION: Synthetic sequence

<400> SEQUENCE: 206

Pro Val Phe Thr Phe Phe Ser Pro Val Ile Val Pro Ala Val Val
1 5 10 15

<210> SEQ ID NO 207
<211> LENGTH: 15
<212> TYPE: PRT
<213> ORGANISM: Artificial Sequence
<220> FEATURE:
<223> OTHER INFORMATION: Synthetic sequence

<400> SEQUENCE: 207

Phe Ser Gly Phe Ala Gln Glu Phe Leu Gln His Ala Phe Gln Val
1 5 10 15

<210> SEQ ID NO 208
<211> LENGTH: 15
<212> TYPE: PRT
<213> ORGANISM: Artificial Sequence
<220> FEATURE:
<223> OTHER INFORMATION: Synthetic sequence

<400> SEQUENCE: 208

Gln Ala Ile Lys Phe Met Thr Ala Ser Thr Ile Gly Val Ser Phe
1 5 10 15

<210> SEQ ID NO 209
<211> LENGTH: 15
<212> TYPE: PRT
<213> ORGANISM: Artificial Sequence
<220> FEATURE:
<223> OTHER INFORMATION: Synthetic sequence

<400> SEQUENCE: 209

Phe Ser Gly Phe Thr Pro Glu Phe Leu Ala Gln Ala Phe Gln Val
1 5 10 15

<210> SEQ ID NO 210
<211> LENGTH: 15
<212> TYPE: PRT
<213> ORGANISM: Artificial Sequence
<220> FEATURE:
<223> OTHER INFORMATION: Synthetic sequence

<400> SEQUENCE: 210

Arg Gln Ala Ile Lys Phe Met Thr Ala Ser Thr Ile Gly Val Ser
1 5 10 15

<210> SEQ ID NO 211
<211> LENGTH: 15
<212> TYPE: PRT
<213> ORGANISM: Artificial Sequence
<220> FEATURE:
<223> OTHER INFORMATION: Synthetic sequence

<400> SEQUENCE: 211

Gly Phe Ala Gln Glu Phe Leu Gln His Ala Phe Gln Val Asp Arg
1 5 10 15

<210> SEQ ID NO 212
<211> LENGTH: 15
<212> TYPE: PRT
<213> ORGANISM: Artificial Sequence
<220> FEATURE:
<223> OTHER INFORMATION: Synthetic sequence

<400> SEQUENCE: 212

Ser Gly Phe Ala Gln Glu Phe Leu Gln His Ala Phe Gln Val Asp
1 5 10 15

<210> SEQ ID NO 213
<211> LENGTH: 15
<212> TYPE: PRT
<213> ORGANISM: Artificial Sequence
<220> FEATURE:
<223> OTHER INFORMATION: Synthetic sequence

<400> SEQUENCE: 213

Gly Phe Cys Ile Phe Phe Leu Ile Leu Phe Leu Ala Gln Glu Tyr
1 5 10 15

<210> SEQ ID NO 214
<211> LENGTH: 15
<212> TYPE: PRT
<213> ORGANISM: Artificial Sequence
<220> FEATURE:
<223> OTHER INFORMATION: Synthetic sequence

<400> SEQUENCE: 214

Ser Gly Phe Thr Pro Glu Phe Leu Ala Gln Ala Phe Gln Val Asp
1 5 10 15

<210> SEQ ID NO 215

<211> LENGTH: 15
<212> TYPE: PRT
<213> ORGANISM: Artificial Sequence
<220> FEATURE:
<223> OTHER INFORMATION: Synthetic sequence

<400> SEQUENCE: 215

Gly Ser Asn Ile Phe Ser Gly Phe Ala Gln Glu Phe Leu Gln His
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: Synthetic sequence

<400> SEQUENCE: 216

Thr Gly Gly Thr Leu Leu Leu Leu Ser Gly Leu Ser Leu Leu Gly
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: Synthetic sequence

<400> SEQUENCE: 217

Gly Thr Leu Leu Leu Leu Ser Gly Leu Ser Leu Leu Gly Thr Ile
1               5                   10                  15

<210> SEQ ID NO 218
<211> LENGTH: 15
<212> TYPE: PRT
<213> ORGANISM: Artificial Sequence
<220> FEATURE:
<223> OTHER INFORMATION: Synthetic sequence

<400> SEQUENCE: 218

Thr Gly Thr Val Ile Gly Leu Ile Ile Ala Thr Pro Leu Leu Val
1               5                   10                  15

<210> SEQ ID NO 219
<211> LENGTH: 15
<212> TYPE: PRT
<213> ORGANISM: Artificial Sequence
<220> FEATURE:
<223> OTHER INFORMATION: Synthetic sequence

<400> SEQUENCE: 219

Ile Phe Phe Leu Ile Leu Phe Leu Ala Gln Glu Tyr Gly Val Glu
1               5                   10                  15

<210> SEQ ID NO 220
<211> LENGTH: 15
<212> TYPE: PRT
<213> ORGANISM: Artificial Sequence
<220> FEATURE:
<223> OTHER INFORMATION: Synthetic sequence

<400> SEQUENCE: 220

Thr Pro Leu Phe Ile Leu Phe Ser Pro Val Ile Val Pro Ala Ile
1               5                   10                  15

<210> SEQ ID NO 221
<211> LENGTH: 15

<212> TYPE: PRT
<213> ORGANISM: Artificial Sequence
<220> FEATURE:
<223> OTHER INFORMATION: Synthetic sequence

<400> SEQUENCE: 221

Ile Phe Phe Leu Val Leu Phe Leu Ala Gln Glu Gly Val Val Lys
1 5 10 15

<210> SEQ ID NO 222
<211> LENGTH: 15
<212> TYPE: PRT
<213> ORGANISM: Artificial Sequence
<220> FEATURE:
<223> OTHER INFORMATION: Synthetic sequence

<400> SEQUENCE: 222

Thr Pro Leu Leu Val Ile Phe Ser Pro Ile Leu Val Pro Ala Ala
1 5 10 15

<210> SEQ ID NO 223
<211> LENGTH: 15
<212> TYPE: PRT
<213> ORGANISM: Artificial Sequence
<220> FEATURE:
<223> OTHER INFORMATION: Synthetic sequence

<400> SEQUENCE: 223

Ile Phe Ser Gly Phe Thr Pro Glu Phe Leu Glu Gln Ala Phe Gln
1 5 10 15

<210> SEQ ID NO 224
<211> LENGTH: 15
<212> TYPE: PRT
<213> ORGANISM: Artificial Sequence
<220> FEATURE:
<223> OTHER INFORMATION: Synthetic sequence

<400> SEQUENCE: 224

Thr Pro Val Phe Ile Phe Phe Ser Pro Val Ile Val Pro Ala Val
1 5 10 15

<210> SEQ ID NO 225
<211> LENGTH: 15
<212> TYPE: PRT
<213> ORGANISM: Artificial Sequence
<220> FEATURE:
<223> OTHER INFORMATION: Synthetic sequence

<400> SEQUENCE: 225

Ile Arg Gln Ala Ile Lys Phe Met Thr Ala Ser Thr Ile Gly Val
1 5 10 15

<210> SEQ ID NO 226
<211> LENGTH: 15
<212> TYPE: PRT
<213> ORGANISM: Artificial Sequence
<220> FEATURE:
<223> OTHER INFORMATION: Synthetic sequence

<400> SEQUENCE: 226

Thr Pro Val Phe Thr Phe Phe Ser Pro Val Ile Val Pro Ala Val
1 5 10 15

<210> SEQ ID NO 227
<211> LENGTH: 14
<212> TYPE: PRT

<213> ORGANISM: Artificial Sequence
<220> FEATURE:
<223> OTHER INFORMATION: Synthetic sequence

<400> SEQUENCE: 227

Lys Leu Ser Ile Leu Val Ala Leu Leu Gly Ala Leu Leu Trp
1 5 10

<210> SEQ ID NO 228
<211> LENGTH: 15
<212> TYPE: PRT
<213> ORGANISM: Artificial Sequence
<220> FEATURE:
<223> OTHER INFORMATION: Synthetic sequence

<400> SEQUENCE: 228

Thr Thr Pro Leu Phe Ile Leu Phe Ser Pro Val Ile Val Pro Ala
1 5 10 15

<210> SEQ ID NO 229
<211> LENGTH: 15
<212> TYPE: PRT
<213> ORGANISM: Artificial Sequence
<220> FEATURE:
<223> OTHER INFORMATION: Synthetic sequence

<400> SEQUENCE: 229

Leu Met Ser Leu Ser Trp Met Ile Asn Phe Ile Arg Gln Val His
1 5 10 15

<210> SEQ ID NO 230
<211> LENGTH: 15
<212> TYPE: PRT
<213> ORGANISM: Artificial Sequence
<220> FEATURE:
<223> OTHER INFORMATION: Synthetic sequence

<400> SEQUENCE: 230

Thr Val Ile Gly Leu Ile Ile Ala Thr Pro Leu Leu Val Ile Phe
1 5 10 15

<210> SEQ ID NO 231
<211> LENGTH: 15
<212> TYPE: PRT
<213> ORGANISM: Artificial Sequence
<220> FEATURE:
<223> OTHER INFORMATION: Synthetic sequence

<400> SEQUENCE: 231

Leu Asn Leu Leu Ile Leu Arg Trp Leu Gly Leu Ser Ala Glu Tyr
1 5 10 15

<210> SEQ ID NO 232
<211> LENGTH: 15
<212> TYPE: PRT
<213> ORGANISM: Artificial Sequence
<220> FEATURE:
<223> OTHER INFORMATION: Synthetic sequence

<400> SEQUENCE: 232

Val Lys Leu Ser Ile Leu Val Ala Leu Leu Gly Ala Leu Leu Val
1 5 10 15

<210> SEQ ID NO 233
<211> LENGTH: 15
<212> TYPE: PRT
<213> ORGANISM: Artificial Sequence -continued

```
<220> FEATURE:
<223> OTHER INFORMATION: Synthetic sequence

<400> SEQUENCE: 233

Leu Ser Ser Phe Ser Trp Val Met Asn Tyr Ile Arg Gln Thr His
1               5                   10                  15
```